(12) United States Patent
Lee et al.

(10) Patent No.: US 7,091,199 B1
(45) Date of Patent: Aug. 15, 2006

(54) THIENOISOXAZOLE PHENOXY UNSUBSTITUTED ETHYL AND PROPYL DERIVATIVES USEFUL AS $D_4$ ANTAGONISTS

(75) Inventors: George E. Lee, Somerville, NJ (US);
John G. Jurcak, Bethlehem, PA (US);
Timothy A. Ayers, Bridgewater, NJ (US)

(73) Assignee: Aventis Pharmaceuticals Inc., Bridgewater, NJ (US)

(*) Notice: Subject to any disclaimer, the term of this patent is extended or adjusted under 35 U.S.C. 154(b) by 283 days.

(21) Appl. No.: 10/088,369

(22) PCT Filed: Sep. 13, 2000

(86) PCT No.: PCT/US00/24949

§ 371 (c)(1),
(2), (4) Date: Dec. 23, 2002

(87) PCT Pub. No.: WO01/19832

PCT Pub. Date: Mar. 22, 2001

Related U.S. Application Data

(60) Provisional application No. 60/229,356, filed on Sep. 14, 1999.

(51) Int. Cl.
*A61K 31/55* (2006.01)
*C07D 403/00* (2006.01)
*C07D 413/04* (2006.01)
*C07D 401/41* (2006.01)
*C07D 261/20* (2006.01)

(52) U.S. Cl. ............... 514/217.1; 514/233.5; 514/233.8; 514/252; 514/254.04; 514/318; 514/444; 548/242; 546/207; 546/272.1; 544/368; 544/357; 540/480; 540/593; 540/602

(58) Field of Classification Search ............ 548/242; 549/73; 546/207, 272.1; 544/368, 357, 544/35; 540/480, 602, 593; 514/217.1, 514/233.5, 318, 319, 233.8, 252, 254.04, 514/389, 444, 333
See application file for complete search history.

(56) References Cited

U.S. PATENT DOCUMENTS

| | | | |
|---|---|---|---|
| 4,075,227 A | 2/1978 | Jones et al. |
| 4,085,114 A | 4/1978 | Adachi et al. |
| 4,355,037 A | 10/1982 | Strupczewski et al. |
| 4,408,053 A | 10/1983 | Strupczewski et al. |
| 4,408,054 A | 10/1983 | Strupczewski et al. |
| 4,427,691 A | 1/1984 | Shutske et al. |
| 4,452,804 A | 6/1984 | Shutske et al. |
| 4,469,869 A | 9/1984 | Strupczewski et al. |
| 4,504,669 A | 3/1985 | Shutske et al. |
| 4,528,376 A | 7/1985 | Strupczewski et al. |
| 4,644,064 A | 2/1987 | Shutske et al. |
| 4,728,651 A | 3/1988 | Ong et al. |
| 4,769,472 A | 9/1988 | Ong et al. |
| 5,114,936 A | 5/1992 | Wettlaufer et al. |
| 5,143,923 A | 9/1992 | Hrib et al. |
| 5,177,088 A | 1/1993 | Effland et al. |
| 5,180,834 A | 1/1993 | Wettlaufer et al. |
| 5,225,412 A | 7/1993 | Hrib et al. |
| 5,225,414 A | 7/1993 | Henning et al. |
| 5,254,595 A | 10/1993 | Guzzi et al. |
| 5,256,672 A | 10/1993 | Wettlaufer et al. |
| 5,321,037 A | 6/1994 | Nagano et al. |
| 5,328,920 A | 7/1994 | Effland et al. |
| 5,340,833 A | 8/1994 | Bridges et al. |
| 5,576,319 A | 11/1996 | Baker et al. |
| 5,593,994 A | 1/1997 | Batt et al. |
| 5,696,113 A | 12/1997 | Palermo et al. |
| 5,780,474 A | 7/1998 | Peglion et al. |
| 5,843,940 A | 12/1998 | Cullinan et al. |
| 5,852,022 A | 12/1998 | Palermo et al. |
| 5,856,503 A | 1/1999 | Aebi et al. |
| 5,932,586 A | 8/1999 | Batt et al. |
| 5,965,554 A | 10/1999 | Palermo et al. |
| 6,008,348 A | 12/1999 | Palermo et al. |
| 6,022,880 A | 2/2000 | Effland et al. |
| 6,103,724 A | 8/2000 | Laszlovszky et al. |
| 6,121,293 A | 9/2000 | Cullinan et al. |

FOREIGN PATENT DOCUMENTS

| | | |
|---|---|---|
| EP | 0058977 | 9/1982 |
| EP | 0221414 | 5/1987 |
| EP | 0729955 | 9/1996 |
| GB | 1269776 | 4/1972 |
| JP | 10095770 | 4/1998 |

(Continued)

OTHER PUBLICATIONS

Van Tol et al., "Cloning of the gene for a human dopamine D4 receptor with high affinity for the antipsychotic clozapine", Letters to Nature, vol. 350 (1991) pp. 610-614.*

(Continued)

*Primary Examiner*—Johann Richter
*Assistant Examiner*—Ebenezer Sackey
(74) *Attorney, Agent, or Firm*—Barbara E. Kurys

(57) ABSTRACT

The compounds are of the class of thienoisoxazole phenoxy unsubstituted ethyl and propyl derivatives, useful as $D_4$ antagonists. Said compounds are useful for the treatment of medical conditions mediated by inhibition of $D_4$ receptor. These conditions comprise, for example, Attention Deficit Hyperactivity Disorder, Obsessive-Compulsive Disorder, Psychoses, Substance Abuse, Substance Dependence, Parkinson's Disease, Parkinsonism, Tardive Diskinesia, Gilles de la Tourette Syndrome, Conduct Disorder, and Oppositional Defiant Disorder. A further aspect of the invention is to provide a pharmaceutical composition, intermediates, and a method of making said class of compounds.

93 Claims, No Drawings

FOREIGN PATENT DOCUMENTS

| WO | WO 92/08718   |   | 5/1992 |
|----|---------------|---|--------|
| WO | WO 97/23482   |   | 7/1997 |
| WO | WO 97/28115   |   | 8/1997 |
| WO | WO 97/40027   |   | 10/1997 |
| WO | WO 99/40067   |   | 8/1999 |
| WO | WO 01/19833   |   | 3/2001 |
| WO | WO 2001019833 | * | 3/2001 |

OTHER PUBLICATIONS

Newman, "Novel pharmacotherapies for Cocaine abuse 1997-2000", Medicinal Chemistry Section, National Institute on Drug Abuse-Intramural Research Program, Expect Opinion on Therapeutic Patients, (2000), 10 (7).*
Asghari, V., et. al., Dopamine D4 Receptor Repeat: Analysis of Different Native and Mutant Forms of the Human and Rat Genes, Molecular Pharmacology vol. 46, pp. 364-373 (1994).
Bassitt, D.P., et. al., Clozapine Efficacy in Tardive Dyskinesia in Schizoprenic Patients, European Archives of Psychiatry and Clinical Neuroscience vol. 248, pp. 209-211 (1998).
Benjamin, J., et. al., Population and Familial Association between the D4 Dopamine Receptor gene and Measures of Novelty Seeking, Nature Genetics vol. 12, pp. 81-84 (1996).
Bryce, M., et. al., Synthesis and Cyclic Voltammetric Behaviour of Some 3-Substituted Thiophenes and Pyrroles: Precursors for the Prepration of Conducting Polymers, Synthetic Metal, vol. 26, (1988) pp. 153-168.
Corbett, R., et. al., Iloperidone: Preclinical Profile and Early Clinical Evaluation, CNS Drug Review vol. 3, No. 2, pp. 120-147 (1997).
Crenshaw, R.R., et. al., Potential Antifertility Agents, 1. Substituted Diarl Derivatives of Benzo[b]Thiophenes, Benzo[b]furans, 1H-2-Benzothiapyrans, and 2H-1-Benzothiapyrans1, Journal of Medicinal Chemistry, vol. 14, No. 12, (1971) pp. 1185-1190.
Cruz, C., et. al., Increased Prevalence of the Seven-Repeat Variant of the Dopamine D4 Receptor Gene in Patients with Obsessive-Compulsive Disorder with Tics, Neuroscience Letters vol. 231, pp. 1-4, (1997).
Ebstein, R.E., et. al., Dopamine D4 Receptor (D4DR) exon III Polymorphism Associated with the Human Personality Trait of Novelty Seeking, Nature Genetics vol. 12, (1996) pp. 78-80.
Elworthy, T.R., et. al., N-Arylpiperazinyl-N-Propytamino Derivatives of Heteroaryl Amides as Functional Uroselective a1-Adrenoceptor Antagonists, Indian Journal of Chemistry—part B Organic Including Medicinal vol. 40, pp. 2674-1348, (1985).
Erenberg, G., et. al., Giles De La Tourette's Syndrome: Effects of Stimulant Drugs, Neurology vol. 35, No. 35, pp. 1346-1348, (1985).
Factor, S.A., et. al., The Emerging Role od Clozapine in the Treatment od Movement Disorders, Movement Disorders vol. 12, No. 4 (1997) pp. 483-496.
Feldpausch, D.L., et. al., The Role of Dopamine D4 Receptor in the Induction of Behavioral Sensitization to Amphetamine and Accompanying Biochemical and Molecular Adaptations, Journal of Pharmacology and Experimental Therapeutics vol. 266, pp. 497-508 (1998).
Friedman, J.H., et. al., Substituting Clozapine for Olanzapine in Psychiatrically Stable Parkinson's Disease Patients: Result of an Open Label for Pilot Study, Clinical Neuropharmacology, vol. 21, No. 5 pp. 285-288 (1998).
Grice, D.E., et. al., Linkage Disequilibrium between an Allele at the Dopamine D4 Receptor Locus and Tourette Syndrome, by the Transmission-Disequilibrium Test, American Journal of Human Genetics vol. 59, pp. 644-652 (1996).
Helsley, G.C., et. al., Piperidyalkylindoles. 1. Hypotensive Activity of 3-[2-(Phenoxypiperidyl)ethyl]Indoles, Journal of Medicinal Chemistry, (1978), vol. 21, No. 3 pp. 309-312.
Lahoste, G., et. al., Dopamine D4 Receptor Gene Polymorphism is Associated with Attention Deficit Hyperactivity Disorder, Molecular Psychiatry vol. 1, pp. 121-124 (1996).
Lahti, R.A., et. al., Direct Determination of Dopamine D4 Receptors in Normal and Schizophrenic Postmortem Brain Tissue: A [3H]NGD-94-1 Study, Molecular Psychiatry vol. 3, pp. 528-533 (1998).
Magdo, I., et. al., 3D quantitative structure-activity relationship (CoMFA) study of heterocyclic arylpiperazine derivatives with 5-HT1A activity, Database Chemabs 'Online! Chemical Abstracts Service, Columbus, Ohio, US.
Ricketts, H., et. al., Association of Long Variants of the Dopamine D4 Receptor Exon 3 Repeat Polymorphism with Parkinson's Disease, Clinical Genetics vol. 54, pp. 33-38 (1998).
Rubinstein, M., et. al., Mice Lacking Dopamine D4 Receptors are Supersitive to Ethanol, Cocaine, and Methamphetamine, Cell, vol. 991-1001 (1997).
Sall, D., e.t al., Dibasic Benzo[b]thiophene Derivatives as a Novel Class of Active Site-Directed Thrombin Inhibitors. 1. Determination of the Serine Protease Selectivity, Structure—Activity Relationships, and Binding Orientation, Journal of Medicinal Chemistry vol. 40, No. 22, (1997) pp. 3489-3493.
Schoder, J., et. al., D2 Dopamine Receptor Up-Regulation, Treatment Response, Neurological Soft Signs, and Extrapyramidal Side Effects in Schizophrenia: A Follow-Up Study with 123I-Iodobenzamide Single Photon Emission Compouted Tomography in the Drug Naive State and after Neuroleptic Treatment, Society of Biological Psychiatry vol. 43, pp. 660-665, (1998).
Seeman, P., et. al., Atypical Neuroleptics Have Low Affinity for Dopamine D2 Receptors or Are Selectivefor D4 Receptors, Neuropoychoppharmacology vol. 16, Iss. 2, pp. 92-135 (1997).
Seeman, P., et. al., Schizophrenia: Eleveation of dopamine D4-like sites, using [3H]Nemonapride and [125I]Epidepride , European Journal of Pharmacology vol. 286 (1995) R3-R5.
Shields, P.G., et. al., Dopamine D4 Receptors and the Risk of Cigarette Smoke in African-Americans and Caucasians1, Cancer Epidemiology, Biomarkers & Prevention vol. 7, pp. 453-458 (1998).
Van Tol, H.M., et. al., Cloning of the gene for a human dopamine D4 receptor with high affinity for the antipsychotic clozapine, Letters to Nature, vol. 350, 1991, pp 610-614.
Van Tol, H.M., et. al., The Dopamine D4 Receptor: A Novel Site for Antipsychotic Action , Clinical Neuropharmacology vol. 18, No. 1 pp. 5143-5153 (1995).
Vantol, H.M., et. al., Multiple Dopamine D4 Receptor Variants in the Human Population , Nature vol. 358-9 (1992)—pp. 149-152.
Zhu, J., et. al., Synthesis of 2-(4-Halogenobenzyl)-3-Arylbenzo[b]-Thiopenes and a 2-(4-Fluorobenzyl)-3-Arylbenzo[b]-Selenophene as Selective Ligands for Antiestrogen-Binding Sites.
Kongsamut, S., et al., Iloperidone Binding to Human and Rat Dopamine and 5-HT Receptors, Database Chemabs online! Chemical Abstracts Service, Columbus, Ohio, US retrieved from STN Database Accession No. 126:70003 XP002154323 * Eur. J. Pharmacol. (1996) vol.317, (2/3).

* cited by examiner

THIENOISOXAZOLE PHENOXY UNSUBSTITUTED ETHYL AND PROPYL DERIVATIVES USEFUL AS D$_4$ ANTAGONISTS

This application is a 371 of PCT/US00/24949, Filed Sep. 13, 2000, and claims the benefit of U.S. Provisional No. 60/229,356, Filed Sep. 14, 1999.

FIELD OF THE INVENTION

The present invention comprises compounds of Formula I useful as therapeutic agents for conditions treated by antagonizing D$_4$ receptor stimulation, e.g., Attention Deficit Hyperactivity Disorder, Obsessive Compulsive Disorder and Psychoses. Intermediates, method of making the compounds and methods of using the compounds are also claimed.

BACKGROUND OF THE INVENTION

The relatively new science of molecular biology has allowed new insights into the mechanisms of CNS diseases via the isolation and cloning of receptor subtypes. Thus, while earlier functional studies had distinguished only two subtypes of dopamine receptor, to date five distinct subtypes have been identified. The dopamine D$_4$ receptor was first cloned in 1991 by Van Tol, Seeman, Civelli, et al. and shown to be localized in the limbic regions of the brain, areas associated with cognitive and emotional behaviors (Van Tol, H. H. M.; Bunzow, J. R.; Guan, H-C.; Sunahara, R. K.; P. Seeman, Niznik, H. B.; Civelli, O.; Cloning of the gene for a human dopamine D$_4$ receptor with high affinity for the antipsychotic clozapine. Nature 1991, 350, 610.)

The D$_4$ receptor was also localized to the frontal cortex implying a role in cognition and executive function. Furthermore, it has been reported that the selective D$_4$ antagonist NGD-94-1 caused improvement in performance retention in a passive avoidance test in rodents and improved performance in a spatial water maze task. (Tallman, J. NGD-94-1; A Specific Dopamine D$_4$ Antagonist. Catecholamines-Bridging Basic Science with Clinical Medicine. Goldstein, D. S.; Eisenhofer, G.; McCarty, R., Eds.; Academic Press: New York, 1997). The effects of this compound in these assays are consistent with the anatomical localization of the D$_4$ receptor in the cortex, hippocampus and thalamus.

Genetic linkage and association studies using polymorphism have been carried out to obtain insights into the possible roles for this receptor in disease. It has been reported that there is a positive association between the repeat polymorphism of seven repeat units and a number of clinical conditions which have a high degree of comorbidity such as Attention Deficit Hyperactivity Disorder and Obsessive Compulsive Disorder-tics (Cruz, C. et al., Increased prevalence of the seven-repeat variant of the dopamine D$_4$ receptor gene in patients with obsessive-compulsive disorder with tics. Neurosci. Lett. 1997, 231, 1. Van Tol, H. H. M. (1995) Clin Neuropharmacol. 18: S143–153).

One of the most remarkable polymorphisms in the human dopamine D$_4$ receptor is a variable number of 48 bp tandem repeats in the third cytoplasmic loop. Individuals with 2–10 tandem repeat units have been identified. Interestingly, this polymorphism appears to be primate-specific and has not been observed in rodents suggesting that these polymorphisms are evolutionarily recent events (Asghari, V. et al., Dopamine D$_4$ receptor repeat: analysis of different native and mutant forms of the human and rat genes (1994) Mol. Pharm. 46: 364–373).

The human D$_4$ receptor with seven repeat units has a number of unique characteristics which distinguish it from the other D$_4$ polymorphisms. This D4.7 variant has displayed a two- to threefold lower potency for the endogenous ligand dopamine than did the D4.2 variant (EC$_{50}$=40 nM vs. 15 nM) however, the functional implications of this lower affinity are not yet resolved.

Attention Deficit Hyperactivity Disorder (Hereinafter ADHD)

Attention deficit hyperactivity disorder (ADHD) is a disease which affects 3–5% of school age children. It is highly prevalent, making up to 50% of child psychiatry populations. The disease can also persist into adulthood, affecting 1–3% of adults. The diagnosis of ADHD revolve around three basic criteria: inattention, hyperactivity, and impulsivity. Approximately 50–70% of school-age children with the diagnosis of ADHD continue to manifest symptoms through middle adolescence, and almost one third will show some signs of the disorder in adulthood.

It has been shown that dopamine D$_4$ receptor gene polymorphism is associated with ADHD. Patients suffering from ADHD had a significant increase in the prevalence of 7-fold repeat form of the D$_4$ receptor, a variant which is unique for primates (LaHoste, G. J.; Swanson, J. M.; Wigal, S. B.; Glabe, C.; Wigal, T.; King, N.; Kennedy, J. L.; Dopamine D$_4$ receptor gene polymorphism is associated with attention deficit hyperactivity disorder. Mol. Psychiatry 1996, 1, 121). Interestingly, an excess of the D4.7 allele has also been associated with the personality trait of "novelty-seeking"; individuals scoring higher than average on this scale are characterized as impulsive, exploratory, fickle, excitable, quick-tempered and extravagant (Ebstein, R. P. et al.; Dopamine D$_4$ receptor (D$_4$DR) exon III polymorphism associated with the human personality trait of Novelty Seeking. Nature Genetics. 1996, 12, 78 and Benjamin, J. et al.; Population and familial association between the D$_4$ dopamine receptor gene and measures of Novelty Seeking. Nature Genetics. 1996, 12, 81).

This variant of the D$_4$ receptor may have a dysregulated response to dopamine, perhaps suggesting a gain of function for this receptor a) Van Tol, H. H. M.; Wu, C. M.; Guan, H—C.; Ohara, K.; Bunzow, J. R.; Civelli, O.; Kennedy, J.; Seeman, P.; Niznik, H. B.; Jovanovic, V.; Multiple dopamine D$_4$ receptor variants in the human population. Nature 1992, 352, 149, b) Van Tol, H. H. M.; Structural and Functional characteristics of the Dopamine D$_4$ Receptor. In Catecholamines Bridging Basic Science with Clinical Medicine. Goldstein, D. S.; Eisenhofer, G.; McCarty, R., Eds.; Academic Press: New York, 1997). Therefore, these data suggest that a D$_4$ antagonist may be efficacious in the treatment of ADHD without the side effect liability seen with current drug therapies.

Patients with ADHD also have markedly increased incidence of Conduct Disorder and Oppositional Defiant Disorder. Conduct Disorder is a disorder wherein the patient exhibits a repetitive and persistent pattern of behavior in which the basic rights of others or major age-appropriate societal norms or rules are violated. These behaviors fall into four main groupings: aggressive conduct that causes or threatens physical harm to other people or animals, nonaggressive conduct that causes property loss or damage, deceitfulness or theft, and serious violations of rules. Oppositional Defiant Disorder is a disorder wherein the patient exhibits some of the patterns of behavior observed in Conduct Disorder (e.g., disobedience and opposition to authority figures), however it does not include the persistent pattern of the more serious forms of behavior in which either the basic rights of others or age-appropriate societal norms or rules are violated. Although children with ADHD often exhibit hyperactive and impulsive behavior that may be disruptive, this behavior does not by itself violate age-appropriate societal norms and therefore does not usually meet criteria for Conduct Disorder. No specific data regarding gene frequency is available for these conditions, which are relatively refractory to available pharmacotherapy. If abnormalities of the $D_4$ neurotransmission involved in the pathogenesis of ADHD, it would be likely that $D_4$ abnormalities would also play a role in these conditions.

Obsessive-Compulsive Disorder (Hereinafter OCD)

Obsessive-compulsive disorder is a neurosis characterized by the presence of recurrent ideas and fantasies (obsessions) and repetitive impulses or actions (compulsions) that patients recognize as morbid and toward which they feel a strong inner resistance. In the US it is estimated that approximately four million patients are afflicted with OCD; however, fewer than half are diagnosed and treated.

The same seven-repeat variant of the dopamine $D_4$ receptor gene has been found to show increased prevalence in patients suffering from obsessive-compulsive disorder with tics (Cruz, C. et al., Increased prevalence of the seven-repeat variant of the dopamine $D_4$ receptor gene in patients with obsessive-compulsive disorder with tics. Neurosci. Lett. 1997, 231, 1. Van Tol, H. H. M. (1995) Clin Neuropharmacol. 18: S143–153). It has also been reported that adolescents with OCD plus tics are more prone to show violent and aggressive obsessions than those without tics (Cruz, C. et al., Increased prevalence of the seven-repeat variant of the dopamine $D_4$ receptor gene in patients with obsessive-compulsive disorder with tics. Neurosci. Let. 1997, 231, 1. Van Tol, H. H. M. (1995) Clin Neuropharmacol. 18: S143–153). As mentioned before, this $D_4$ variant has been shown to have a dysregulated response to dopamine. Thus OCD may also be a disorder associated with a gain of function at the $D_4$ receptor, which would respond to treatment with selective $D_4$ antagonists.

Schizophrenia

Schizophrenia is a severe mental illness affecting an estimated 1% of the world's population. The disease has an uncertain pathophysiology possibly leading to disruption of dopaminergic neural systems through poorly understood interactions of atomic, metabolic and genetic abnormalities. The schizophrenic patient suffers from psychotic symptoms broadly categorized as positive, negative or cognitive. The positive symptoms include delusions, hallucinations, irrational fears, and disorganization of thought. Negative or deficit symptoms include social withdrawal, impairment in role functioning, diminished or inappropriate affect, poverty of speech, marked lack of initiative or energy and the inability to experience pleasure. Cognitive symptoms comprise impairment of attention, verbal fluency, recall memory or executive function. Since the discovery of the clinical antipsychotic activity of chlorpromazine in the 1950s, the pharmacological antagonism of central dopamine receptors remains the only proven means for treating schizophrenia. This is evidenced by the number of agents with varied chemical structures that have been found to share the property of dopamine $D_2$ receptor antagonism and to have clinical benefit.

Recently using molecular biological techniques two families of dopamine receptors have been discovered namely the dopamine $D_1$ family ($D_1$ and $D_5$ receptor subtype) and the dopamine $D_2$ family ($D_2$, $D_3$, and $D_4$ receptor subtype). All clinically effective antipsychotic agents have been shown to bind to these receptor subtypes with varying affinities (Corbett, R. et al., 1997; Iloperidone: Preclinical Profile and early clinical evaluation. CNS Drugs Reviews 3(2): 120–147). A number of the recently introduced antipsychotic drugs with a profile for reduced extrapyramidal side effect liability have been shown to have greater affinity for the dopamine $D_4$ receptor subtype when compared to the dopamine $D_2$ receptor subtype. This greater affinity for the $D_4$ receptor compared to the $D_2$ receptor may contribute to these drugs having greater efficacy and less side effect liability than the traditional typical antipsychotic drugs (Seeman, P., Corbett, R. and Van Tol H. H. M. (1997) Atypical neuroleptics have low affinity for dopamine $D_2$ receptors or are selective for $D_4$ receptors. Neuropsychopharmacology 16 (2): 93–135.). Therefore, compounds with selective $D_4$ affinity may have efficacy against schizophrenia without causing the side effects associated with $D_2$ receptor blockade.

Substance Abuse/Substance Dependence

Repeated administration of psychostimulants such as d-amphetamine to rodents produces a progressive and long-lasting increase in behaviors such as locomotor activity, a phenomenon known as "behavioral sensitization" or "reverse tolerance". This enduring hypersensitivity to psychostimulants is also observed in humans and is thought to underlie drug addiction (Robinson, T. E. and Berridge, K. C. 1993 The neural basis of drug craving: an incentive sensitization theory of addiction Brain Research Reviews 18: 247–291). The mesolimbic dopamine system plays a critical role in the development of drug addiction. The development of behavioral sensitization to amphetamine is thought to reflect neuroadaptive biochemical and genomic responses triggered by the first exposure to the psychostimulant. Postsynaptic neuroplasticity results in alterations in dopamine receptor number and sensitivity. The function of the dopamine $D_2$ receptor family ($D_2$, $D_3$, and $D_4$ receptor subtypes) are all altered by the administration of amphetamine. The chronic administration of a selective dopamine $D_4$ receptor antagonist to rodents has been demonstrated to stop the development of behavioral sensitization to the administration of d-amphetamine indicating that selective dopamine $D_4$ antagonists may have efficacy for the treatment of drug abuse (Feldpausch D. L et al., 1998 The role of Dopamine $D_4$ receptor in the induction of behavioral sensitization to amphetamine and accompanying biochemical and molecular adaptations. Journal of Pharmacology and Experimental Therapeutics 266: 497–508).

A role for the $D_4$ receptor in substance abuse and substance dependence is supported by reports of an excess of long alleles (chiefly 7-repeat) of the $D_4$ exon 3 polymorphism in opiate and possibly alcohol abusers (Ebstein R P, Belmaker R H. 1997 Saga of an adventure gene: novelty seeking, substance abuse and the dopamine $D_4$ receptor ($D_4$DR) exon III repeat polymorphism. Mol Psychiatr 2:381–4; Kotler M, Cohen H, Segman R, et al. 1997 Excess dopamine $D_4$ receptor ($D_4$DR) exon III seven repeat allele in opioid-dependent subjects. Mol Psychiatr 2:251–4; Mel H, Horowitz R, Ohel N, et al. 1998 Additional evidence for an association between the dopamine $D_4$ receptor ($D_4$DR) exon III seven-repeat allele and substance abuse in opioid dependent subjects: Relationship of treatment retention to genotype and personality. Addiction Biology 3:473–81). Long alleles of the $D_4$ exon 3 polymorphism may also be associated with increased difficulty in quitting smoking, which may be related to nicotine addiction (Shields P G, Lerman C, Audrain J, et al. 1998 Dopamine $D_4$ receptors and the risk of cigarette smoking in African-Americans and Caucasians. Cancer Epidemiology, Biomarkers & Prevention 7:453–8).

Parkinson's Disease/Parkinsonism

Parkinson's disease is a progressive disorder of movement, characterized by tremor, rigidity, and bradykinesia. Other manifestations include depression, dementia (especially in advanced disease), and psychosis (especially as a complication of dopaminergic therapy). Parkinson's disease affects approximately 0.1% of the population, usually beginning after age 50. The major pathology is loss of dopaminergic neurons of the zona compacta in the substantia nigra. The major treatment is administration of dopamine precursors or agonists, but these are incompletely effective and are associated with side effects including dyskinesias, psychosis, and hypotension. Anticholinergic drugs are occasionally used, but are of limited efficacy and poorly tolerated.

Traditional antipsychotic drugs (neuroleptics) block the dopamine $D_2$ receptor and commonly produce symptoms of Parkinson's disease "Parkinsonism" in a dose-dependent manner corresponding to the potency of their $D_2$-blockade.

Dopamine synthesis in mouse dorsal striatum is increased in $D_4$ knockout mice (Rubinstein M, Phillips T J, Bunzow J R, et al. 1997 Mice lacking dopamine $D_4$ receptors are supersensitive to ethanol, cocaine, and methamphetamine. Cell 90:991–1001.). This suggests that a $D_4$ antagonist might have efficacy in treating Parkinson's disease, both in the treatment of the primary symptoms and in the treatment of both psychiatric and movement side-effects of standard dopaminergic therapies.

Several studies have suggested benefit of the atypical antipsychotic clozapine not only for treatment levodopa induced psychosis, but also for treatment of Parkinsonian symptoms themselves, especially tremor. These findings were reviewed by Factor and Friedman (Factor S A, Friedman J H. 1997 The emerging role of clozapine in the treatment of movement disorders. Movement Disorders 12:483–96). Clozapine, in addition to prominent $D_4$ blockade, has activity at multiple other receptors, notably serotonin 5-$HT_2$ and acetylcholine muscarinic. It is unlikely that anticholinergic effects account for clozapine's efficacy, as anticholinergic non-responders have responded dramatically to clozapine. While this may be due in part to 5-$HT_2$ antagonism; replacement of clozapine by olanzapine, a potent antagonist of 5-$HT_2$ (albeit with greater dopamine $D_2$ affinity than clozapine), was associated with increased Parkinsonian symptoms in a study of patients with Parkinson's disease (Friedman J H, Goldstein S, Jacques C. 1998 Substituting clozapine for olanzapine in psychiatrically stable parkinson's disease patients: Results of an open label pilot study. Clin Neuropharmacol 21:285–8). Dyskinesias and dystonia, associated with the use of levodopa, have also been reported to improve with clozapine (Factor S A, Friedman J H. 1997 The emerging role of clozapine in the treatment of movement disorders. Movement Disorders 12:483–96).

Further support for the potential role of the $D_4$ receptor in Parkinson's disease comes from a report of increased incidence of long ($\geq 6$ repeats) alleles of the $D_4$ exon 3 polymorphism in Parkinson's disease (Ricketts M H, Hamer R M, Manowitz P, et al. 1998 Association of long variants of the dopamine $D_4$ receptor exon 3 repeat polymorphism with Parkinsons-disease. Clinical Genetics 54:33–8).

Tardive Dyskinesia (Hereinafter TD)

Tardive dyskinesia is a movement disorder, consisting of involuntary choreiform, athetoid, or rhythmic movements of the tongue, jaw or extremities which develops as a result of (usually chronic) administration of neuroleptics and typically persists even after these drugs are discontinued. The overall prevalence of Neuroleptic-Induced Tardive Dyskinesia in patients who have received long-term neuroleptic treatment is estimated at 20–30% (American Psychiatric Association. Diagnostic and Statistical Manual of Mental Disorders, Fourth edition. Washington, D.C., American Psychiatric Association, 1994).

Increased concentrations of $D_4$ receptor have been reported in some postmortem studies of schizophrenics (usually treated for extended periods with traditional neuroleptics) (Lahti R A, Roberts R C, Cochrane E V, et al. 1998 Direct determination of dopamine $D_4$ receptors in normal and schizophrenic postmortem brain tissue: A ($^3$H)NGD-94-1 study. Mol Psychiatr 3:528–33; Seeman P, Guan H C, Van Tol H H. 1995 Schizophrenia: elevation of dopamine $D_4$-like sites, using [$^3$H]nemonapride and [$^{125}$I]epidepride. Eur J Pharmacol 286:R3–5). An up-regulation of the $D_2$ receptor has been seen with chronic administration of the neuroleptic haloperidol in both animal and human studies (Schroder J, Silvestri S, Bubeck B, et al. 1998 $D_2$ dopamine receptor up-regulation, treatment response, neurological soft signs, and extrapyramidal side effects in schizophrenia: a follow-up study with $^{123}$I-iodobenzamide single photon emission computed tomography in the drug-naive state and after neuroleptic treatment. Biol Psychiatry 43:660–5). Use of these drugs might also be responsible for up-regulation of the $D_4$ receptor.

Improvement in TD has been seen with clozapine (Bassitt D P, Louza-Neto M R. 1998 Clozapine efficacy in tardive dyskinesia in schizophrenic patients. European Archives of Psychiatry & Clinical Neuroscience 248:209–11) a drug with prominent $D_4$ antagonism. While clozapine has other pharmacologic actions, notably 5$HT_2$ receptor blockade, an effect on T.D. has not to date been established for 5$HT_2$/$D_2$ receptor antagonists such as risperidone or olanzapine. The concern might be raised that chronic $D_4$ blockade might also cause tardive dyskinesia, however this complication has been exceedingly rare in patients treated with clozapine.

Gilles de la Tourette Syndrome (Hereinafter TS)

Gilles de la Tourette syndrome, a condition manifest by motor and vocal tics, with a prevalence of approximately 0.5% (most common in adolescents), is seen with increased frequency in patients with ADHD and/or OCD, and in family members of patients with those conditions. Use of stimulant drugs (which increase synaptic dopamine concentrations) in patients with ADHD has been associated with an increased incidence of tics and possibly TS (Erenberg G, Cruse R P, Rothner A D. 1985 Gille de la Tourette's syndrome: Effects of stimulant drugs. Neurology 35:1346–8). An increased incidence of the D4.7 allele has been reported in TS (Grice D E, Leckman J F, Pauls D L, et al. 1996 Linkage disequilibrium between an allele at the dopamine $D_4$ receptor locus and Tourette syndrome, by the transmission-disequilibrium test. American Journal of Human Genetics 59:644–52), and haloperidol (a $D_2/D_4$ dopamine antagonist) is effective at controlling tics.

SUMMARY OF THE INVENTION

According to one aspect of the present invention, there is provided a compound of formula I:

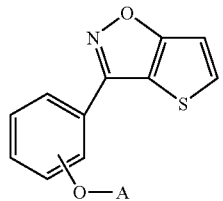

Formula I a pharmaceutically acceptable salt or stereoisomer thereof, wherein

A is $C_{2-3}$ alkylene-N(R$_1$)(R$_2$) or 1-(phenylmethyl)-pyrrolidin-3-yl;

R$_1$ is (CH$_2$)$_n$Q, CH$_2$CH(OH)Q, CH(CH$_3$)Q, 1,2,3,4-tetrahydronaphthyl, indanyl, or adamantyl, wherein Q is thienyl, phenyl, furanyl, naphthyl, pyridyl, indolyl, indazolyl, cyclohexyl, 1,2-methylenedioxyphenyl, cyclohexenyl, 1H-pyrazolo[4,3-c]pyridyl; and Q is optionally substituted with one or two moieties independently selected from halo, $C_{1-6}$ alkyl, $C_{1-6}$ alkoxy, hydroxy, S(O)$_2$NH$_2$, trifluoromethyl, or cyano, and n is 1 or 2;

R$_2$ is H or $C_{1-6}$ alkyl; or

R$_1$ and R$_2$, together with the nitrogen atom to which R$_1$ and R$_2$ are attached, form 4,5,6,7-tetrahydrothieno[3,2-c] pyridinyl, 1,4-dioxa-8-azo-spiro[4.5]decanyl, piperazinyl, morpholinyl, piperidinyl, pyrrolidinyl, azocanyl, azepanyl, 1,2,3,4-tetrahydroisoquinolinyl, 1,2,3,4-tetrahydro-1H-β-carbolinyl, or 8-aza-bicyclo[3.2.1.]octanyl, each of which may be mono- or independently di-substituted with halo, $C_{1-6}$ alkyl, $C_{1-6}$ alkoxy, C(O)phenyl, OH, CN, O-phenyl or (CH$_2$)$_m$Z, Z is benzisoxazolyl, indazolyl, benzisothiazolyl, benzthienyl, pyrimidinyl, pyridyl, 1,2-methylenedioxyphenyl, or phenyl, and Z, CH(OH)phenyl or O-phenyl are optionally substituted with one or two moieties independently selected from halo, $C_{1-6}$ alkyl, $C_{1-6}$ alkoxy, hydroxy, trifluoromethyl, S(O)$_2$NH$_2$, or cyano, and m is 0 or 1.

Another aspect of the invention is to provide a pharmaceutical composition comprising a compound of formula I in an amount effective to antagonize $D_4$ receptor stimulation and a pharmaceutically acceptable carrier.

In yet another of its aspects, the invention provides the use of compounds of Formulas I as $D_4$ receptor antagonists for the treatment of medical conditions mediated by inhibition of $D_4$ receptor. These conditions comprise, for example, Attention Deficit Hyperactivity Disorder, Obsessive-Compulsive Disorder, Psychoses, Substance Abuse, Substance Dependence, Parkinson's Disease, Parkinsonism, Tardive Diskinesia, Gilles de la Tourette Syndrome, Conduct Disorder, and Oppositional Defiant Disorder.

A further aspect of the invention is to provide intermediates and a method of making compounds of the formula I.

DETAILED DESCRIPTION OF THE PRESENT INVENTION

Terms used herein have the following meanings:

a) "Pharmaceutically acceptable salts" means either an acid addition salt or a basic addition salt which is compatible with the treatment of patients for the intended use.

"Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methanesulfonic acid, naphthalene sulfonic acid, and 2-hydroxyethanesulfonic acid. Either the mono- or di-acid salts can be formed, and such salts can exist in either a hydrated. solvated or substantially anhydrous form. In general, the acid addition salts of these compounds are more soluble in water and various hydrophilic organic solvents. Furthermore, in comparison to their free base forms, the acid addition salts generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection criteria for the appropriate salt will be known to one skilled in the art.

b) "Stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

c) "Alkyl" as used herein means a branched or straight chain alkyl (monovalent) or alkylene (divalent) hydrocarbon radical, as is appropriate to the formula, specified by the amount of carbons in the alkyl, e.g., $C_{1-6}$ alkyl means a one, two, three, four, five or six carbon branched or straight chain alkyl or alkylene, as the case may be, or any ranges thereof, for example, but not limited to $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, $C_{5-6}$, etc.

d) "Patient" means a warm blooded animal, such as for example rat, mice, dogs, cats, guinea pigs, and primates such as humans.

e) "Treat" or "treating" means to alleviate symptoms, eliminate the causation of the symptoms either on a temporary or permanent basis, or to prevent or slow the appearance of symptoms of the named disorder or condition.

f) "Therapeutically effective amount" means a quantity of the compound which is effective in treating the named disorder or condition.
g) "Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.
h) "Psychoses" means conditions wherein the patient experiences a major mental disorder of organic and/or emotional origin characterized by derangement of the personality and loss of contact with reality, often with delusions, halucinations or illusions. Representative examples of psychotic illnesses include schizophrenia, schizophreniform disorder, schizoaffective disorder, delusional disorder, brief psychotic disorder, shared psychotic disorder, psychotic disorder not otherwise specified, and substance-induced psychotic disorder. See Diagnostic and Statistical Manual of Mental Disorders, 4th ed., American Psychiatric Association, incorporated herein by reference.
i) "Attention-Deficit/Hyperactivity Disorder" or "ADHD" means a condition wherein the patient exhibits a persistent pattern of inattention and/or hyperactivity-impulsivity that is more frequent and severe than is typically observed in individuals at a comparable level of development. It includes ADHD Combined Type, ADHD Predominantly Inattentive Type, and ADHD Predominantly hyperactive-impulsive Type.
j) "Conduct Disorder" means a disorder wherein the patient exhibits a repetitive and persistent pattern of behavior in which the basic rights of others or major age-appropriate societal norms or rules are violated. These behaviors fall into four main groupings: aggressive conduct that causes or threatens physical harm to other people or animals, nonaggressive conduct that causes property loss or damage, deceitfulness or theft, and serious violations of rules.
k) "Oppositional Defiant Disorder" means a disorder wherein the patient exhibits some of the patterns of behavior observed in Conduct Disorder (e.g., disobedience and opposition to authority figures), however it does not include the persistent pattern of the more serious forms of behavior in which either the basic rights of others or age-appropriate societal norms or rules are violated.
l) "Obsessive-Compulsive Disorder" or "OCD" means a condition wherein the patient exhibits recurrent obsessions or compulsions that are severe enough to be time consuming (i.e., take more than an hour a day) or cause marked distress or significant impairment. Obsessions are persistent ideas, thoughts, impulses, or images that are experienced as intrusive and inappropriate and that cause marked anxiety or distress. Compulsions are repetitive behaviors (e.g, hand washing, ordering, checking) or mental acts (e.g., praying, counting, repeating words silently) the goal of which is to prevent or reduce anxiety or distress, not to provide pleasure or gratification.
m) "Substance Dependence" means a condition wherein the patient exhibits a maladaptive pattern of substance use, leading to clinically significant impairment or distress. There is a pattern of repeated self-administration that usually results in tolerance, withdrawal, and compulsive drug-taking.
n) "Substance Abuse" means a condition wherein the patient exhibits a maladaptive pattern of substance use manifested by recurrent and significant adverse consequences related to the repeated use of substances. There may be repeated failure to fulfill major role obligations, repeated use in situations in which it is physically hazardous, multiple legal problems, and recurrent social and interpersonal problems. Unlike the criteria for Substance Dependence, the criteria for Substance Abuse do not include tolerance, withdrawal, or a pattern of compulsive use and instead only include the harmful consequences of repeated use.
o) "Parkinson's Disease" means a slowly progressive neurological condition, characterized by tremor, rigidity, bradykinesia, and postural instability. Other manifestations include depression and dementia.
p) "Parkinsonism" means a condition where the patient exhibits parkinsonian signs or symptoms (i.e. tremor, muscular rigidity, or akinesia) that develop in association with the use of neuroleptic medication.
q) "Neuroleptic-Induced Tardive Dyskinesia" means a disorder characterized by involuntary movements of the tongue, jaw, trunk, or extremities which have developed in association with the use of neuroleptic medication. The involuntary movements may be choreiform, athetoid or rhythmic.
r) "Gilles de la Tourette Syndrome" means a condition manifested by motor and vocal tics. (A tic is a sudden, rapid, recurrent, nonrhythmic, stereotyped motor movement or vocalization.) The disturbance causes marked distress or significant impairment in social, occupational, or other important areas of functioning. The onset is before age eighteen years and the disturbance is not due to the physiological effects of a substance or general medical condition.
s) Unless otherwise specified, "halo" or "halogen" means Cl, Br, F and I.
t) "Aryl sulfonyl" means the radical:

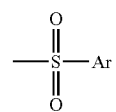

wherein Ar is phenyl optionally substituted one or more moieties from the group consisting of halogen, nitro, or $C_1$–$C_6$alkyl. "Brosyl" means the radical wherein Ar is p-bromobenzene. "Nosyl" means the radical wherein Ar is p-nitrobenzene. "Tosyl" means the radical wherein Ar is p-toluene.

"Alkyl sulfonyl" Means the Radical:

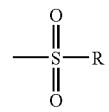

wherein R is $C_1$–$C_6$alkyl. "Mesyl" means the radical wherein R is $CH_3$.

u) "Sulfonic ester" means the radical:

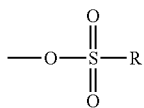

wherein R is $C_1$–$C_6$alkyl or phenyl optionally substituted with one or more moieties from the group consisting of halogen, nitro, or $C_1$–$C_6$alkyl. "Sulfonic esters" are, for example, brosylate, nosylate, tosylate, and mesylate.

v) "Parallel Synthesis" is a term used to describe the simultaneous synthesis of tens to millions of compounds in solution or on a solid phase. The key characteristic that distinguishes this approach from serial techniques is that it does not utilize mixtures.

As used herein, the terms used to describe specific chemical moieties are defined by the corresponding chemical drawings which are set forth on the following page:

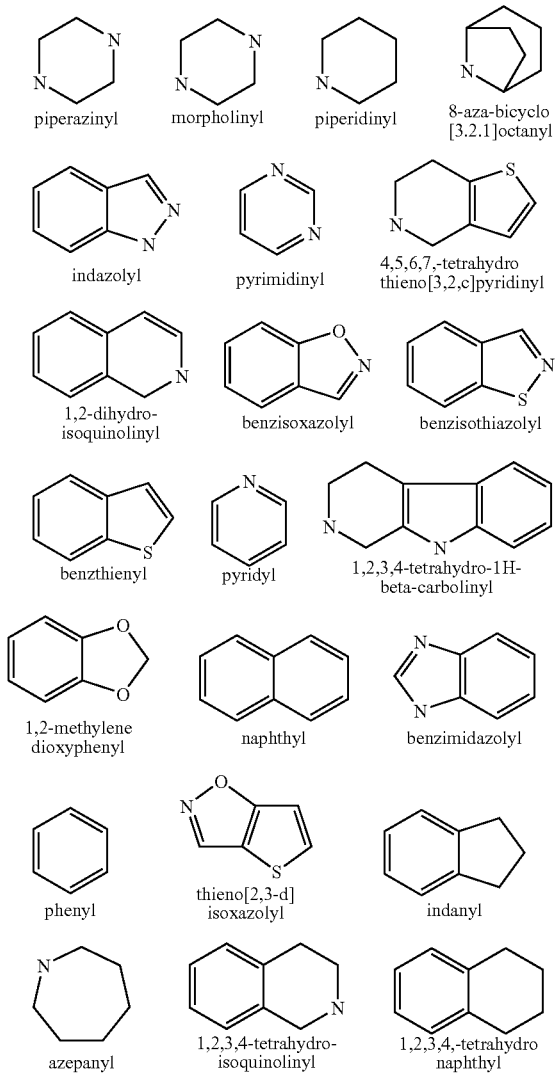

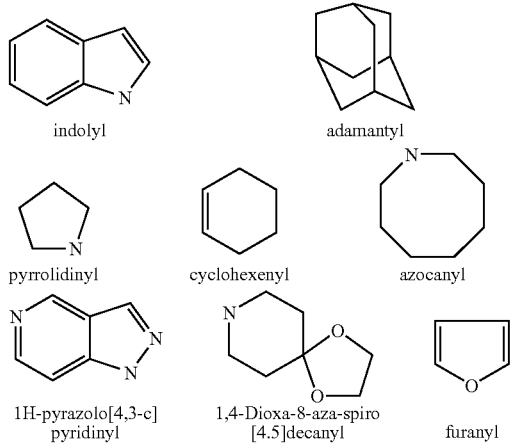

Specific embodiments of the invention are those compounds of Formula I set forth in Table 1.

A preferred embodiment of the invention is the compound according to Formula I wherein $R_1$ and $R_2$ together with the nitrogen atom to which $R_1$ and $R_2$ are attached, form piperazinyl, 1,2,3,4-tetrahydroisoquinolinyl, or azepanyl.

Another preferred embodiment of the invention is the compound according to Formula I wherein $R_1$ is adamantyl.

Another preferred embodiment of the invention is the compound according to Formula I wherein $R_1$ is indanyl.

Another preferred embodiment of the invention is the compound according to Formula I wherein A is 1-(phenylmethyl)-pyrrolidin-3-yl.

A more preferred embodiment of the invention is the compound according to Formula I wherein Q is thienyl, phenyl, or pyridyl; or $R_1$ and $R_2$, together with the nitrogen atom to which $R_1$ and $R_2$ are attached, form morpholinyl, piperidinyl, pyrrolidinyl, or azocanyl.

An even more preferred embodiment of the invention is a compound of Formula I wherein A is $C_{2-3}$alkylene-N($R_1$)($R_2$); $R_1$ is $(CH_2)_nQ$; n is 1; $R_2$ is H; Q is thienyl, phenyl, or pyridyl, or $R_1$ and $R_2$, together with the nitrogen atom to which $R_1$ and $R_2$ are attached, form morpholinyl, piperidinyl, pyrrolidinyl, or azocanyl.

Most preferred embodiments of the invention are those compounds of Formula I set forth in Table 1 that exhibit enhanced $D_4$ potency.

Acid addition salts of the compound of Formula I are most suitably formed from pharmaceutically acceptable acids, and include for example those formed with inorganic acids, e.g. hydrochloric, sulphuric, or phosphoric acids, and organic acids, e.g. succinic, maleic, acetic or fumaric acid. Other non-pharmaceutically acceptable salts, e.g. oxalates, may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base, e.g. sodium carbonate or potassium hydroxide, to liberate the free base which is then extracted into an appropriate solvent, such as ether. The free base is then separated from the aqueous portion, dried, and treated with the requisite acid to give the desired salt.

The compounds of the present invention can be prepared by processes analogous to those known in the art. Schemes I, Ia, Ib and II illustrate methods for the synthesis of compounds of Formula I.

Where no synthesis for the starting material is indicated, the starting material is either known, available commercially, or can be prepared by conventional means. The United States patents cited in the specification are herein incorporated by reference.

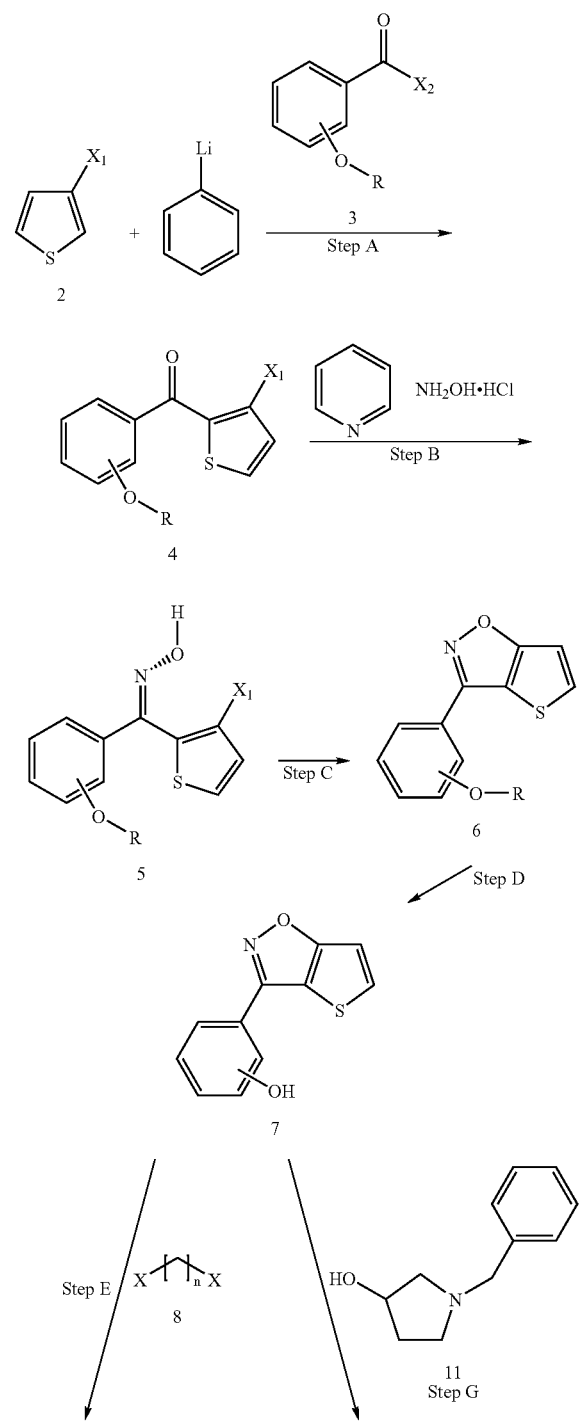

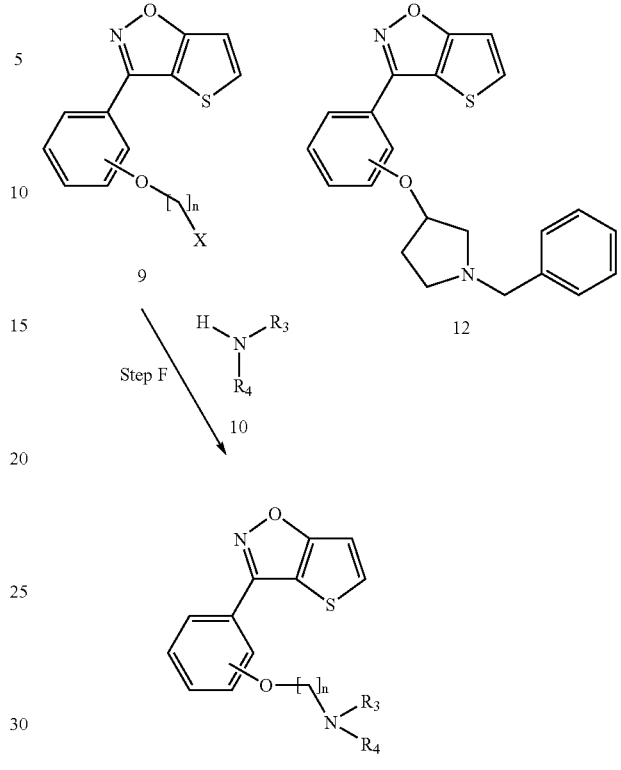

X is each independently Br, Cl or I; $X_1$ is halo, preferably Br; $X_2$ is Br, Cl or I, preferably Cl; n is 2 or 3; R is $C_1$-$C_6$ alkyl; $R_3$ is $(CH_2)_yQ$, $CH_2CH(OH)Q$, $CH(CH_3)Q$, indanyl, 1,2,3,4-tetrahydronaphthyl, or adamantyl, wherein Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and Q is optionally substituted with one or two moieties independently selected from halo, $C_1$-$C_6$ alkyl, $C_1$-$C_6$ alkoxy, hydroxy, $S(O)_2NH_2$, trifluoromethyl, or cyano, and y is 1 or 2;

$R_4$ is H or $C_1$-$C_6$ alkyl; or $R_3$ and $R_4$, together with the nitrogen atom to which $R_3$ and $R_4$ are attached, form 4,5,6,7-tetrahydrothieno[3.2.c]pyridinyl, 1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-beta-carbolinyl, or 8-aza-bicyclo[3.2.1]octanyl, each of which may be mono- or independently di-substituted with halo, $C_1$-$C_6$ alkyl, $C_1$-$C_6$ alkoxy, C(O)phenyl, OH, CN, O-phenyl or $(CH_2)_mZ$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl or O-phenyl are optionally substituted with one or two moieties independently selected from halo, $C_1$-$C_6$ alkyl, $C_1$-$C_6$ alkoxy, hydroxy, trifluoromethyl, $S(O)_2NH_2$ or cyano; m is 0 or 1.

Scheme I (a)

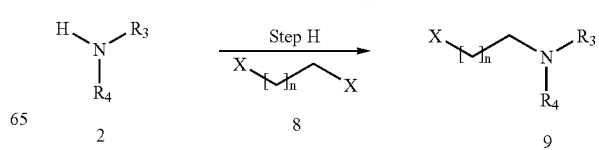

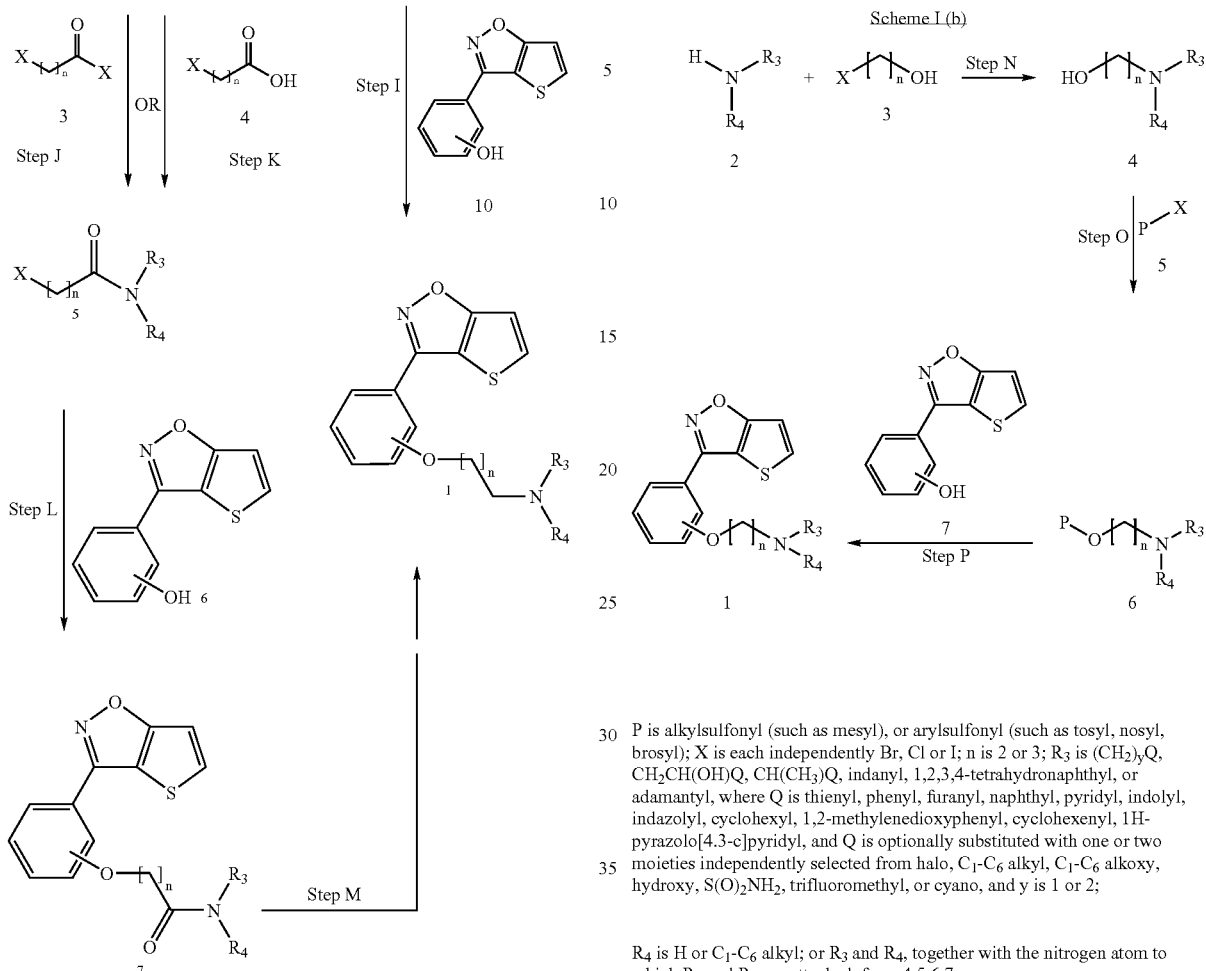

P is alkylsulfonyl (such as mesyl), or arylsulfonyl (such as tosyl, nosyl, brosyl); X is each independently Br, Cl or I; n is 2 or 3; R₃ is (CH₂)$_y$Q, CH₂CH(OH)Q, CH(CH₃)Q, indanyl, 1,2,3,4-tetrahydronaphthyl, or adamantyl, where Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and Q is optionally substituted with one or two moieties independently selected from halo, $C_1$-$C_6$ alkyl, $C_1$-$C_6$ alkoxy, hydroxy, S(O)₂NH₂, trifluoromethyl, or cyano, and y is 1 or 2;

R₄ is H or $C_1$-$C_6$ alkyl; or R₃ and R₄, together with the nitrogen atom to which R₃ and R₄ are attached, form 4,5,6,7-tetrahydrothieno[3.2.c]pyridinyl, 1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-beta-carbolinyl, or 8-aza-bicyclo[3.2.1]octanyl, each of which may be mono- or independently di-substituted with halo, $C_1$-$C_6$ alkyl, $C_1$-$C_6$ alkoxy, C(O)phenyl, OH, phenyl, CN, O-phenyl or (CH₂)$_m$Z, Z is benzisoxazolyl, indazolyl, benzisothiazolyl, benzthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, $C_1$-$C_6$ alkyl, $C_1$-$C_6$ alkoxy, hydroxy, trifluoromethyl, S(O)₂NH₂ or cyano; m is 0 or 1.

Scheme II

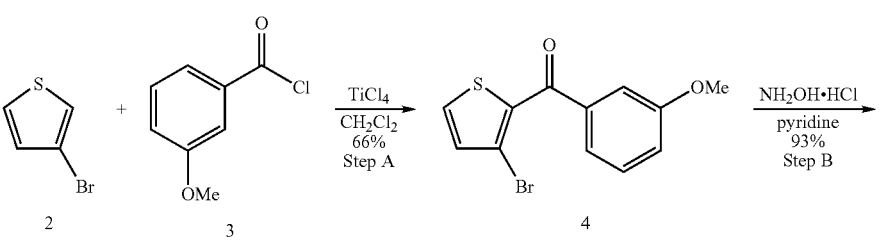

-continued
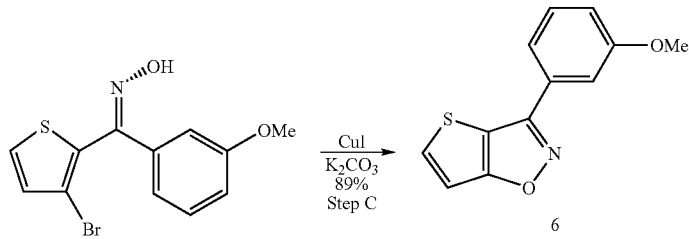
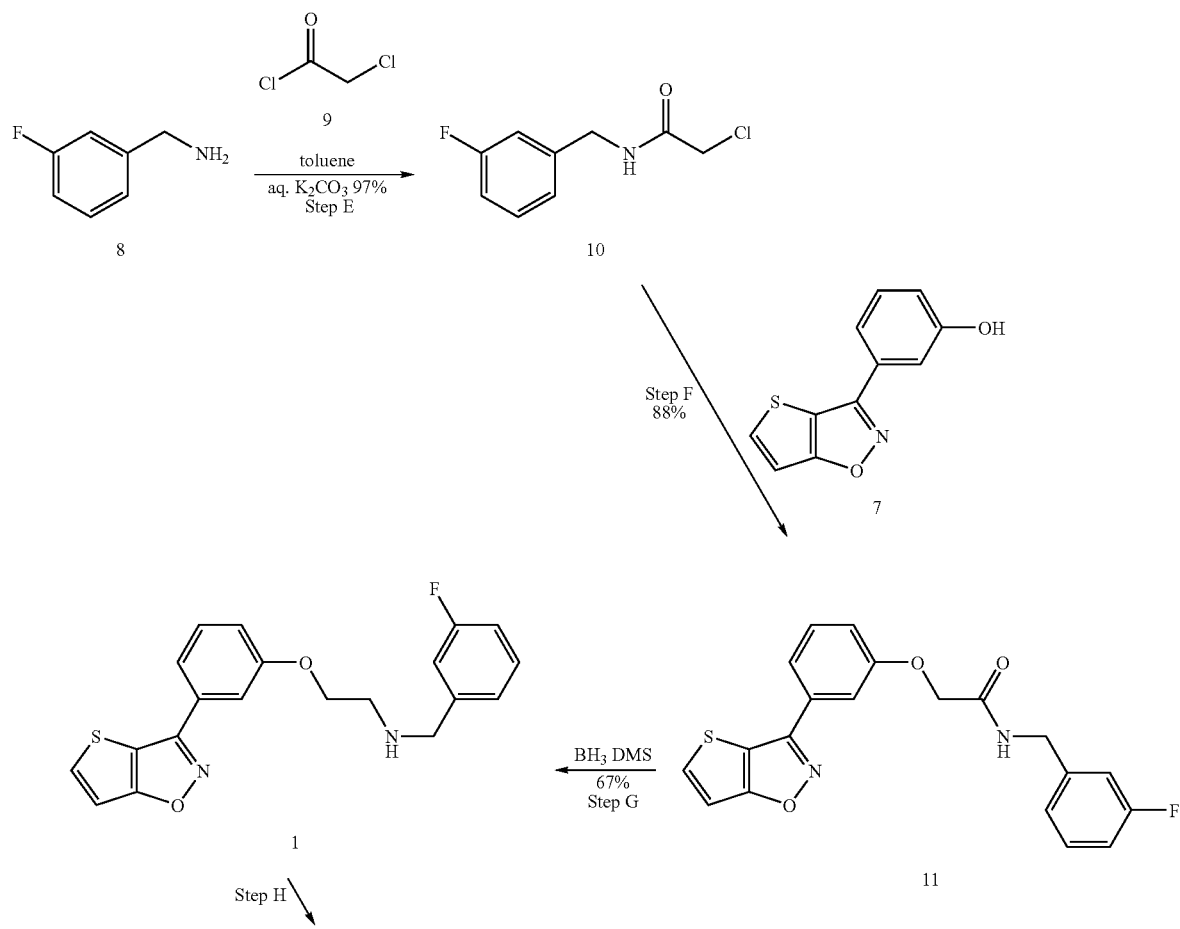
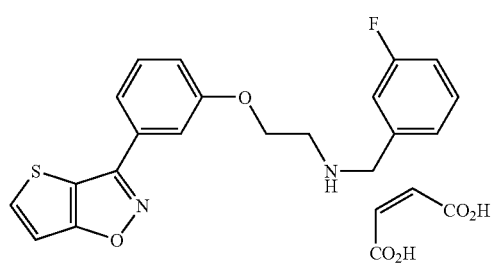

In Scheme I, Step A, the anion of the appropriately substituted thiophene of structure 2 can be acylated with the appropriate substituted acid halide of structure 3 to give the corresponding ketone of structure 4.

For example, the appropriate substituted thiophene of structure 2 can be metallated at 5° C., using for example, phenyl lithium or lithium diisopropyl amide, to form the anion. The anion can be acylated by reaction with the appropriate acid halide of structure 3. For example, the appropriate acid halide in a suitable aprotic solvent such as tetrahydrofuran is cooled to −70° C. The lithiated intermediate can then be added to the acid chloride, dropwise, over a period of time ranging from 1 to 3 hours. The resulting ketone of structure 4 may be isolated from the reaction mixture by extractive methods as is known in the art. Purification of the ketone of structure 4 may be done by alumina column chromatography eluting with a suitable solvent, such as hexane, or mixture of solvents, such as a mixture of ether and hexane. Further purification may be done by vacuum distillation and/or recrystallization.

In step B, the appropriate ketone of structure 4 and hydroxylamine hydrochloride are reacted to give the corresponding oxime of structure 5.

For example, the appropriate ketone of structure 4 and hydroxylamine hydrochloride, can be reacted in a suitable aprotic solvent, such as pyridine. This particular solvent may also act as the base of the reaction. The reactants are typically stirred together at room temperature overnight, followed by heating at a temperature of from about 100° C. to about 105° C. for a period of time ranging from 1 to 4 hours. The resulting oxime of structure 5 may be recovered from the reaction mixture by extractive methods as is known in the art. The crude oxime of structure 5 may then be purified by recrystallization.

In step C, the oxime of structure 5 is cyclized with the appropriate reagents to give the corresponding phenyl isoxazole of structure 6.

For example, the oxime of structure 5 can be treated with a suitable base, such as potassium hydroxide, catalyst, such as copper chloride, and protic solvent, such as 2-ethoxyethanol. The reactants are typically stirred and heated together at a temperature of from about 105° C. to about 110° C., under a nitrogen atmosphere, for a period of time ranging from 2 to 6 hours. The resulting isoxazole of structure 6 may be recovered from the reaction mixture by extractive methods as is known in the art. The crude phenyl isoxazole of structure 6 may then be purified by chromatography.

In step D, the phenyl isoxazole compound of structure 6 is dealkylated with the appropriate reagents to give the corresponding phenyl isoxazole compound of structure 7.

For example, the phenyl isoxazole of structure 6 can be treated with a suitable dealkylating reagent, such as boron tribromide. Other alternative reagents include pyridine hydrochloride or boron trichloride. The reactants are typically stirred and heated together at a temperature of from about 135° C. to about 140° C., under a nitrogen atmosphere, for a period of time ranging from 4 to 9 hours. The resulting phenyl isoxazole of structure 7 may be recovered from the reaction mixture by extractive methods as is known in the art. The crude phenyl isoxazole of structure 7 may then be purified by chromatography.

In step E, the appropriate phenyl isoxazole of structure 7 and the appropriate alkyl halide of structure 8 are reacted to give the corresponding halo alkoxy phenyl isoxazole of structure 9.

For example, the appropriate phenyl isoxazole of structure 7 and the appropriate alkyl halide of structure 8 can be reacted in the presence of potassium carbonate. The reactants are typically stirred together at reflux, under nitrogen, for a period of time ranging from 5 hours to overnight. The resulting halo alkoxy phenyl isoxazole of structure 9 may be recovered from the reaction mixture by extractive methods as is known in the art. The crude halo alkoxy phenyl isoxazole of structure 9 may then be purified by chromatography.

In step F, the appropriate halo alkoxy phenyl isoxazole of structure 9 and the appropriate amine of structure 10 are reacted to give the corresponding amino alkoxy phenyl isoxazole, of structure 1.

For example, the appropriate halo alkoxy phenyl isoxazole of structure 9 and the appropriate amine of structure 10 can be reacted in the presence of potassium carbonate in a suitable anhydrous, aprotic solvent, such as acetonitrile. The reactants are typically stirred and heated together at a temperature of from about 65° C. to about 80° C., under a nitrogen atomosphere, for a period of time ranging from 16.5 hours to 30 hours. The resulting amino alkoxy phenyl isoxazole of structure 1 may be recovered from the reaction mixture by extractive methods as is known in the art or more typically, the resulting amino alkoxy phenyl isoxazole of structure 1 is recovered by removal of solvent followed by charging directly onto a silica gel column and eluting with a suitable solvent or mixture of solvents. The crude amino alkoxy phenyl isoxazole of structure 1 may then be purified by chromatography, salt formation or recrystallization.

In step G, the appropriate phenyl isoxazole of structure 7 and the pyrrolidine of structure 11 are reacted to give the corresponding pyrrolidinyl oxy phenyl isoxazole of structure 12.

For example, the appropriate phenyl isoxazole of structure 7 and the pyrrolidine of structure 11 can be reacted in the presence of triphenylphosphine and diethyl azodicarboxylate in a suitable anhydrous, aprotic solvent, such as tetrahydrofuran. The reactants are typically stirred together at room temperature, under nitrogen, for a period of time ranging from 4 hours to overnight. The resulting pyrrolidinyl oxy phenyl isoxazole of structure 12 may be recovered from the reaction mixture by extractive methods as is known in the art. The crude pyrrolidinyl oxy phenyl isoxazole of structure 12, may then be purified by chromatography.

Alternatively, in Scheme I (a), Step H, the appropriate alkyl halide of structure 8 and the appropriate amine of structure 2 are reacted to form the halo alkyl amine of structure 9.

For example, the appropriate alkyl halide of structure 8 and the appropriate amine of structure 2 can be reacted in the presence of a base acceptable to one skilled in the art, such as fused sodium acetate. The reactants are typically stirred and heated together at reflux, for several hours. The resulting halo alkyl amine of structure 9 may be recovered from the reaction mixture by extractive methods as is known in the art. The crude halo alkyl amine of structure 9 may then be purified by distillation, chromatography or further extractive methods as is known in the art.

In Step I, the appropriate halo alkyl amine of structure 9 and the appropriate phenyl isoxazole of structure 10 are reacted to give the corresponding amino alkoxy phenyl isoxazole, of structure 1.

For example, the appropriate phenyl isoxazole of structure 10 can be reacted in the presence of sodium hydroxide in a suitable aprotic solvent, such as dichloromethane, to form the appropriate sodium salt of the phenyl isoxazole of structure 10. The appropriate sodium salt of structure 10 is then combined with the appropriate halo alkyl amine of structure 9 in a suitable aprotic solvent, such as toluene. The reactants are typically stirred and heated together at reflux, for a period of time of about 24 hours. The reaction mixture may then be cooled and filtered to recover the amino alkoxy phenyl isoxazole of structure 1. The crude alkoxy phenyl isoxazole of structure 1 may then be purified by chromatography, recrystallization or salt formation.

In Step J, the appropriate amine of structure 2 can be reacted with the appropriate compound of structure 3 to give the corresponding compound of structure 5 with conditions analogous to those as exemplified in Scheme II, Step E.

In Step K, as an alternative to Step J, the appropriate compound of structure 4 and the appropriate amine of structure 2 are reacted to give the corresponding compound of structure 5.

For example, the appropriate compound of structure 4 can be coupled with the appropriate amine of structure 2, in the presence of a suitable coupling reagent, such as 1,3-dicyclohexylcarbodiimide and a suitable aprotic, anhydrous solvent, such as dichloromethane. A suitable base, such as 1-hydroxybenzotriazole hydrate, may be required for use with certain coupling reagents. The reactants are typically stirred together for a period of time of about 2.0 hours, at temperatures ranging from $-35°$ C. to $-30°$ C. The crude compound of structure 5 may be recovered by methods as known to one skilled in the art.

In Step L, the appropriate compound of structure 5 can be reacted with the appropriate phenyl isoxazole of structure 6 to give the corresponding compound of structure 7 with conditions analogous to those as exemplified in Scheme II, Step F.

In Step M, the appropriate compound of structure 7 can be reduced by an appropriate reducing agent such as borane-tetrahydrofuran complex or borane-dimethylsulfide complex to give the corresponding alkoxy phenyl isoxazole of structure 1 with conditions analogous to those exemplified in Scheme II, Step G.

As a second alternative, in Scheme I (b), Step N, the appropriate amine of structure 2 and the appropriate halo alcohol of structure 3 are reacted to give the corresponding hydroxy alkyl amine of structure 4.

For example, the appropriate amine of structure 2 can be reacted in the presence of water, in a suitable protic solvent, such as 2-chloroethanol. The reactants are typically stirred and heated together for a period of time of ~5 hours. Typically, the mixture is cooled and then sodium hydroxide is added, followed by additional heating for ~30 minutes. The resulting hydroxy alkyl amine of structure 4 may be recovered from the reaction mixture by extractive methods as is known in the art. The water may be removed and the hydroxy alkyl amine of structure 4 may be purified by distillation or chromatography.

In Step O, the appropriate hydroxy alkyl amine of structure 4 and the appropriate sulfonate ester halide of structure 5 are reacted to give the corresponding sulfonate ester alkyl amine of structure 6. In the case where $R_4$=H, a protecting group on the amine may be required. See *Protective Groups in Organic Synthesis*, $2^{nd}$ ed., Theodora W. Greene, et al. John Wiley and Sons, Inc., incorporated herein by reference, for appropriate protecting groups.

For example, the appropriate hydroxy alkyl amine of structure 4 and the appropriate sulfonate ester halide of structure 5 can be reacted in the presence of triethylamine in a suitable aprotic solvent, such as dichloromethane. The reactants are typically stirred together at room temperature. The resulting sulfonate ester alkyl amine of structure 6 may be recovered from the reaction mixture by extractive methods as is known in the art. The crude sulfonate ester alkyl amine of structure 6 may then be purified by chromatography.

In Step P, the appropriate sulfonate ester alkyl amine of structure 6 and the appropriate phenyl isoxazole of structure 7 are reacted to give the corresponding amino alkoxy phenyl isoxazole of structure 1.

For example, the appropriate sulfonate ester alkyl amine of structure 6 and the appropriate phenyl isoxazole of structure 7 can be reacted in the presence of potassium carbonate in a suitable aprotic solvent, such as acetonitrile. The reactants are typically stirred and heated together at 75° C. overnight. The resulting amino alkoxy phenyl isoxazole of structure 1 may be recovered from the reaction mixture by extractive methods as is known in the art. The crude amino alkoxy phenyl isoxazole of structure 1 may be purified by chromatography, salt formation or recrystallization.

Starting materials for use in the general synthetic procedures outlined in Schemes I, I(a), I(b) and II are readily available to one of ordinary skill in the art, unless otherwise specified in the Examples section.

The $D_4$ binding profile of the present compounds indicates their utility as pharmaceuticals that may be useful as a neuroleptic for the treatment of various conditions in which $D_4$ receptor stimulation is implicated, such as for the treatment of anxiety and schizophrenia. Accordingly, in another of its aspects, the present invention provides pharmaceutical compositions useful to treat $D_4$-related medical conditions in which a compound of Formula I is present in an amount effective to antagonize $D_4$ receptor stimulation, together with a pharmaceutically acceptable carrier. In another of its aspects, the invention provides a method for treating medical conditions for which a $D_4$ antagonist is indicated, which comprises the step of administering to the patient an amount of a compound of Formula II effective to antagonize $D_4$ receptor stimulation, and a pharmaceutically acceptable carrier therefor.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate, or hydrate thereof, in an amount effective to antagonize $D_4$ receptor stimulation.

In treating a patient afflicted with a condition described above, a compound of formula (I) can be administered in any form or mode which makes the compound bioavailable in therapeutically effective amounts, including orally, sublingually, buccally, subcutaneously, intramuscularly, intravenously, transdermally, intranasally, rectally, topically, and the like. One skilled in the art of preparing formulations can determine the proper form and mode of administration depending upon the particular characteristics of the compound selected for the condition or disease to be treated, the stage of the disease, the condition of the patient and other relevant circumstances. For example, see Remington's Pharmaceutical Sciences, 18th Edition, Mack Publishing Co. (1990), incorporated herein by reference.

The compounds of Formula I can be administered alone or in the form of a pharmaceutical composition in combination with pharmaceutically acceptable carriers, the proportion and nature of which are determined by the solubility and chemical properties of the compound selected, the chosen route of administration, standard pharmaceutical practice and other relevant criteria.

The compounds of the present invention may be administered orally, for example, in the form of tablets, troches, capsules, elixirs, suspensions, solutions, syrups, wafers, chewing gums and the like and may contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors.

The compounds of Formula (I) of this invention may also be administered topically, and when done so the carrier may suitably comprise a solution, ointment or gel base. The base, for example, may comprise one or more of petrolatum, lanolin, polyethylene glycols, bee wax, mineral oil, diluents such as water and alcohol, and emulsifiers and stabilizers.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials.

The dosage range at which the compounds of Formula I exhibit their ability to act therapeutically can vary depending upon the particular disease or condition being treated and its severity, the patient, the formulation, other underlying disease states that the patient is suffering from, and other medications that may be concurrently administered to the patient. Generally, the compounds of Formula I will exhibit their therapeutic activities at dosages of between about 0.001 mg/kg of patient body weight/day to about 100 mg/kg of patient body weight/day.

EXAMPLES

The following examples present typical syntheses as described in Schemes I, I(a), I(b) and II. These examples are understood to be illustrative only and are not intended to limit the scope of the present invention in any way. As used herein, the following terms have the indicated meanings: "g" refers to grams; "mmol" refers to millimoles; "mL" refers to milliliters; "° C." refers to degrees Celsius; "TLC" refers to thin layer chromatography; "LC/MS" refers to liquid chromatography mass spectrometry; "APCI" refers to atmospheric pressure chemical ionization; "mp" refers to melting point; "ppm" refers to parts per million; "TMS" refers to tetramethylsilane; "GC/MS" refers to gas chromatography/mass spectroscopy; "Hz" refers to hertz; "MHz" refers to megahertz; "NMR" refers to nuclear magnetic resonance; "M/S" refers to mass spectra; "IR" refers to infrared spectra.

Example 1

Preparation of (3-fluoro-benzyl)-[2-(3-thieno[2,3-d] isoxazol-3-yl-phenoxy)-ethyl]-amine maleate (Scheme II, Compound 1)

MDL 814009

Generally, for steps A, B, and D: NMR spectra were recorded using a Varian XL-300 spectrometer at 300 MHz for $^1$H and 75 MHz for $^{13}$C. All chemical shifts are reported in ppm relative to TMS standard. GC/MS was accomplished using a Hewlett Packard Model 5972 with the following parameters: 30 meter HP 5MS column, i.d. 0.25 mm, film thickness 0.25 µm; heating rate −50° C. for 1 minute, then 20° C./minute up to 300° C.; injector temperature, 250° C.; detector temperature, 280° C. The mass spectrum was obtained on a Finnigan Mat TSQ 700 spectrometer. Microanalyses were done by Robertson Microlit, Madison, N.J.

For steps C, E, F, G and H: NMR spectra were recorded using a Gemini 300 spectrometer. IR spectra were recorded on a Mattson Galaxy 500 FTIR. Mass Spectra were obtained on a Finnigan MAT4600 spectrometer. Elemental analyses were performed by Robertson Microlit, Inc., Madison, N.J.

Step A:

Preparation of (3-bromothiophen-2-yl)-(3-methoxyphenyl)methanone (Scheme II, Compound 4)

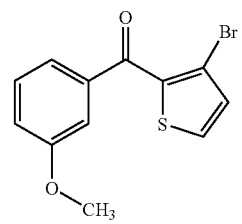

Mix 3-bromothiophene (1.5 kg, 9.2 mol) and dichloromethane (10 L) in a 22-L, 3-necked flask fitted with a stirrer, thermometer, dropping funnel and continuous nitrogen purge. Cool (−5° C.) the stirred solution under continuous nitrogen purge and add titanium (IV) chloride (3.0 kg, 15.8 mol), dropwise over a period of time of 30 minutes. Temperature at the end of the addition is −5° C. To the cold (0° C.) solution, add a solution of m-anisoyl chloride (1.73 kg, 10.1 mol) in dichloromethane (2.5 L) over a period of time of 60 minutes. Monitor the progress of the reaction by GC/MS (Retention times: 2=2.2 minutes, 3=5.1 minutes, 4=21.4 minutes]. Run an identical reaction at the same time in separate equipment. After 20 hours, transfer the reaction mixtures to a 30-gallon hastelloy reactor containing stirred ice water (40 kg). Stir for 30 minutes, separate the phases, and wash the lower organic phase with 10% sodium hydroxide solution (20 L). Extract the basic (pH 10) aqueous phase with dichloromethane (6L), combine the organic extracts, dry (MgSO$_4$, 1 kg), filter and wash the filter cake with dichloromethane (5 L). Concentrate the combined filtrates (35° C./100 torr) to give the crude compound as an oil (6.25 kg). In a 22-L flask, dilute the crude compound with t-butyl methyl ether (6 L). Seed the solution and let stand at 5° C. for a period of time of 64 hours. After product crystallizes, filter off and wash with cold (5° C.) t-butyl methyl ether (2 L) and dry (25° C.) to give the final, desired product 4 (3.785 kg, 69% Yield). ¹H NMR (300 MHz, CDCl₃): 7.56 d, 1H, 7.39 m, 3H, 7.15 m, 2H, 3.87 s, 3H. M/S (Cl, CH₄): [M+H]⁺=297.

Step B:

Preparation of (3-bromothiophen-2-yl)-(3-methoxyphenyl)methanone oxime
(Scheme II, Compound 5)

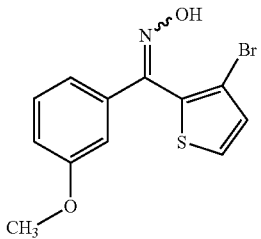

Mix hydroxylamine hydrochloride (1.77 kg, 25.5 mol), 4 (3.785 kg, 12.6 mol), and pyridine (12 L) in a 22-L, 3-necked flask fitted with a stirrer, thermometer, heating mantle and continuous nitrogen purge. Stir the mixture and heat, maintaining at 80° C. Monitor the progress of the reaction using GC/MS (Retention Times: 5=16.4 minutes, 4=21.4 minutes). The reaction should reach completion after 7 hours. Cool the stirred mixture to ambient temperature overnight. Dilute the reaction mixture with dichloromethane (20 L) and wash with 3N HCl (2×20 L) (pH of the second wash is acidic). Wash the organic phase with water (3×10 L) (pH of the second wash is neutral), dry (1 kg MgSO₄), filter and wash the filter cake with dichloromethane (6 L). Evaporate the filtrate (35° C./100 torr) to give the crude compound (4.9 kg). Dissolve the crude compound in hot (80° C.) toluene (4 L). Cool the stirred solution slowly to ambient temperature and then maintain at 5° C. for 16 hours. Filter off the product, wash with cold (5° C.) toluene (2 L) and air dry to give the final desired compound 5 (3.45 kg, 87% Yield). ¹H NMR (300 MHz, CDCl₃): 8.62 bs, 1H, 7.22 m, 6H, 3.81 d, 3H. M/S (Cl, CH₄): [M+H]⁺=312.

Step C:

Preparation of 3-(3-methoxyphenyl)thieno[2,3-d]isoxazole
(Scheme II, Compound 6)

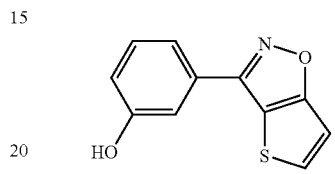

Mix 5 (50 g, 0.16 mol), potassium carbonate (33 g, 0.24 mol) and copper iodide (2.0 g, 0.011 mol) in isopropyl alcohol (0.5 L) and heat to reflux for 2.5 hours. GC/MS analysis of an aliquot added to water and extracted with ethyl acetate shows complete conversion. Cool (~40° C.) the mixture and add water (4 L) containing ammonium hydroxide (0.1 L). After 0.5 hours, collect the solid and wash with water (0.2 L). Air-dry the solid and collect the compound as a tan solid (35.9 g). Dissolve the solid (some insoluable remain) in ethyl acetate (0.3 L) and treat with charcoal. Filter the mixture through celite and concentrate to give the final, desired compound 6 (32.9 g, 89% Yield).

Step D:

Preparation of 3-thieno[2,3-d]isoxazol-3-yl-phenol
(Scheme II, Compound 7)

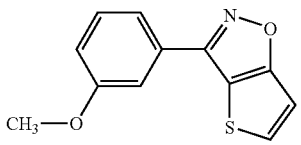

Stir a solution of 6 (139.4 g, 0.6 mol) in dichloromethane (3.15 L) in a 12-L, 3-necked flask fitted with a stirrer, digital thermometer, dropping funnel and continuous nitrogen purge. Cool the solution and maintain the temperature at –12° C. to –5° C. while adding boron tribromide (450 g, 1.8 mol) over a period of time of 36 minutes. Stir the reaction mixture at –5° C. for 12 minutes and then remove the cooling bath and stir at ambient temperature. Monitor the reaction using thin layer chromatography (Merck silica gel, dichloromethane, R_f of 6=0.71, R_f of 7=0.19). The reaction reaches completion after 1.5 hours (pot temperature=15.4° C.). Cool the stirred mixture to and maintain at –10° C. while adding methanol (835 mL, 20.7 mol) over a period of time of 15 minutes. Stir the mixture for an additional 15 minutes and add 25% sodium hydroxide (715 g) over a period of time of 50 minutes while maintaining a temperature of –10° C. to 0° C. The pH at the end of the addition is 7.25. Remove the methanol and dichloromethane at 30° C./7 torr, resulting in a tan solid suspended in the aqueous phase. Filter off the solid, wash with water and dry (35° C./7 torr) to give the final, desired compound 7 (129.1 g, 99% Yield). ¹H NMR (300 MHz, DMSO-d₆): 9.97 s, 1H, 8.18 dd, 1H, 7.35 m, 4H, 6.97 d, 1H. M/S (Cl, CH₄): [M+H]⁺=218.

Step E:

Preparation of N-(3-fluorobenzyl)-2-chloroacetamide (Scheme II, Compound 10)

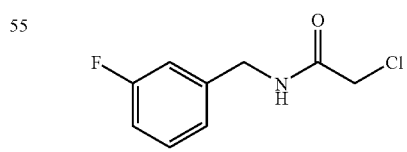

Mix amine 8 (5.0 g, 40 mmol) in toluene (50 mL) with potassium carbonate (7.0 g) in water (25 mL). Add 2-chloroacetyl chloride (9) (5.0 g, 44 mmol) via syringe over a period of time of 5 minutes. GC/MS shows complete conversion in the organic phase after 1 hour. Wash the organic phase with water (20 mL), dry (MgSO₄) and concentrate to an oil. Add a few seed crystals to induce complete crystallization and collect the final, desired compound 10 (7.8 g, 97%).

mp 53–55° C.; $^1$H NMR (CDCl$_3$) δ 7.37–7.23 (m, 1), 7.12–6.92 (m, 3), 4.46 (d, 2, J=6 Hz), 4.09 (s, 2); $^{19}$F NMR (CDCl$_3$) δ −113.9 (m); IR (KBr) 3309, 1647, 1539 cm$^{-1}$; MS (APCI) m/z (relative intensity) 202 (M+H) (100), 109 (31).

Step F:

Preparation of (3-fluorobenzyl)-[2-(3-thieno[2,3-d]isoxazol-3-yl-phenoxy)-2-(oxo)ethyl]-amine (Scheme II, Compound 11)

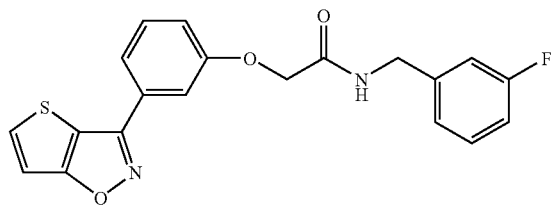

Mix 7 (16 g, 74 mmol), 10 (15.5 g, 77 mmol), potassium carbonate (20.3 g, 147 mmol) and sodium iodide (2.3 g, 15.3 mmol) in acetone (300 mL) and heat to reflux for 22 hours. GC/MS shows complete conversion. Pour the reaction mixture into a mixture of ethyl acetate (1 L), heptane (0.2 L) and water (1 L). Separate the layers and wash the organic phase with brine (0.5 L), dry (MgSO$_4$), and concentrate. Dissolve the solid in hot toluene (200 mL) and let stand overnight. Collect the solid and air dry to give the final, desired compound 11 (24.8 g, 88%).

mp 94–96° C.; $^1$H NMR (CDCl$_3$) 7.73–6.94 (m, 9), 4.63 (s, 3), 4.58 (d, 2, J=6 Hz); $^{19}$F NMR (CDCl$_3$) δ−113.9 (m); IR (KBr) 3314, 1653, 1531, 1497 cm$^{-1}$; MS (APCI) m/z (relative intensity) 383 (M+H) (100), 285 (7), 207 (10), 109 (9). Anal. calcd. for C$_{20}$H$_{15}$N$_2$O$_3$FS: C, 62.82; H, 3.95; N, 7.33. Found: C, 62.70; H, 3.76; N, 7.21.

Steps G and H:

Preparation of (3-fluorobenzyl)-[2-(3-thieno[2,3-d]isoxazol-3-yl-phenoxy)-ethyl]-amine maleate (Scheme II, Compound 1a)

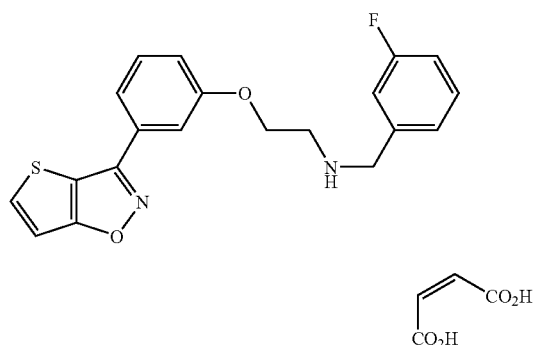

To a solution of 11 (4.0 g, 10.5 mmol) in THF (20 mL), add 10 M borane-methyl sulfide complex in tetrahydrofuran (3.2 mL, 32 mmol) and heat (60° C.) for 2 hours. HPLC analysis shows ~2:1 mixture of the borane complex of structure 1 and the free amine of structure 1. Cool (25° C.) the solution and add methanol (6 mL) over a period of time of 10 minutes which causes an exotherm to 48° C. Add diethylenetriamine (4 mL) and heat (60° C.) for 1 hour. HPLC analysis shows complete conversion to the free amine. Cool the mixture (45° C.), concentrate (40° C./20 torr) and add tetrahydrofuran (15 mL), methanol (10 mL) and sodium hydroxide (3M solution, 10 mL). Stir for 1 hour and concentrate. Add ethyl acetate (50 mL), heptane (10 mL) and brine (15 mL) to the residue. Separate the organic phase and add silica gel (8 g). After 1 hour, filter the mixture and wash the silica gel with ethyl acetate (200 mL). Concentrate the filtrate to give the crude product 1 (3.05 g, 79% Yield, 95% HPLC purity). Dissolve the crude product 1 in hot isopropyl alcohol (10 mL), add maleic acid (1.0 g, 8.6 mmol) in isopropyl alcohol (10 mL) and cool. The preferred salt forms also include the mesylate salt (from methane sulfonic acid in tetrahydrofuran) and the hydrochloride salt (from hydrochloric acid in acetonitrile). After 2 hours, collect the solid and dry in a vacuum oven (60° C./10 torr) for 4 hours to give the final desired compound 1a (3.39 g, 67% Yield, 97.9% HPLC purity). mp 144–145° C.; $^1$H NMR (d$_6$-DMSO) δ8.20 (d, 1, J=5 Hz), 7.63–7.20 (m, 9), 6.02 (s, 2), 4.37 (m, 2), 4.29 (s, 2), 3.40 (m, 2); $^{19}$F NMR (d$_6$-DMSO) δ −113.0 (m); IR (KBr) 1702, 1617, 1587, 1531, 1486 cm$^{-1}$; MS (APCI) m/z (relative intensity) 369 (M+H) (100). Anal. calcd. for C$_{20}$H$_{17}$N$_2$O$_2$FS.C$_4$H$_4$O$_4$: C, 59.50; H, 4.37; N, 5.78. Found: C, 59.46; H, 4.45; N, 5.79. HPLC conditions: Column: Phenomenex Luna 3 micron Phenyl-Hexyl (100×4.6 mm): Buffer: 20 mM NH$_4$Oac, pH adjusted to 5.2 with HOAc. Eluant: Isocratic 1:1 MeCN and Buffer, 1.0 mL/min. UV detector at 230 nm. Compound 1: R$_T$=4.2 min; compound 10: R$_T$=7.6 min; compound 1: complexed with borane, R$_T$=23.3 min.

Example 1A

Alternative Preparation of (3-fluoro-benzyl)-[2-(3-thieno[2,3-d]isoxazol-3-yl-phenoxy)-ethyl]-amine (Scheme I(a), Compound 1)

Step H:

Preparation of (2-bromo-ethyl)-(3-fluoro-benzyl)-amine (Scheme I(a), Compound 9)

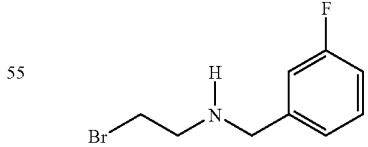

Combine 3-fluorobenzylamine (5.0 g, 0.0400 mol), fused sodium acetate (3.28 g, 0.0400 mol) and 1,2-dibromoethane (7.51 g, 0.0400 mol) and reflux for several hours. Pour the mixture into water and add sodium carbonate to create a basic pH. Remove the unreacted 1,2-dibromoethane by distillation. Extract the left-over residue with ether and evaporate to obtain the final, desired compound. The compound can form the hydrochloride salt.

Step I:

Preparation of (3-fluoro-benzyl)-[2-(3-thieno[2,3-d]isoxazol-3-yl-phenoxy)-ethyl]-amine (Scheme I(a), Compound 1)

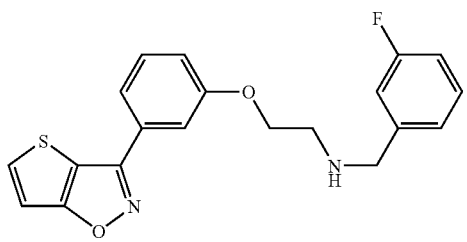

Add dichloromethane to 3-thieno[2,3-d]isoxazol-3-yl-phenol (10 g, 0.046 mol) or the appropriately protected 3-thieno[2,3-d]isoxazol-3-yl-phenol as is known in the art, and stir with sodium hydroxide (1M; 28 mL) to form the sodium salt. Combine the sodium salt from 3-thieno[2,3-d]isoxazol-3-yl-phenol, (2-bromo-ethyl)-(3-fluorobenzyl)-amine (37.5 g, 0.161 mol) in toluene (100 mL) and heat (reflux) for 24 hours. Allow to cool, filter the reaction mixture and evaporate off the solvent to give the final, desired compound. Compound may be purified by distillation under reduced pressure.

Example 1(B)

Alternative preparation of (3-fluoro-benzyl)-[2-(3-thieno[2,3-d]isoxazol-3-yl-phenoxy)-ethyl]-amine (Scheme I(b), Compound 1)

Step N:

Preparation of 2-(3-fluoro-benzylamino)-ethanol (Scheme I(b), Compound 4)

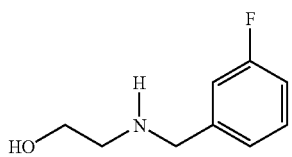

Combine 3-fluorobenzylamine (31.1 g, 0.248 mol), 2-chloroethanol (10 g, 0.124 mol) and water (30 g, 1.66 mol) and heat on a steam-bath for ~5 hours. Add sodium hydroxide (15 g, 0.373 mol) to the cooled solution and heat the resulting mixture on a steam-bath for ~30 minutes. Add water (~50 mL) to dissolve the inorganic salts and extract the two-phase mixture twice with 25 mL and 13 mL portions of benzene. Combine the extracts and remove the water by co-distillation with benzene through a modified Claisen flask. The final desired compound may be purified with further distillation.

Step O:

Preparation of toluene-4-sulfonic acid 2-[tert-butoxycarbonyl-(3-fluoro-benzyl)-amino]-ethyl ester (Scheme I(b), Compound 6)

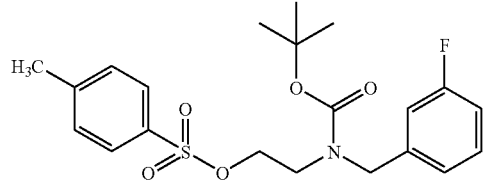

Add p-toluenesulfonyl-chloride (0.71 g, 3.71 mmol), portionwise, to a mixture of (3-fluoro-benzyl)-(2-hydroxy-ethyl)-carbamic acid dimethyl-ethyl ester (1 g, 3.71 mmol, prepared from 2-(3-fluoro-benzylamino)-ethanol by methods as are known in the art), triethylamine (0.751 g, 7.4 mmol) and dichloromethane (6 mL). Stir the resulting suspension vigorously overnight at room temperature. Add water (10 mL), separate the organic layer, and extract the aqueous layer with dichloromethane (5 mL), twice. Combine the organic layers and wash with citric acid (5 mL, 20% in water), dry with sodium sulfate and evaporate the solvent to give the final, desired compound. The final compound may be purified by chromatography.

Step P:

Preparation of (3-fluoro-benzyl)-[2-(3-thieno[2,3-d]isoxazol-3-yl-phenoxy)-ethyl]-amine (Scheme I(b), Compound 1)

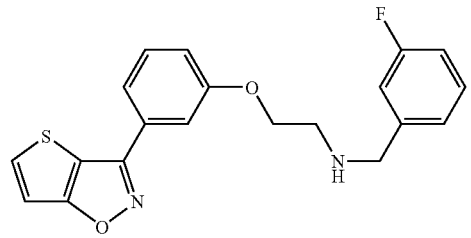

The title compound is prepared from a mixture of toluene-4-sulfonic acid 2-[tert-butoxycarbonyl-(3-fluoro-benzyl)-amino]-ethyl ester and 3-thieno[2,3-d]isoxazol-3-yl-phenol essentially as described in Example 3, Scheme I, Step F. It is understood by one skilled in the art that the nitrogen may be deprotected by acid hydrolysis, to give the final, desired compound.

Example 2

Preparation of 3-thieno[2,3-d]isoxazol-3-yl-phenol (Scheme I, Compound 7)

Step A:

Preparation of (3-bromothiophen-2-yl)-(3-methoxyphenyl)methanone (Scheme I, Compound 4)

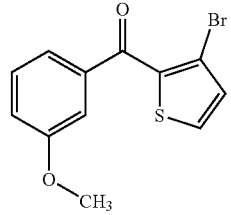

Add phenyllithium (210 mL, 0.44 mol) dropwise, to a cold (5° C.) mixture of 3-bromothiophene (66 g, 0.40 mol) and ether (400 mL) over two hours to form the lithiated thiophene intermediate. Add the lithiated thiophene intermediate mixture to a cold (−70° C.) mixture of THF and m-methoxybenzoyl chloride over three hours, then quench the reaction with water and extract with ether. Wash the ether with 10% NaOH and water, dry (MgSO₄), filter and evaporate to yield an oil. Purify the oil by column (alumina) chromatography, eluting with hexane up to 50% ether in hexane. Distill the product in vacuo and recrystallize (ether:hexane) to obtain the title compound (89.1 g, 75% Yield), m.p. 40° C.

Step B:

Preparation of (3-bromothiophen-2-yl)-(3-methoxyphenyl)methanone oxime
(Scheme I, Compound 5)

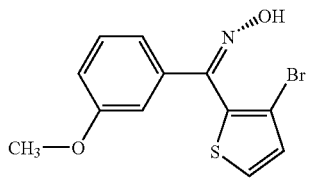

Stir a mixture of (3-bromothiophen-2-yl)-(3-methoxyphenyl)methanone (7 g, 0.024 mol), hydroxylamine hydrochloride (3.09 g, 0.048 mol) and pyridine (40 mL) overnight at room temperature, and then heat the mixture (100° C.–105° C.) for four hours. TLC (DCM) shows that the reaction is complete. Quench the reaction mixture with water and extract with ether (three times). Wash the ether phase with HCl (3N) and water, dry (MgSO₄), filter and concentrate to yield an oil that solidifies. Recrystallize the solid from ether:hexane to obtain the title compound (6.4 g, 87% Yield), m.p. 102–103° C.

Step C:

Preparation of 3-(3-methoxyphenyl)thieno[2,3-d]isoxazole
(Scheme I, Compound 6)

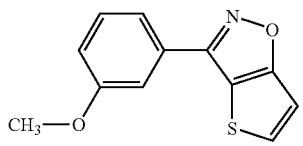

Reflux a mixture of (3-bromothiophen-2-yl)-(3-methoxyphenyl)methanone oxime (10 g, 0.032 mol), KOH (3.6 g, 0.064 mol dissolved in 10 mL water) and 2-ethoxyethanol (40 mL) under nitrogen for one hour at 105–110° C. Add copper chloride (0.16 g, 0.0016 mol) whereupon the reaction mixture becomes dark brown in color. Heat the reacton for an additional four hours. TLC shows that the reaction is complete. Add water and extract the organics into ether. Wash the ether phase with water, dry (MgSO₄), filter and concentrate to yield an oil. Purify the oil by column (alumina) chromatography, and elute with 15% ether in hexane to obtain white crystals. Recrystallize the crystals from ether:hexane to yield the title compound (5 g, 68% Yield), m.p. 51–52° C.

Step D:

Preparation of 3-thieno[2,3-d]isoxazol-3-yl-phenol
(Scheme I, Compound 7)

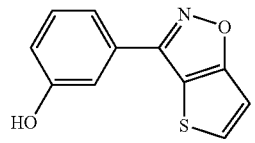

Combine and stir under nitrogen at 140° C. a mixture of 3-(3-methoxyphenyl)thieno[2,3-d]isoxazole (8 g, 0.035 mol) and pyridine hydrochloride (80 g, 0.69 mol) for nine hours. TLC (ethyl acetate: dichloromethane) shows the reaction is complete. Cool the reaction mixture to room temperature, and pour into water. Extract the organics into ethyl acetate:ether (50:50), and wash once with HCl (3N), three times with water, dry (MgSO₄) and evaporate to yield an oil. Purify the oil by column (silica) chromatography, eluting with 5% ethyl acetate in dichloromethane, to yield a solid. Recrystallize this solid (ether:hexane) to obtain the title compound as an orange/tan solid (3 g, 40% yield), m.p. 114–116° C.

Example 3

Preparation of (R)-(−)-3-[3-(1-Benzyl-pyrrolidin-3-yloxy)-phenyl]-thieno[2,3-d]isoxazole hydrochloride and (3-Fluoro-benzyl)-[2-(3-thieno[2,3-d]isoxazol-3-yl-phenoxy)-ethyl]-amine hydrochloride Scheme I—Step E:

Preparation of 3-[3-(2-bromo-ethoxy)-phenyl]-thieno[2,3-d]isoxazole (Scheme I, Compound 9)

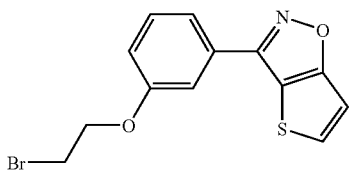

Mix 3-thieno[2,3-d]isoxazol-3-yl-phenol (8.5 g, 39.1 mmol), potassium carbonate (10.8 g, 78.1 mmol), and 1,2-dibromoethane (65 mL, 754 mmol) and heat to reflux, under nitrogen. Cool the reaction mixture to room temperature, overnight. TLC (50% ethyl acetate in heptane) shows that there is still some starting material left. Reflux the reaction mixture for an additional 3 hours. Remove 1,2-dibromoethane by vacuum distillation (45° C.). Dilute the reaction mixture with water (300 mL) and extract with ethyl acetate (2×150 mL). Wash the combined extracts with water (150 mL), saturated sodium chloride (150 mL), dry (MgSO₄) and concentrate (in vacuo) to afford compound 12 as a black residue. Purify the black residue by column (silica) chromatography (30% ethyl acetate in heptane). Combine the appropriate fractions to obtain an amber oil which solidifies to afford the title compound as a tan solid (8.52 g, 67% Yield).

Scheme I—Step E:

Preparation of 3-[3-(3-bromo-propoxy)-phenyl]-thieno[2,3-d]isoxazole and 3-[3-(3-Chloro-propoxy)-phenyl]-thieno[2,3-d]isoxazole (Scheme I, Compound 9)

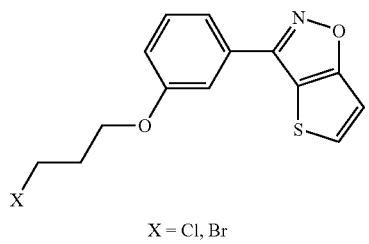

X = Cl, Br

Stir a mixture of 3-thieno[2,3-d]isoxazol-3-yl-phenol (10.0 g, 46.0 mmol), potassium carbonate (12.7 g, 92.0 mmol), 1-bromo-3-chloropropane (11.4 mL, 115 mmol) and N-methylpyrrolidine (70 mL) and heat (90–95° C.) under nitrogen, for 18 hours. Cool the reaction mixture and pour into water (500 mL) and extract with ethyl acetate (1×200 mL and 1×100 mL). Combine and wash the ethyl acetate extracts with 5% aqueous sodium chloride (3×200 mL) and concentrate in vacuo to yield a dark brown oil. Purify the crude product by silica gel chromatography [dichloromethane:heptane/(50:50)] to give the title compounds (6.5 g) as an amber oil. This amber oil is a mixture of 3-[3-(3-bromo-propoxy)-phenyl]-thieno[2,3-d]isoxazole (2.21 g, 6.65 mmol) and 3-[3-(3-chloro-propoxy)-phenyl]-thieno[2,3-d]isoxazole (3.77 g, 12.8 mmol), as determined through NMR.

Scheme I—Step F:

Preparation of (3-fluoro-benzyl)-[2-(3-thieno[2,3-d]isoxazol-3-yl-phenoxy)-ethyl]-amine hydrochloride (Scheme I, Compound 1)

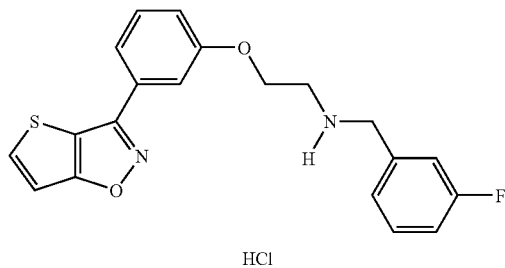

HCl

Mix 3-[3-(2-bromo-ethoxy)-phenyl]-thieno[2,3-d]isoxazole (8.70 g, 26.8 mmol), 3-fluoro-benzylamine (15.0 g, 120 mmol), potassium carbonate (9.30 g, 67.3 mmol) and acetonitrile (anhydrous, 90 mL) and heat at 75° C., overnight. Cool the reaction mixture to room temperature. TLC (DCM) shows that the reaction is complete. Dilute the reaction mixture with ethyl acetate (200 mL), filter and concentrate to give compound 1 (free base) as a viscous, amber oil. Purify the oil by chromatography (3:1/ethyl acetate:heptane) and acidify with ethereal hydrochloric acid in ethanol:chloroform (200 mL:300 mL) to pH=2–3. Filter the resulting slurry, evaporate and recrystallize (250 mL methanol) to afford the title compound (5.85 g, 54%) as a white powder, which is dried (60° C., 1.0 mm Hg) for 6 hours. Microanalysis (C, H, N) is consistent with the final, desired product. mp=217–220° C.

Scheme I—Step G:

Preparation of (S)-(+)-3-[3-(1-benzyl-pyrrolidin-3-yloxy)-phenyl]-thieno[2,3-d]isoxazole hydrochloride (Scheme I, Compound 12)

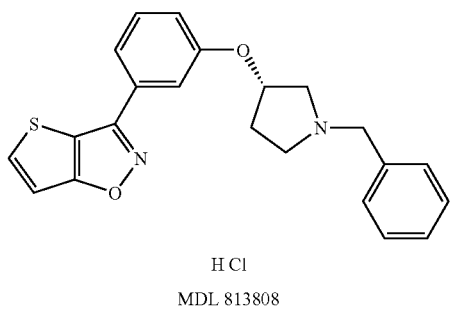

HCl
MDL 813808

To a solution (room temperature) of 3-thieno[2,3-d]isoxazol-3-yl-phenol (500 mg, 2.30 mmol), R-(+)-1-benzyl-3-pyrrolidine (417 mg, 2.35 mmol), triphenylphosphine (604 mg, 2.30 mmol) and anhydrous tetrahydrofuran (5 mL), add diethyl azodicarboxylate (409 mg, 2.35 mmol), under a nitrogen atmosphere and stir overnight. Concentrate the reaction mixture (in vacuo) to a residue. Take the residue up in ether (40 mL), wash with 5% NaOH (20 mL) and brine (20 mL), dry (MgSO$_4$), filter and evaporate (in vacuo) to yield an orange residue. Purify the orange residue by column chromatography (50% ethyl acetate in heptane). Combine the appropriate fractions and concentrate to obtain an orange oil (597 mg, 69% Yield). Dissolve the free base in hot ethanol, cool (room temperature) and acidify to a pH approximately 2–3 with ethereal HCl. Concentrate the reaction mixture (in vacuo) to obtain an orange oil, triturate (ethyl acetate) and recrystallize (methanol:ethyl acetate) to obtain the title compound as crystals (325 mg, 34% Yield). Microanalysis (C, H, N) is consistent with the final desired compound. $[\alpha]_D^{21}$=+28.9 (methanol, c=0.985).

mp=169–170° C.

Scheme I—Step G:

Preparation of (R)-(−)-3-[3-(1-benzyl-pyrrolidin-3-yloxy)-phenyl]-thieno[2,3-d]isoxazole hydrochloride (Scheme I, Compound 12)

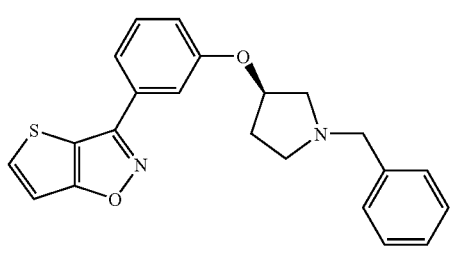

HCl
MDL 813809

The title compound is prepared from S-(−)-1-benzyl-3-pyrrolidine, triphenylphosphine, and diethyl azodicarboxylate essentially as described above in Example 1, Scheme I, Step B. Microanalysis (C, H, N) is consistent with the final desired compound. $[\alpha]_D^{21}$=−26.3 (methanol, c=0.985). mp=168–170° C.

Examples 4–17

Examples 4–17 are prepared using techniques of parallel synthesis. Experimental conditions are described in detail for Example 4, with any variations in procedures being noted for Examples 5–17.

Example 4

Preparation of (2-fluoro-benzyl)-[3-(3-thieno[2,3-d]isoxazol-3-yl-phenoxy)-propyl]-amine (Scheme I, Compound 1)

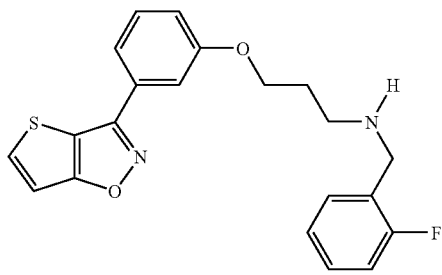

MDL 813518-001

Combine a mixture (1 mmol total) of 3-[3-(3-bromopropoxy)-phenyl]-thieno[2,3-d]isoxazole, 3-[3-(3-chloropropoxy)-phenyl]-thieno[2,3-d]isoxazole with 2-fluorobenzylamine (0.63 g, 5.0 mmol), potassium carbonate (0.41 g, 3.0 mmol) and a mixture of acetonitrile:water (80:20) and heat (80° C.) for 30 hours. Cool the reaction mixture and concentrate to give a residue. Purify the residue by column (silica) chromatography (ethyl acetate). Combine the appropriate fractions and concentrate to give the title compound (0.36 g, 94% Yield) as an oil. Purity by LC/MS (APCI)= 100% area, $[M+H]^+=383$ g/mol.

Example 4A

Preparation of benzyl-[3-(3-thieno[2,3-d]isoxazol-3-yl-phenoxy)-propyl]-amine hydrochloride (Scheme I, Compound I)

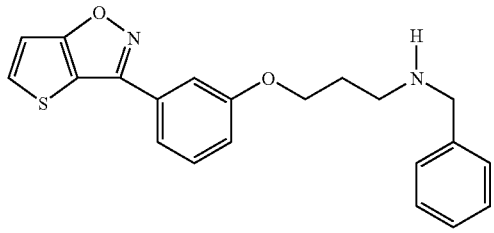

HCl

MDL 813221

Stir a mixture of 3-(3-hydroxyphenyl)theino[2,3-d]isoxazole (3 g, 13.8 mmole), N-methylpyrrolidinone(25 mL) milled postassium carbonate (2 equivalents, 3.8 g, 27.6 mmole) and 1-bromo-3-chloropropane (1.25 equivalents, 2.72 g, 17.25 mmole and heat to 90° C. under a $N_2$ atmosphere. After 1 hour, add an additional 1.25 equivalents of 1-bromo-3-chloropropane and heat the mixture for an additional 16 hours. Pour the cooled reaction mixture into water (125 mL) and extract with ethyl acetate (125 mL). Wash the ethyl acetate extract with 3×50 mL water and concentrated in vacuo. Elute the crude product through silica gel (50 g) with ethyl acetate and combine the pure fractions. Concentrate to give 3 g of amber oil which by NMR and HPLC is a 57:32 mixture of 3-[3-(3-chloropropoxy)-phenyl]-theino[2,3-d]isoxazole: 3-[3-(3-bromopropoxy)-phenyl]-theino[2,3-d]isoxazole. Use this material in the following step. Add benzylamine (7 g, 65 mmole) to a stirred mixture of 3-[3-(3-chloropropoxy)-phenyl]-thieno[2,3-d]isoxazole (57% pure by HPLC) (3 g, 13 mmole) and milled potassium carbonate (5.4 g, 39.0 mmole) in N-methylpyrrolidinone (20 mL) at room temperature. Heat the reaction mixture to 110° C. After 2 hours, cool the reaction mixture and pour into water and extract with ethyl acetate (3×100 mL). Wash the combined extracts with 5% aqueous sodium chloride and concentrate in vacuo. Elute the crude product through silica gel with ethyl acetate to give benzyl-[3-(3-theino[2,3-d]isoxazol-3-yl-phenoxy)-propyl]-amine (2.11 g, 49% yield, 99% HPLC purity) as an amber oil. Dissolve the free base (1.9 g, 5.2 mmole) in ethyl alcohol (20 mL) and acidify with 37% HCl. Crystallize the compound from ethyl alcohol at 5° C. followed by drying at 90° C./8 hrs to give 1.69 g (81% yield) of benzyl-[3-(3-theino[2,3-d]isoxazol-3-yl-phenoxy)-propyl]-amine hydrochloride, mp=195–197° C. The hydrochloride is 99.6% pure by HPLC. The IR (KBr), NMR (DMSO-d6) and MS (M+1=365) are consistent with the proposed structure. Calc. for $C_{21}H_{21}ClN_2O_2S$: 62.91% C, 5.28% H, 6.99% N, Found: 62.95% C, 5.20% H and 6.83% N.

Example 5

Preparation of (4-fluoro-benzyl)-[3-(3-thieno[2,3-d]isoxazol-3-yl-phenoxy)-propyl]-amine (Scheme I, Compound 1)

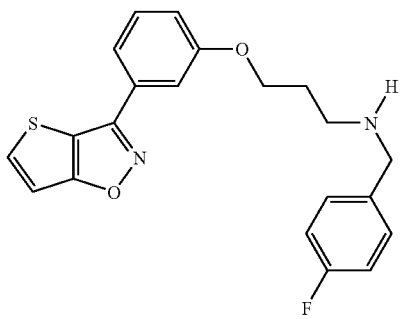

MDL 813519-001

The title compound is prepared from a mixture of 3-[3-(3-bromo-propoxy)-phenyl]-thieno[2,3-d]isoxazole, 3-[(3-(3-chloro-propoxy)-phenyl]-thieno[2,3-d]isoxazole, 4-fluorobenzylamine and potassium carbonate essentially as described above in example 4. Combine the appropriate fractions and concentrate to give the title compound (0.36 g, 94% Yield) as an oil. Purity by LC/MS (APCI)=100% area, $[M+H]^+=383$ m/e.

Example 6

Preparation of (4-chloro-benzyl)-[3-(3-thieno[2,3-d]isoxazol-3-yl-phenoxy)-propyl]-amine (Scheme I, Compound 1)

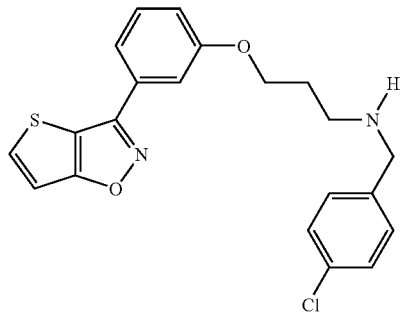

MDL 813520-001

The title compound is prepared from a mixture of 3-[3-(3-bromo-propoxy)phenyl]-thieno[2,3-d]isoxazole, 3-[3-(3-chloro-propoxy)-phenyl]-thieno[2,3-d]isoxazole, 4-chlorobenzylamine and potassium carbonate essentially as described above in example 4. Purity by LC/MS (APCI)=100%, [M+H]$^+$=399 m/e.

Example 7

Preparation of (4-methoxy-benzyl)-[3-(3-thieno[2,3-d]isoxazol-3-yl-phenoxy)-propyl]-amine (Scheme I, Compound 1)

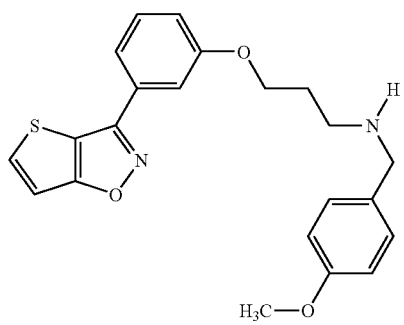

MDL 813521-001

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 4-methoxybenzylamine and potassium carbonate essentially as described above in example 4. Combine the appropriate fractions and concentrate to give the title compound (0.44 g, 100% Yield) as a solid. Purity by LC/MS (APCI)=100% area, [M+H]$^+$=395 m/e.

Example 8

Preparation of [3-(3-thieno[2,3-d]isoxazol-3-yl-phenoxy)-propyl]-thiophen-2-ylmethylamine (Scheme I, Compound 1)

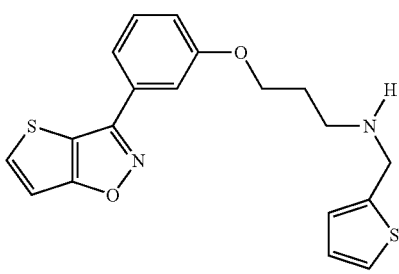

MDL 813522-001

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 2-thiophenemethylamine and potassium carbonate essentially as described above in example 4. Combine the appropriate fractions and concentrate to give the title compound (0.35 g, 94% Yield) as an oil. Purity by LC/MS (APCI)=100% area, [M+H]$^+$=371 m/e.

Example 9

Preparation of [3-(3-thieno[2,3-d]isoxazol-3-yl-phenoxy)-propyl]-thiophen-3-yl-methylamine (Scheme 1, Compound 1)

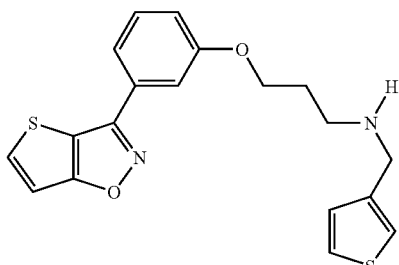

MDL 813523-001

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 3-thiophenemethylamine and potassium carbonate essentially as described above in example 4. Combine the appro-

Example 10

Preparation of pyridin-3-ylmethyl-[3-(3-thieno[2,3-d]isoxazol-3-yl-phenoxy)-propyl]-amine (Scheme I, Compound 1)

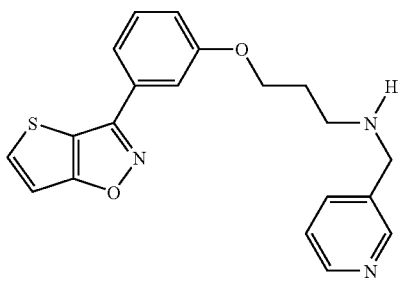

MDL 813524-001

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 3-(aminomethyl)pyridine and potassium carbonate essentially as described above in example 4. Combine the appropriate fractions and concentrate to give the title compound (0.28 g, 77% Yield) as and oil. Purity by LC/MS (APCI)=98% area, [M+H]$^+$=366 m/e.

Example 11

Preparation of 1-phenyl-2-[3-(3-thieno[2,3-d]isoxazol-3-yl-phenoxy)-propylamino]-ethanol (Scheme I, Compound 1)

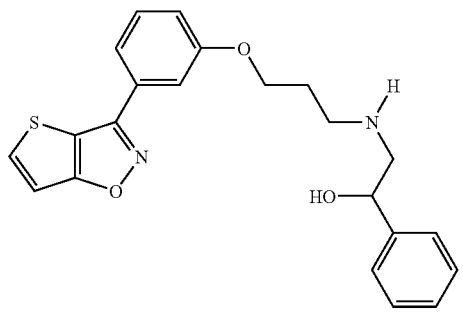

MDL 813525

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 2-amino-1-phenylethanol and potassium carbonate essentially as described above in example 4 except that the column is eluted with a mixture of dichloromethane:methanol (95:5). Combine the appropriate fractions and concentrate to give the title compound (0.62 g, 100% Yield) as a solid. Purity by LC/MS (APCI)=100% area, [M+H]$^+$=395 m/e.

Example 12

Preparation of 3-{3-[3-(4-phenyl-piperazin-1-yl)-propoxy]-phenyl}-thieno[2,3-d]isoxazole (Scheme I, Compound 1)

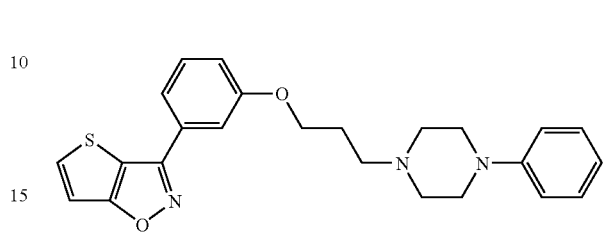

MDL 813526-001

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 1-phenylpiperazine and potassium carbonate essentially as described above in example 4 except that the column is eluted with a mixture of dichloromethane:methanol (98:2). Combine the appropriate fractions and concentrate to give the title compound (0.36 g, 94% Yield) as an oil. Combine the appropriate fractions and concentrate to give the title compound (0.50 g, 100% Yield) as a solid. Purity by LC/MS (APCI)=100% area, [M+H]$^+$=420 m/e.

Example 13

Preparation of 3-(3-{3-[4-(4-fluoro-phenyl)-piperazin-1-yl]-propoxy}-phenyl)-thieno[2,3-d]isoxazole (Scheme I, Compound 1)

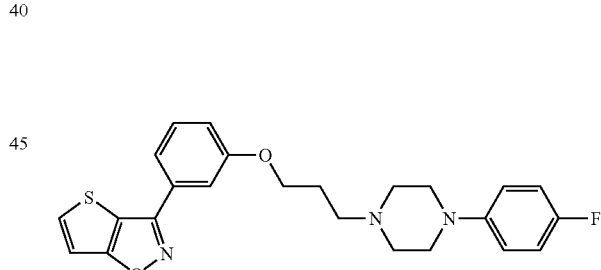

MDL 813527-001

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 1-(4-fluorophenyl) piperazine and potassium carbonate essentially as described above in example 4 except that the column is eluted with a mixture of dichloromethane:methanol (99:1). Combine the appropriate fractions and concentrate to give the title compound (0.44 g, 100% Yield) as a solid. Purity by LC/MS (APCI)=100% area, [M+H]$^+$=438 m/e.

Example 14

Preparation of 3-(3-{3-[4-(2-fluoro-phenyl)-piperazin-1-yl]-propoxy}-phenyl)-thieno[2,3-d]isoxazole (Scheme I, Compound 1)

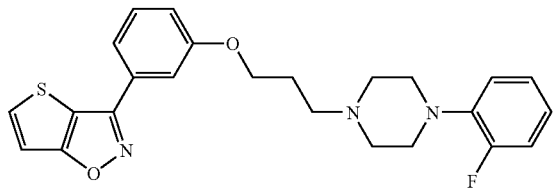

MDL 813528-001

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 1-(2-fluorophenyl) piperazine and potassium carbonate essentially as described above in example 4 except that the column is eluted with a mixture of dichloromethane:methanol (98:2). Combine the appropriate fractions and concentrate to give the title compound (0.45 g, 100% Yield) as a solid. Purity by LC/MS (APCI)=100% area, $[M+H]^+$=438 m/e.

Example 15

Preparation of 3-{3-[3-(4-pyrimidin-2-yl-piperazin-1-yl)-propoxy]-phenyl}-thieno[2,3-d]isoxazole (Scheme I, Compound 1)

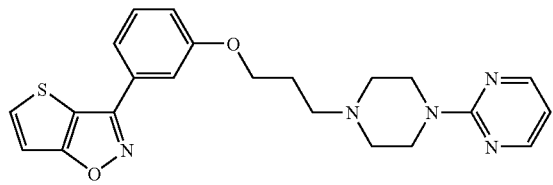

MDL 813529-001

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 2-(pyrimidyl) piperazine dihydrochloride and potassium carbonate essentially as described above in example 4 except that the column is eluted with 50% ethyl acetate in heptane. Combine the appropriate fractions and concentrate to give the title compound (0.50 g, 100% Yield) as a solid. Purity by LC/MS (APCI)=100% area, $[M+H]^+$=422 m/e.

Example 16

Preparation of 4-{[3-(3-thieno[2,3-d]isoxazol-3-yl-phenoxy)-propylamino]-methyl}-benzenesulfonamide (Scheme I, Compound 1)

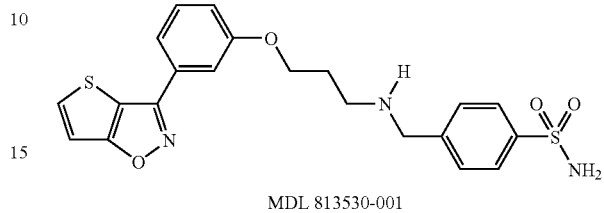

MDL 813530-001

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 4-(aminomethyl) benzenesulfonamide hydrochloride monohydrate and potassium carbonate essentially as described above in example 4 except that the column is eluted using a graded solvent mixture of dichloromethane:methanol (95:5). Combine the appropriate fractions and concentrate to give the title compound (0.12 g, 27% Yield) as a solid. Purity by LC/MS (APCI)=100% area, $[M+H]^+$=444 m/e.

Example 17

Preparation of 4-{2-[3-(3-thieno[2,3-d]isoxazol-3-yl-phenoxy)-propylamino]-ethyl}-benzenesulfonamide (Scheme I, Compound 1)

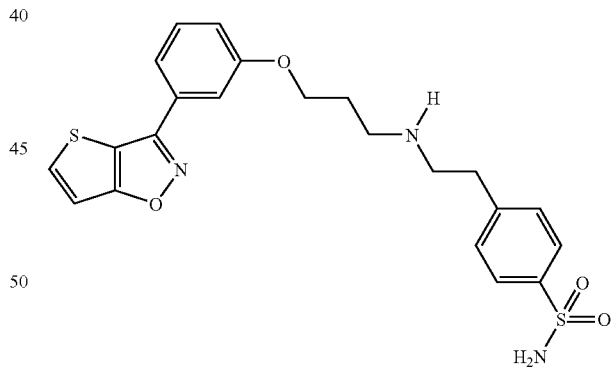

MDL 813531-001

The title compound is prepared from a mixture of 3-[3-(3-bromo-propoxy)-phenyl]-thieno[2,3-d]isoxazole, 3-[3-(3-chloro-propoxy)-phenyl]-thieno[2,3-d]isoxazole, 4-(2-aminoethyl) benzenesulfonamide and potassium carbonate essentially as described above in example 4 except that the column is eluted using a graded solvent mixture of dichloromethane:methanol (90:10). Combine the appropriate fractions and concentrate to give the title compound (0.16 g, 35% Yield) as a solid. Purity by LC/MS (APCI)=96% area, $[M+H]^+$=458 m/e.

Examples 18–26

Examples 18–26 are prepared using techniques of parallel synthesis. Experimental conditions are described in detail for Example 18, with any variations in procedures being noted for Examples 19–26.

Example 18

Preparation of (2-methoxy-benzyl)-[2-(3-thieno[2,3-d]isoxazol-3-yl-phenoxy)-ethyl]-amine (Scheme I, Compound 1)

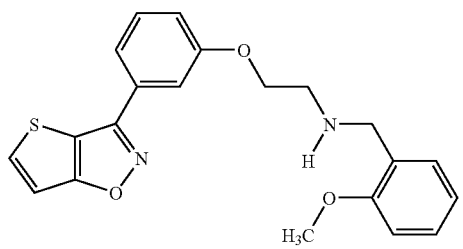

MDL 813732-001

Mix 3-[3-(2-bromo-ethoxy)-phenyl]-thieno[2,3-d]isoxazole (0.324 g, 1 mmol), potassium carbonate (0.28 g, 2 mmol), 2-methoxybenzylamine (0.686 g, 5 mmol) and acetonitrile (anhydrous, 4 mL) and heat at 75° C. for 16.5 hours. Cool the reaction mixture and filter through a Waters Sep-Pak silica gel cartridge (1 g) using ethyl acetate. Combine the appropriate fractions and concentrate to give a residue. Purify the residue by column (10 g silica) chromatography using a step gradient of 60% ethyl acetate in heptane to 100% ethyl acetate to give the title compound (342 mg, 90% Yield). Purity by LC/MS (APCI)=99%, [M+H]$^+$=381.

Example 19

Preparation of (4-fluoro-benzyl)-[2-(3-thieno[2,3-d]isoxazol-3-yl-phenoxy)-ethyl]-amine (Scheme I, Compound 1)

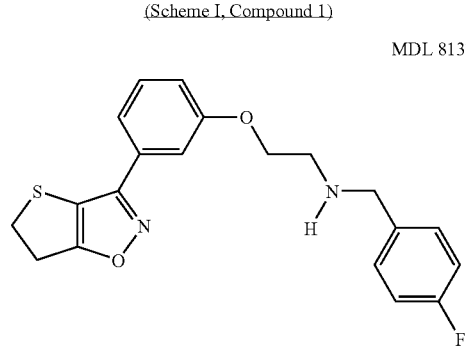

MDL 813728-001

The title compound is prepared from 3-[3-(2-bromo-ethoxy)-phenyl]-thieno[2,3-d]isoxazole, potassium carbonate, 4-fluorobenzylamine and acetonitrile essentially as described above in example 18 except that the column is eluted using a solvent gradient of 40% ethyl acetate in heptane, to 100% ethyl acetate. Purity by LC/MS (APCI)= 100%, [M+H]$^+$=369.

Example 20

Preparation of (4-chloro-benzyl)-[2-(3-thieno[2,3-d]isoxazol-3-yl-phenoxy)-ethyl]-amine (Scheme I, Compound 1)

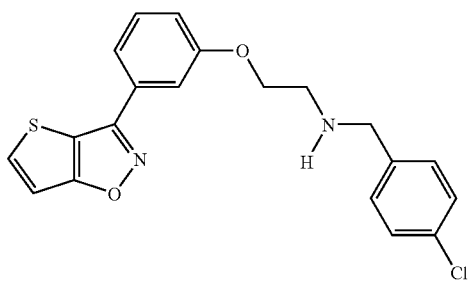

MDL 813729-001

The title compound is prepared from 3-[3-(2-bromo-ethoxy)-phenyl]-thieno[2,3-d]isoxazole, potassium carbonate, 4-chlorobenzylamine and acetonitrile essentially as described above in example 18 except that the column is eluted using a gradient of 40% ethyl acetate in heptane, to 100% ethyl acetate. Purity by LC/MS (APCI)=100%, [M+H]$^+$=385.

Example 21

Preparation of (3-fluoro-benzyl)-[2-(3-thieno[2,3-d]isoxazol-3-yl-phenoxy)-ethyl]-amine (Scheme I, Compound 1)

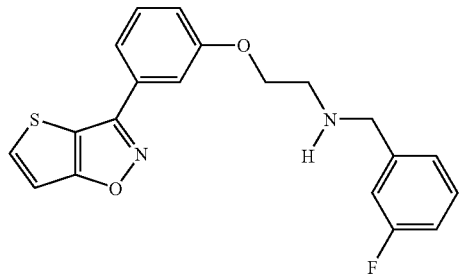

MDL 813730-001

The title compound is prepared from 3-[3-(2-bromo-ethoxy)-phenyl]-thieno[2,3-d]isoxazole, potassium carbonate, 3-fluorobenzylamine and acetonitrile essentially as described above in example 18 except that the column is eluted using a graded solvent mixture of 40% ethyl acetate in heptane to 100% ethyl acetate. Purity by LC/MS (APCI)= 100%, [M+H]$^+$=369.

Example 22

Preparation of (4-methyl-benzyl)-[2-(3-thieno[2,3-d]isoxazol-3-yl-phenoxy)-ethyl]-amine (Scheme I, Compound 1)

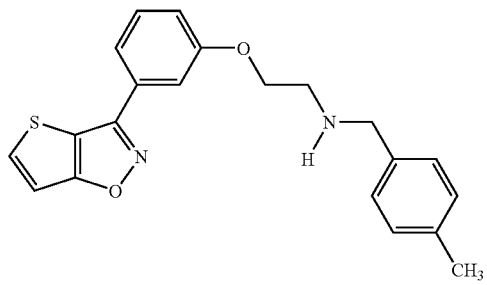

MDL 813731-001

The title compound is prepared from 3-[3-(2-bromoethoxy)-phenyl]-thieno[2,3-d]isoxazole, potassium carbonate, 4-methylbenzylamine and acetonitrile essentially as described above in example 18. Purity by LC/MS (APCI)=100%, $[M+H]^+=365$.

Example 23

Preparation of (3,4-dichloro-benzyl)-[2-(3-thieno[2,3-d]isoxazol-3-yl-phenoxy)-ethyl]-amine (Scheme I, Compound 1)

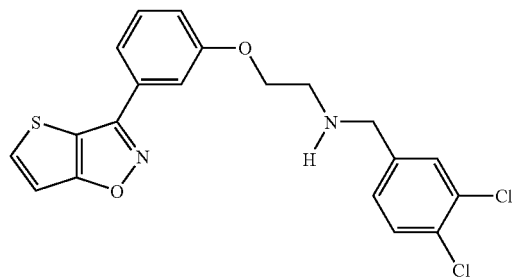

MDL 813733-001

The title compound is prepared from 3-[3-(2-bromoethoxy)-phenyl]-thieno[2,3-d]isoxazole, potassium carbonate, 3,4-dichlorobenzylamine and acetonitrile essentially as described above in example 18 except that the column is eluted using a graded solvent mixture of 40% ethyl acetate in heptane, to 100% ethyl acetate. Purity by LC/MS (APCI)= 100%, $[M+H]^+=419$.

Example 24

Preparation of [2-(3-thieno[2,3-d]isoxazol-3-yl-phenoxy)-ethyl]-thiophen-3-yl-methylamine (Scheme I, Compound 1)

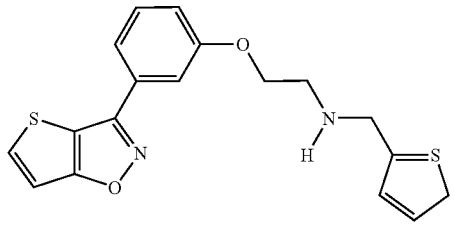

MDL 813734-001

The title compound is prepared from 3-[3-(2-bromoethoxy)-phenyl]-thieno[2,3-d]isoxazole, potassium carbonate, thiophen-3-yl-methylamine (prepared according to *Synthetic Metals*, 26 (1988)153–168) and acetonitrile essentially as described above in example 18, except that water (0.40 mL) is added to the reaction mixture before heating. Purity by LC/MS (APCI)=100%, $[M+H]^+=357$.

Example 25

Preparation of [2-(3-thieno[2,3-d]isoxazol-3-yl-phenoxy)-ethyl]-thiophen-2-ylmethyl-amine (Scheme I, Compound 1)

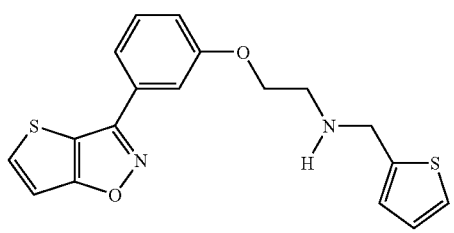

MDL 813735-001

The title compound is prepared from 3-[3-(2-bromoethoxy)-phenyl]-thieno[2,3-d]isoxazole, potassium carbonate, C-Thiophen-2-yl-methylamine and acetonitrile essentially as described above in example 18 except that the column is eluted using a graded solvent mixture of 40% ethyl acetate in heptane, to 100% ethyl acetate. Purity by LC/MS (APCI)=100%, $[M+H]^+=357$.

Example 26

Preparation of pyridin-3-ylmethyl-[2-(3-thieno[2,3-d]isoxazol-3-yl-phenoxy)-ethyl]-amine (Scheme I, Compound 1)

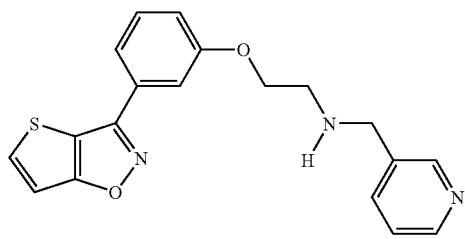

MDL 813736-001

The title compound is prepared from 3-[3-(2-bromoethoxy)-phenyl]-thieno[2,3-d]isoxazole, potassium carbonate, 3-(aminomethyl)pyridine and acetonitrile essentially as described above in example 18 except that the Waters Sep-Pak filtration is eluted with 10% methanol in dichloromethane and the column is eluted using a graded solvent mixture of 2% methanol in dichloromethane, to 6% methanol in dichloromethane. Purity by LC/MS (APCI)=100%, $[M+H]^+=352$.

Example 27

Preparation of 2-[2-(3-thieno[2,3-d]isoxazol-3-yl-phenoxy)-ethyl]-1,2,3,4-tetrahydroisoquinoline (Scheme I, Compound 1)

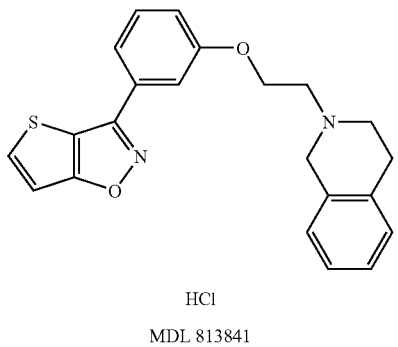

HCl

MDL 813841

Mix 3-[3-(2-bromo-ethoxy)-phenyl]-thieno[2,3-d]isoxazole (0.400 g, 1.23 mmol), potassium carbonate (0.345 g, 2.50 mmol), 1,2,3,4-tetrahydroisoquinoline (0.532 g, 3.99 mmol) and acetonitrile (5.0 mL) and heat at 75° C., overnight. Cool the reaction mixture and filter through a Waters Sep-Pak 1 g silica cartridge (ethyl acetate). Combine the appropriate fractions and concentrate to give a residue. Purify the residue by column (10 g silica) chromatography using a graded solvent mixture of 10% ethyl acetate in dichloromethane to 20% ethyl acetate in dichloromethane. Dissolve the free base in ethanol and acidify with ethereal hydrochloric acid, concentrate to a sticky residue, triturate (methanol:ethyl acetate) and collect the powder. Recrystallize the powder (methanol:ethyl acetate) to obtain the title compound as white crystals (0.285 g, 56%). mp=202–204° C. Microanalysis (C, H, N) is consistent with the final, desired compound.

Example 28

Preparation of 3-{3-[2-(4-phenyl-piperidin-1-yl)-ethoxy]-phenyl}-thieno[2,3-d]isoxazole hydrochloride (Scheme I, Compound 1)

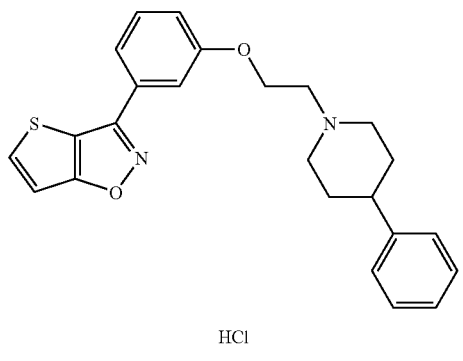

HCl

MDL 813930

Mix 3-[3-(2-bromo-ethoxy)-phenyl]-thieno[2,3-d]isoxazole (0.400 g, 1.23 mmol), potassium carbonate (0.345 g, 2.50 mmol), 4-phenylpiperidine (0.595 g, 3.69 mmol) and acetonitrile (5.0 mL) and heat at 65° C., overnight. Cool the reaction mixture and filter through a Waters Sep-Pak 1 g silica cartridge (ethyl acetate). Combine the appropriate fractions and concentrate to give a residue. Purify the residue by column (10 g silica) chromatography using a solvent mixture of 60% ethyl acetate in dichloromethane. Dissolve the free base in chloroform and acidify with ethereal hydrochloric acid and concentrate to a beige foam. Triturate the beige foam and recrystallize (methanol:ethyl acetate) to obtain the title compound as white crystals (0.366 g, 67%). Microanalysis (C, H, N) is consistent with the final, desired compound. mp=185–187° C.

Example 29

Preparation of [2-(3-thieno[2,3-d]isoxazol-3-yl-phenoxy)-ethyl]-(2-trifluoromethylbenzyl)-amine (Scheme I, Compound 1)

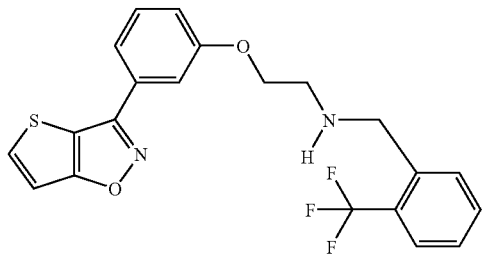

MDL 814359-001

The title compound is prepared from 3-[3-(2-bromo-ethoxy)-phenyl]-thieno[2,3-d]isoxazole (0.250 g, 0.771 mmol), potassium carbonate (0.205 g, 1.48 mmol), 2-(trifluoromethyl)benzylamine (0.676 mg, 3.86 mmol) and acetonitrile (4 mL) essentially as described above in example 18 except that the reaction is run overnight and the compound is purified by column using a solvent gradient of 5% ethyl acetate in dichloromethane to 10% methanol in ethyl acetate to give the title compound (0.311 g, 96% Yield). Purity by LC/MS (APCI)=99%, [M+H]$^+$=419.

Example 30–34

Examples 30–34 are prepared using techniques of parallel synthesis. Experimental conditions are described in detail in Example 18, with any variations in procedures being noted for Examples 30–34.

Example 30

Preparation of 3-[3-(2-piperidin-1-yl-ethoxy)-phenyl]-thieno[2,3-d]isoxazole (Scheme 1, Compound 1)

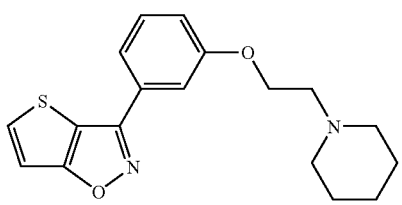

MDL 814356-001

The title compound is prepared from 3-[3-(2-bromo-ethoxy)-phenyl]-thieno[2,3-d]isoxazole, potassium carbonate, piperidine and acetonitrile essentially as described above in example 18 except that the reaction is run overnight and the compound is purified by column chromatography using a graded solvent mixture of 5% ethyl acetate in dichloromethane to 10% methanol in ethyl acetate. Purity by LC/MS (APCI)=98%, [M+H]$^+$=329.

Example 31

Preparation of (2,4-difluoro-benzyl)-[2-(3-thieno[2,3-d]isoxazol-3-yl-phenoxy)-ethyl]-amine (Scheme I, Compound 1)

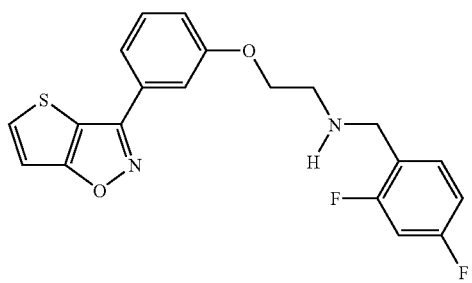

MDL 814357-001

The title compound is prepared from 3-[3-(2-bromo-ethoxy)-phenyl]-thieno[2,3-d]isoxazole, potassium carbonate, 2,4-difluorobenzylamine and acetonitrile essentially as described above in example 18 except that the reaction is run overnight and the compound is purified by column chromatography using a graded solvent mixture of 5% ethyl acetate in dichloromethane to 10% methanol in ethyl acetate. Purity by LC/MS (APCI)=98%, [M+H]$^+$=387.

Example 32

Preparation of (2,6-difluoro-benzyl)-[2-(3-thieno[2,3-d]isoxazol-3-yl-phenoxy)-ethyl]-amine (Scheme I, Compound 1)

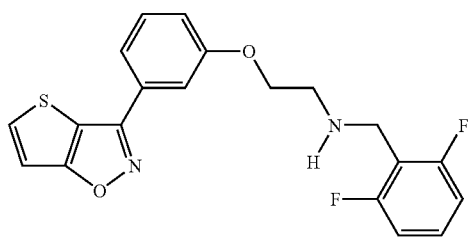

MDL 814358-001

The title compound is prepared from 3-[3-(2-bromo-ethoxy)-phenyl]-thieno[2,3-d]isoxazole, potassium carbonate, 2,6-difluorobenzylamine and acetonitrile essentially as described above in example 18 except that the reaction is run overnight and the compound is purified by column chromatography using a solvent gradient of 5% ethyl acetate in dichloromethane to 10% methanol in ethyl acetate. Purity by LC/MS (APCI)=99%, [M+H]$^+$=387.

Example 33

Preparation of adamantan-1-yl-[2-(3-thieno[2,3-d]isoxazol-3-yl-phenoxy)-ethyl]-amine (Scheme I, Compound 1)

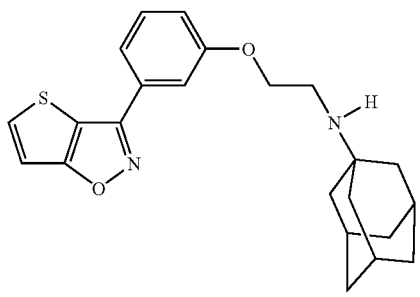

MDL 814355-001

The title compound is prepared from 3-[3-(2-bromo-ethoxy)-phenyl]-thieno[2,3-d]isoxazole, potassium carbonate, 1-adamantanamine and acetonitrile essentially as described above in example 18 except that the reaction is run overnight and the compound is purified by column chromatography using a graded solvent mixture of 5% ethyl acetate in DCM to 10% methanol in ethyl acetate. Purity by LC/MS (APCI)=97%, [M+H]$^+$=395.

Example 34

Preparation of [2-(3-thieno[2,3-d]isoxazol-3-yl-phenoxy)-ethyl]-(4-trifluoromethylbenzyl)-amine (Scheme I, Compound 1)

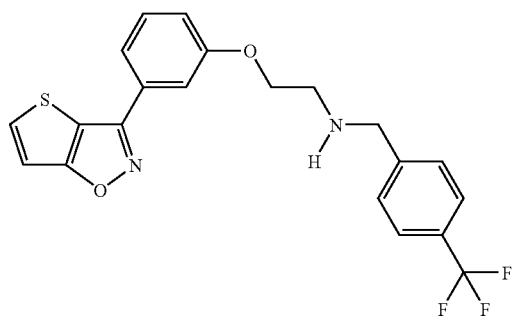

MDL 814360-001

The title compound is prepared from 3-[3-(2-bromo-ethoxy)-phenyl]-thieno[2,3-d]isoxazole, potassium carbonate, 4-(trifluoromethyl)benzylamine and acetonitrile essentially as described above in example 18 except that the reaction is run overnight and the compound is purified by column chromatography using a solvent gradient of 5% ethyl acetate in dichloromethane to 10% methanol in ethyl acetate. Purity by LC/MS (APCI)=98%, [M+H]$^+$=419.

Examples 35–39

Examples 35–39 are prepared using techniques of parallel synthesis. Experimental conditions are described in detail for Example 35, with any variations in procedures being noted for Examples 36–39.

Example 35

Preparation of (2-fluoro-benzyl)-[2-(3-thieno[2,3-d]isoxazol-3-yl-phenoxy)-ethyl]-amine (Scheme I, Compound 1)

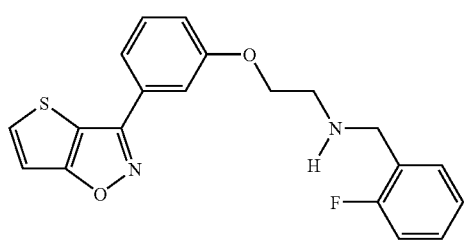

MDL 814224-001

Mix 3-[3-(2-bromo-ethoxy)-phenyl]-thieno[2,3-d]isoxazole (0.40 g, 1.23 mmol), potassium carbonate (0.341 g, 2.47 mmol), 2-fluorobenzylamine (0.626 g, 5.0 mmol) and acetonitrile (5.0 mL) and heat at 80° C., overnight. Cool the reaction mixture and filter through a Waters Sep-Pak 1 g silica cartridge (ethyl acetate). Combine the appropriate fractions and concentrate to give a residue. Purify the residue by column (10 g silica) chromatography using a solvent gradient of 40% ethyl acetate in heptane to 100% ethyl acetate to obtain the title compound (0.378 g, 83% Yield). Purity by LC/MS (APCI)=99%, [M+H]$^+$=369.

Example 36

Preparation of (2-chloro-benzyl)-[2-(3-thieno[2,3-d]isoxazol-3-yl-phenoxy)-ethyl]-amine (Scheme I, Compound 1)

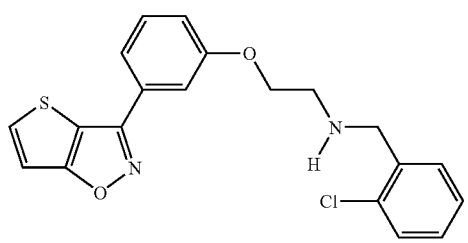

MDL 814225-001

The title compound is prepared from 3-[3-(2-bromo-ethoxy)-phenyl]-thieno[2,3-d]isoxazole, potassium carbonate, 2-chlorobenzylamine and acetonitrile essentially as described above in example 35. Purity by LC/MS (APCI)=99%, [M+H]$^+$=385.

Example 37

Preparation of (3-methoxy-benzyl)-[2-(3-thieno[2,3-d]isoxazol-3-yl-phenoxy)-ethyl]-amine (Scheme I, Compound 1)

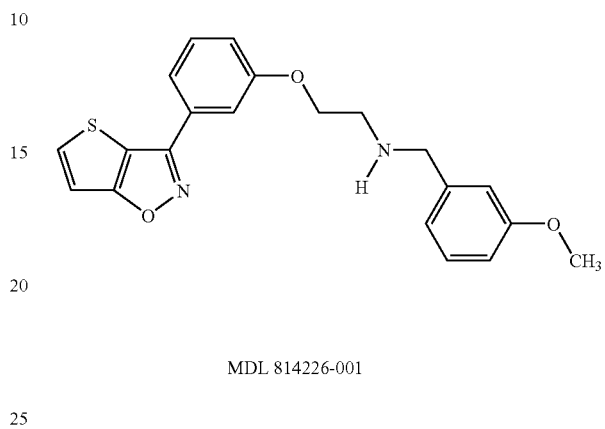

MDL 814226-001

The title compound is prepared from 3-[3-(2-bromo-ethoxy)-phenyl]-thieno[2,3-d]isoxazole, potassium carbonate, 3-methoxybenzylamine and acetonitrile essentially as described above in example 35, except that the column is eluted with a graded solvent mixture of 50% ethyl acetate in heptane to 100% ethyl acetate. Purity by LC/MS (APCI)=99%, [M+H]$^+$=381.

Example 38

Preparation of (3,4-difluoro-benzyl)-[2-(3-thieno[2,3-d]isoxazol-3-yl-phenoxy)-ethyl]-amine (Scheme I, Compound 1)

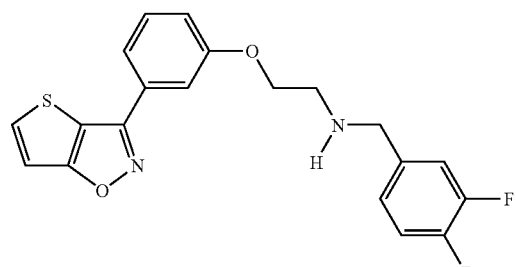

MDL 814227-001

The title compound is prepared from 3-[3-(2-bromo-ethoxy)-phenyl]-thieno[2,3-d]isoxazole, potassium carbonate, 3,4-difluorobenzylamine and acetonitrile essentially as described above in example 35. Purity by LC/MS (APCI)=100%, [M+H]$^+$=387.

Example 39

Preparation of indan-1-yl-[2-(3-thieno[2,3-d]isoxazol-3-yl-phenoxy)-ethyl)-amine (Scheme I, Compound 1)

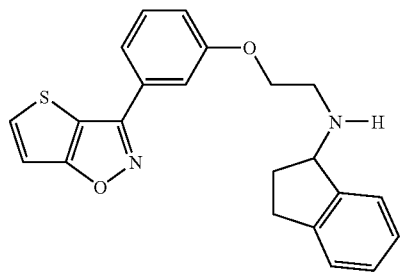

MDL 814228-001

The title compound is prepared from 3-[3-(2-bromoethoxy)phenyl]-thieno[2,3-d]isoxazole, potassium carbonate, 1-aminoindan and acetonitrile essentially as described above in example 35. Purity by LC/MS (APCI)=99%, [M+H]$^+$=377.

Examples 40–44

Examples 40–44 are prepared using techniques of parallel synthesis. Experimental conditions are described in detail for Example 40, with any variations in procedures being noted for Examples 41–44.

Example 40

Preparation of 3-{3-[2-(4-methyl-piperidin-1-yl)-ethoxy]-phenyl}-thieno[2,3-d]isoxazole (Scheme I, Compound 1)

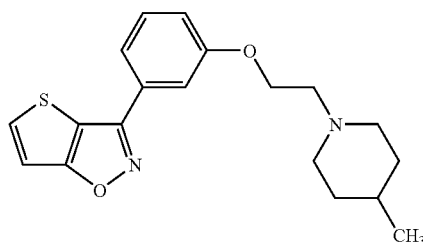

MDL 814790-001

Mix 3-[3-(2-bromo-ethoxy)-phenyl]-thieno[2,3-d]isoxazole (0.250 g, 0.77 mmol), potassium carbonate (0.22 g, 1.59 mmol), 4-methylpiperidine (0.382 g, 3.85 mmol) and acetonitrile (4.0 mL) and heat at 75° C., overnight. Cool the reaction mixture and filter through a Waters Sep-Pak 1 g silica cartridge (ethyl acetate). Combine the appropriate fractions and concentrate to give a residue. Purify the residue by column (10 g silica) chromatography using a solvent gradient of dichloromethane to 10% methanol in dichloromethane to obtain the title compound (0.254 g, 96% Yield) as an amber oil. Purity by LC/MS (APCI)=99%, [M+H]$^+$=343.

Example 41

Preparation of 3-{3-[2-(4-propyl-piperidin-1-yl)-ethoxy]-phenyl}-thieno[2,3-d]isoxazole (Scheme I, Compound 1)

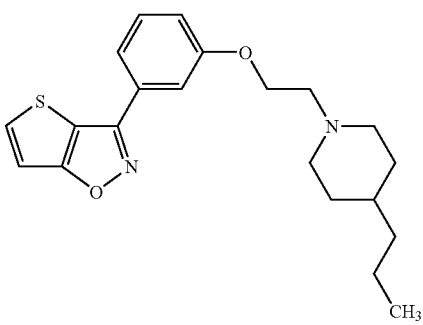

MDL 814791-001

The title compound is prepared from 3-[3-(2-bromo-ethoxy)-phenyl]-thieno[2,3-d]isoxazole, potassium carbonate, 4-N-propylpiperidine and acetonitrile essentially as described above in example 40. Purity by LC/MS (APCI)=96%, [M+H]$^+$=371.

Example 42

Preparation of 3-[3-(2-pyrrolidin-1-yl-ethoxy)-phenyl]-thieno[2,3-d]isoxazole (Scheme I, Compound 1)

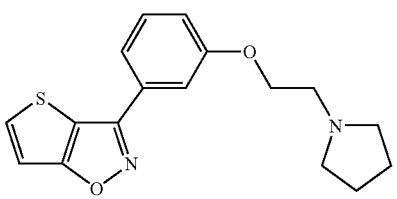

MDL 814793-001

The title compound is prepared from 3-[3-(2-bromo-ethoxy)-phenyl]-thieno[2,3-d]isoxazole, potassium carbonate, pyrrolidine and acetonitrile essentially as described above in example 40. Purity by LC/MS (APCI)=100%, [M+H]$^+$=315.

Example 43

Preparation of 3-[3-(2-azepan-1-yl-ethoxy)-phenyl]-thieno[2,3-d]isoxazole (Scheme I, Compound 1)

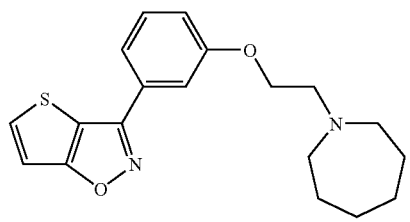

MDL 814794-001

The title compound is prepared from 3-[3-(2-bromo-ethoxy)-phenyl]-thieno[2,3-d]isoxazole, potassium carbonate, hexamethyleneimine and acetonitrile essentially as described above in example 40. Purity by LC/MS (APCI)= 99%, [M+H]$^+$=343.

Example 44

Preparation of 3-[3-(2-azocan-1-yl-ethoxy)-phenyl]-thieno[2,3-d]isoxazole (Scheme I, Compound 1)

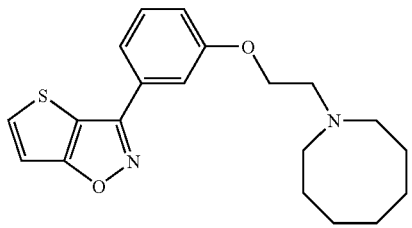

MDL 814795-001

The title compound is prepared from 3-[3-(2-bromo-ethoxy)-phenyl]-thieno[2,3-d]isoxazole, potassium carbonate, heptamethyleneimine and acetonitrile essentially as described above in example 40. Purity by LC/MS (APCI)= 99%, [M+H]$^+$=357.

Example 45

Preparation of benzyl-[2-(3-thieno[2,3-d]isoxazol-3-yl-phenoxy)-ethyl]-amine (Scheme I, Compound I)

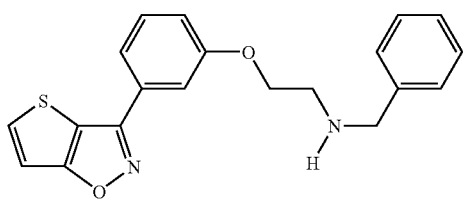

MDL 813644

The title compound is prepared from 3-[3-(2-bromo-ethoxy)-phenyl]-thieno[2,3-d]isoxazole, potassium carbonate, and benzylamine in two separate reactions using acetonitrile and 90% aqueous acetonitrile, respectively, essentially as described above in example 18 except that the reaction mixtures are filtered through 2 g of silica (ethyl acetate then dichloromethane). Combine and concentrate the appropriate fractions. Purify by column chromatography on silica gel. Elute the column with a step gradient of 50% ethyl acetate in heptane to 100% ethyl acetate to give the title compound (0.350 g, 81%). mp=60–63° C. Microanalysis (C, H, N) is consistent with the final compound.

Example 46

Preparation of 3-{3-[2-(4-phenyl-piperazin-1-yl)-ethoxy]-phenyl}-thieno[2,3-d]isoxazole (Scheme I, Compound I)

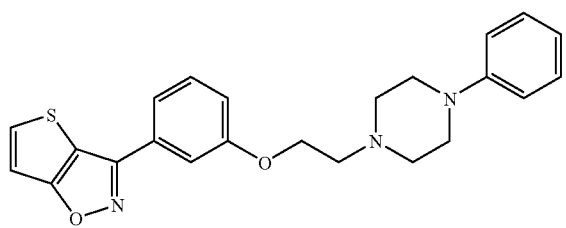

MDL 813840

The title compound is prepared from 3-[3-(2-bromo-ethoxy)-phenyl]-thieno[2,3-d]isoxazole, potassium carbonate, and N-phenylpiperazine essentially as described in example 27 except that the freebase is dried to give the title compound (330 mg, 66%). Mp=91–93° C. Microanalysis (C, H, N) is consistent with the final compound.

Example 47

Preparation of benzyl-[2-(3-thieno[2,3-d]isoxazol-3-yl-phenoxy)-ethyl]-amine hydrochloride (Scheme I, Compound 1)

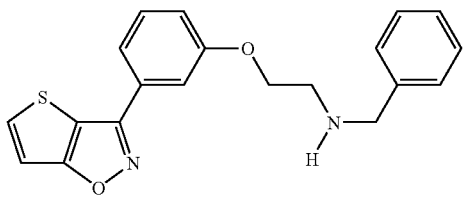

HCl

MDL 814008

The title compound is prepared from 3-[3-(2-bromo-ethoxy)-phenyl]-thieno[2,3-d]isoxazole, potassium carbonate, and benzylamine essentially as described in example 27 except for the following: The reaction is heated at 70° C., and the column is eluted with a step gradient of 75% ethyl acetate in heptane to 100% ethyl acetate. The free base is dissolved in ethanol/chloroform and acidified to give a white solid. Recrystallize the solid (methanol: ethyl acetate) to obtain the title compound as white powder (0.374 g, 62%). Mp=202–204° C. Microanalysis (C, H, N) is consistent with the final compound.

Example 48

Preparation of (4-methyl-benzyl)-[3-(3-thieno[2,3-d]isoxazol-3-yl-phenoxy)-propyl]-amine (Scheme I, Compound 1)

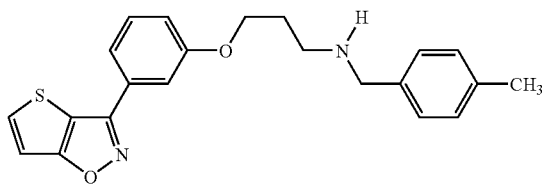

MDL 814229

Mix 3-[3-(3-bromo-propoxy)-phenyl]-thieno[2,3-d]isoxazole (0.400 g, 1.18 mmol), potassium carbonate (0.326 g, 2.36 mmol), 4-methylbenzylamine (0.606, 5.00 mmol) and acetonitrile (5.0 mL) and heat (75° C.), overnight. Cool the reaction mixture and filter through a Waters Sep-Pak 1 g silica cartridge (ethyl acetate). Combine the appropriate fractions and concentrate to give a residue. Dissolved residue in 50% ethyl acetate in dichloromethane and chromatograph on silica (10 g) using ethyl acetate to give the title compound (356 mg, 80% yield). Purity by LC/MS (APCI)= 98, $[M+H]^+$=379.

Example 49

Preparation of (2-chloro-benzyl)-[3-(3-thieno[2,3-d]isoxazol-3-yl-phenoxy)-propyl]-amine (Scheme I, Compound 1)

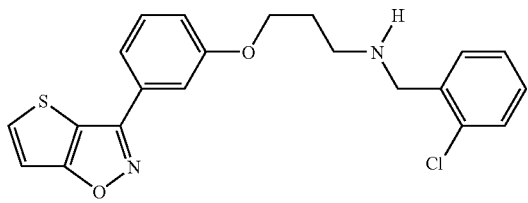

MDL 814230

The title compound is prepared from 3-[3-(3-bromo-propoxy)-phenyl]-thieno[2,3-d]isoxazole, potassium carbonate, 2-chlorobenzylamine and acetonitrile essentially as described above in example 48 except that the crude product is dissolve in DCM and purified by using a step gradient of 50% ethyl acetate in heptane, to 100% ethyl acetate. Purity by LC/MS (APCI)=98%, $[M+H]^+$=399.

Example 50

Preparation of (3-methoxy-benzyl)-[3-(3-thieno[2,3-d]isoxazol-3-yl-phenoxy)-propyl]-amine (Scheme I, Compound 1)

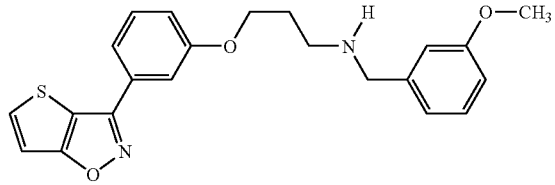

MDL 814231

The title compound is prepared from 3-[3-(3-bromo-propoxy)-phenyl]-thieno[2,3-d]isoxazole, potassium carbonate, 3-methoxybenzylamine and acetonitrile essentially as described above in example 48. Purity by LC/MS (APCI)= 93%, $[M+H]^+$=395.

Example 51

Preparation of (3,4-difluoro-benzyl)-[3-(3-thieno[2,3-d]isoxazol-3-yl-phenoxy)-propyl]-amine (Scheme I, Compound 1)

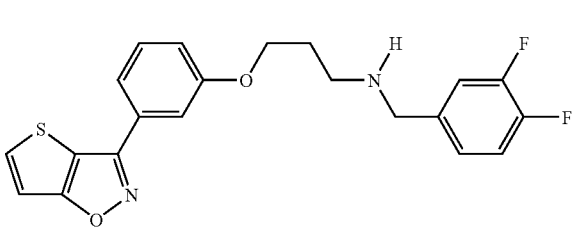

MDL 814232

The title compound is prepared from 3-[3-(3-bromo-propoxy)-phenyl]-thieno[2,3-d]isoxazole, potassium carbonate, 3,4-difluorobenzylamine and acetonitrile essentially as described above in example 48. Purity by LC/MS (APCI)= 98%, $[M+H]^+$=401.

Example 52

Preparation of indan-1-yl-[2-(3-thieno[2,3-d]isoxazol-3-yl-phenoxy)-propyl]-amine (Scheme I, Compound 1)

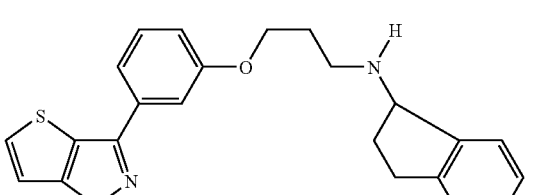

MDL 814233

The title compound is prepared from 3-[3-(3-bromo-propoxy)-phenyl]-thieno[2,3-d]isoxazole, potassium carbonate, 1-aminoindan, and acetonitrile essentially as described above in example 48. Purity by LC/MS (APCI)= 97%, $[M+H]^+$=391.

Example 53

Preparation of indan-2-yl-[3-(3-thieno[2,3-d]isoxazol-3-yl-phenoxy)-propyl]-amine

MDL 814234

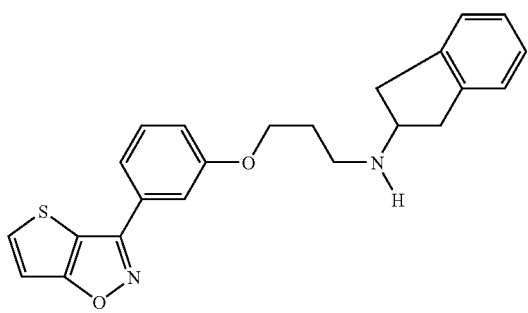

The title compound is prepared from 3-[3-(3-bromo-propoxy)-phenyl]-thieno[2,3-d]isoxazole, potassium carbonate, 2-aminoindan, and acetonitrile essentially as described above in example 48. Purity by LC/MS (APCI)=99%, [M+H]$^+$=391.

Example 54

Preparation of 2-[3-(3-thieno[2,3-d]isoxazol-3-yl-phenoxy)-propyl]-1,2,3,4-tetrahydroisoquinoline (Scheme I, Compound 1)

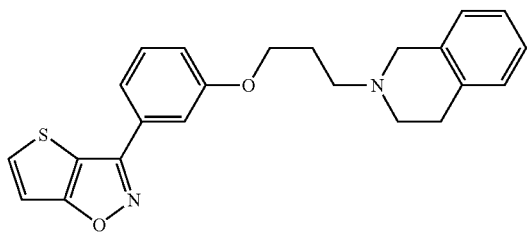

MDL 814235

The title compound is prepared from 3-[3-(3-bromo-propoxy)-phenyl]-thieno[2,3-d]isoxazole, potassium carbonate, 1,2,3,4-tetrahydroisoquinoline and acetonitrile essentially as described above in example 48 except that the crude product is dissolve in DCM and purified by using a step gradient of 50% ethyl acetate in heptane, to 100% ethyl acetate. Purity by LC/MS (APCI)=96%, [M+H]$^+$=391.

Example 55

Preparation of indan-2-yl-[2-(3-thieno[2,3-d]isoxazol-3-yl-phenoxy)-ethyl]-amine hydrochloride (Scheme I, Compound 1)

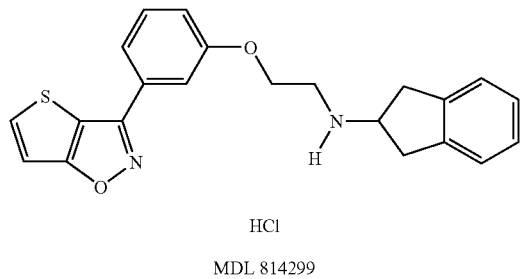

HCl

MDL 814299

The title compound is prepared from 3-[3-(2-bromo-ethoxy)-phenyl]-thieno[2,3-d]isoxazole, potassium carbonate, and 2-aminoindan essentially as described in example 27 except for the following: The column is eluted with a step gradient of 50% ethyl acetate in heptane to 100% ethyl acetate. The free base is dissolved in ethanol/chloroform and acidified to give a tan solid. The solid was recrystallized (methanol) to obtain the title compound as an off-white powder (0.295 g, 46%). Mp=214–218° C. Microanalysis (C, H, N) is consistent with the final compound.

Example 56

Preparation of adamantan-1-yl-[3-(3-thieno[2,3-d]isoxazol-3-yl-phenoxy)-propyl]-amine (Scheme I, Compound 1)

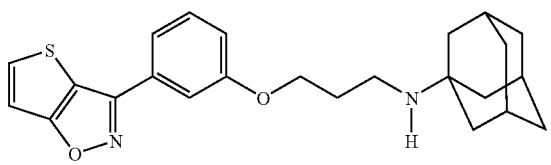

MDL 814762

Mix 3-[3-(3-bromo-propoxy)-phenyl]-thieno[2,3-d]isoxazole (0.250 g, 0.739 mmol), potassium carbonate (0.205 g, 1.48 mmol), 1-adamantanamine (0.560 g, 3.70 mmol) and acetonitrile (4.0 mL) and heat at 75° C., overnight. Cool the reaction mixture and filter through a Waters Sep-Pak (1 g) silica gel cartridge (ethyl acetate). Combine the appropriate fractions and concentrate to give a residue. Purify the residue by column (10 g silica) chromatography using a step gradient from 40% ethyl acetate in dichloromethane to 100% ethyl acetate to 20% methanol in ethyl acetate to give the title compound (132 mg, 44% yield). Purity by LC/MS (APCI)=98%, [M+H]$^+$=409.

Example 57

Preparation of 3-[3-(3-piperidin-1-yl-propoxy)-phenyl]-thieno[2,3-d]isoxazole (Scheme I, Compound 1)

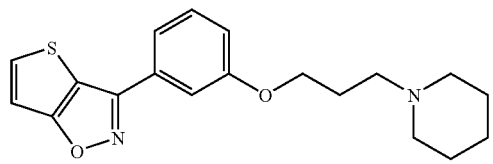

MDL 814763

The title compound is prepared from 3-[3-(3-bromo-propoxy)-phenyl]-thieno[2,3-d]isoxazole, potassium carbonate, piperidine, and acetonitrile essentially as described above in example 56. Purity by LC/MS (APCI)=98%, [M+H]$^+$=343.

Example 58

Preparation of (2,4-difluoro-benzyl)-[3-(3-thieno[2,3-d]isoxazol-3-yl-phenoxy)-propyl]-amine (Scheme I, Compound 1)

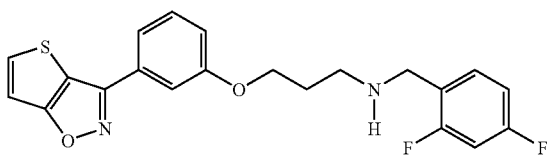

MDL 814764

The title compound is prepared from 3-[3-(3-bromo-propoxy)-phenyl]-thieno[2,3-d]isoxazole, potassium car-

Example 59

Preparation of (2,6-difluoro-benzyl)-[3-(3-thieno[2,3-d]isoxazol-3-yl-phenoxy)-propyl]-amine (Scheme I, Compound 1)

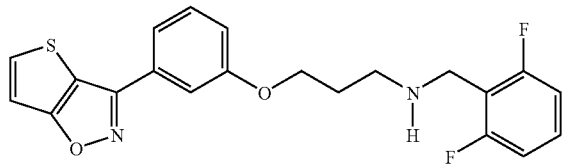

MDL 814765

The title compound is prepared from 3-[3-(3-bromopropoxy)-phenyl]-thieno[2,3-d]isoxazole, potassium carbonate, 2,6-difluorobenzylamine, and acetonitrile essentially as described above in example 56. Purity by LC/MS (APCI)= 97%, [M+H]+=401.

Example 60

Preparation of [3-(3-thieno[2,3-d]isoxazol-3-yl-phenoxy)-propyl]-(2-trifluoromethylbenzyl)-amine (Scheme I, Compound 1)

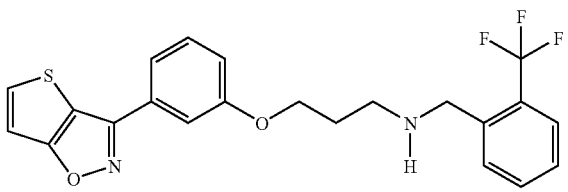

MDL 814766

The title compound is prepared from 3-[3-(3-bromopropoxy)-phenyl]-thieno[2,3-d]isoxazole, potassium carbonate, 2-(trifluoromethyl)benzylamine, and acetonitrile essentially as described above in example 56. Purity by LC/MS (APCI)=98%, [M+H]+=433.

Example 61

Preparation of [3-(3-thieno[2,3-d]isoxazol-3-yl-phenoxy)-propyl]-(4-trifluoromethylbenzyl)-amine (Scheme I, Compound 1)

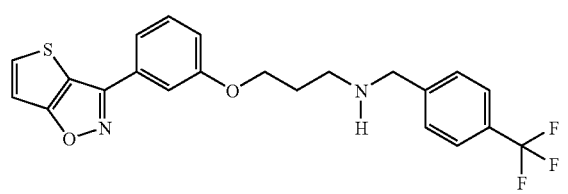

MDL 814767

The title compound is prepared from 3-[3-(3-bromopropoxy)-phenyl]-thieno[2,3-d]isoxazole, potassium carbonate, 4-(trifluoromethyl)benzylamine, and acetonitrile essentially as described above in example 56. Purity by LC/MS (APCI)=98%, [M+H]+=433.

Example 62

Preparation of [2-(3-thieno[2,3-d]isoxazol-3-yl-phenoxy)-ethyl]-thiophen-3-ylmethylamine hydrochloride (Scheme I, Compound 1)

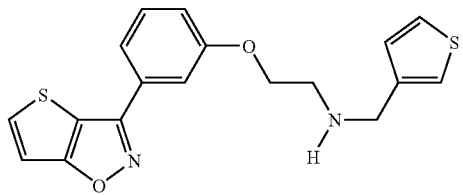

MDL 814223

Dissolve the product from example 24, [2-(3-thieno[2,3-d]isoxazol-3-yl-phenoxy)-ethyl]-thiophen-3-ylmethylamine (205 mg, 0.575 mmol), in ethanol (5 mL) and acidify with ethereal-HCL. Dilute solution with ether (10 mL) and age for 3 h at room temperature to give 180 mg of the title compound as a tan powder. mp=202–204° C. Microanalysis (C, H, N) is consistent with the final, desired compound.

Receptor Binding Assay $D_4$ receptor-binding affinities of the compounds were evaluated according to their ability to reduce binding of $^3$H-spiperone as compared to the reference compound clozapine. The potency of the test compound to reduce $^3$H-spiperone binding directly correlated to its binding affinity for the receptor.

$D_4$ Receptor Preparation

HEK 298 (human embryonic kidney) cells stably transfected with human $D_4$ receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 min, 5000 rpm (GS3 rotor) and the pellets quickly frozen in liquid nitrogen and stored at −80° C. until used in binding assay. When used in the assay, cells were thawed on ice for 20 min and then 10 mL of incubation buffer (50 mM Tris, 1 mM EDTA, 4 mM $MgCl_2$, 5 mM KCl, 1.5 mM $CaCl_2$, 120 mM NaCl, pH 7.4) was added. The cells were then vortexed to resuspend pellet and homogenized with a Kinematica, CH-6010 Kriens-LU, homogenizer for 15 seconds at setting 7. Concentration of receptor protein was determined using the Pierce BCA assay.

Total Spiperone Binding Assay

The incubation was started by the addition of 100 μl (50 μg protein) membrane homogenate to a solution of 300 μl incubation buffer and 100 μl (0.25 nM final conc.) $^3$H-spiperone (90 Ci/mmol, Amersham, diluted in borosilicate glass vial) in 96-well polypropylene plates (1 mL per well). The plates were vortexed and incubated at room temperature for 90 minutes. The binding reaction was stopped by filtering using a Packard Harvester. The samples were filtered under vacuum over glass fibre filter plates (Whatman GF/B) pre-soaked for 2 hours in 0.3% polyethylenimine (PEI) in 50 mM Tris buffer (pH 7.4). The filters were then washed 6 times with 7 mL ice cold 50 mM Tris buffer (pH 7.4). The filter plates were dried overnight and 35 μl of Microscint-O (Packard) was added. The plates were sealed and counted in the Packard Top Count (3 minutes per well).

Non-Specific Binding Assay for $D_4$

The incubation was started by the addition of 100 μl (50 μg protein) membrane homogenate to a solution of 200 μl incubation buffer, 100 μl $^3$H-spiperone (90 Ci/mmol, Amersham, diluted in borosilicate glass vial to 0.25 nM final conc.) and 100 μl (30 μM final conc.) of fresh dopamine (Research Biochemicals Inc., light protected and dissolved in incubation buffer) in 96-well polypropylene plates (1 mL per well). The plates were vortexed and incubated at room temperature for 90 minutes at which time the binding reaction was stopped by filtering. The filters were washed and counted using the same procedure as in the total binding assay described above to give the non-specific binding value (NSB).

Displacement Binding Assay

The incubation was started by the addition, in 96-well polypropylene plates (1 mL per well), of 100 μl (50 μg protein) membrane homogenate to a solution of 200 μl incubation buffer, 100 μl (0.25 nM final conc.) $^3$H-spiperone (90 Ci/mmol, Amersham, diluted in borosilicate glass vial) and 100 μl of test compound that was prepared from 1 mM stock dissolved in DMSO and stored at −20° C. in polypropylene cryogenic storage vials until dilution in incubation buffer in 96-well polypropylene plates. The plates were vortexed and incubated at room temperature for 90 minutes at which time the binding reaction was stopped by filtering. The filters were washed and counted using the same procedure as in the total binding assay described above to give the displacement binding value ($B_D$).

Calculations

The test compounds were initially assayed at 1 and 0.1 μM and then at a range of concentrations chosen such that the middle dose would cause about 50% inhibition of $^3$H-spiperone binding. Specific binding in the absence of test compound ($B_0$) was the difference of total binding ($B_T$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of %B/$B_0$ vs concentration of test compound.

Ki was calculated by the Cheng and Prustoff transformation:

$$Ki=IC_{50}/(1+[L]/K_D)$$

where [L] is the concentration of $^3$H-spiperone used in the assay and $K_D$ is the dissociation constant of $^3$H-spiperone determined independently under the same binding conditions.

MK-801 Stereotypy in Mice

Mk-801 dose-dependently induces characteristic stereotypy marked by locomotion and falling behavior. This MK-801 induced behavior can be antagonized by novel neuroleptic agents. This assay can also assess time course effects following drug administration.

CD-1 or C57 male mice are individually placed in activity boxes (8 mice/drug) and allowed to acclimate for 60 minutes. The mice are then administered test compounds either i.p., s.c., or p.o., at 15, 30, or 60 minutes prior to MK-801 (0.2 mg/kg) administration. Mice are observed for the presence of locomotion and falling behaviors 15 minutes following MK-801. For the duration of action studies the test compounds are administered i.p., s.c., or p.o., at 30, 60, 120, 180, and 240 minutes prior to MK-801 administration. $ED_{50}$ values and 95% confidence limits are calculated by Litchfield and Wilcoxon method.

The following table contains information about the preparation of compounds within the scope of the present invention. The Example Number (column 3) refers to an exact or analogous procedure that may be used to prepare the Compound Number (column 1).

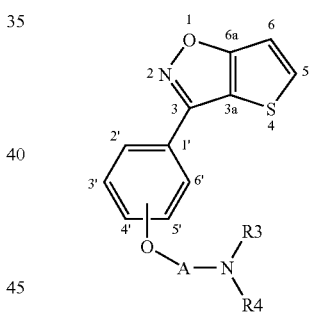

| Cmpd. No. | MDL No. | Example No. | A | N(R)3(R)4 | Number of position of oxygen substitution | $D_4$ RBA $K_i$ (μM) | $D_4$ RBA % Inhibition (@ 1 μM) | Antag. of MK 801 Stereotypy In Vivo Method | Antag. of MK 801 Stereotypy % Inhib. @ 20 mg/kg | In Vivo ED50 (mg/kg) |
|---|---|---|---|---|---|---|---|---|---|---|
| 1 | 813221 | 4A | 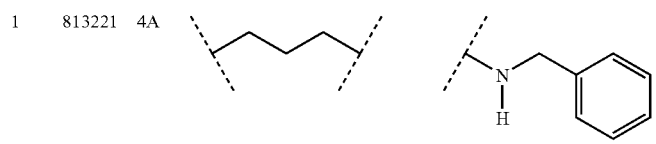 | | 3' | 0.012 | | PO | | 14.61 |

-continued
| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 2 | 813518 | 4 | 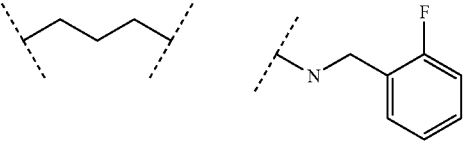 | 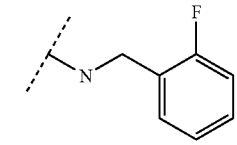 | 3' | 0.062 | | | | |
| 3 | 813519 | 5 | 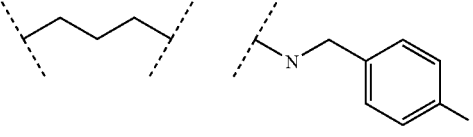 | 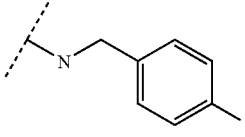 | 3' | 0.017 | | PO | 37.5 | |
| 4 | 813520 | 6 | 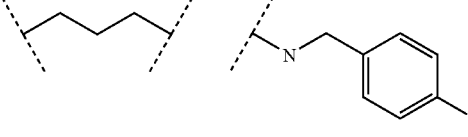 | 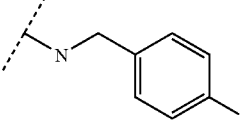 | 3' | 0.045 | | | | |
| 5 | 813521 | 7 | 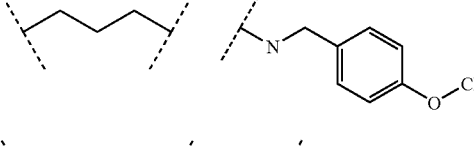 | 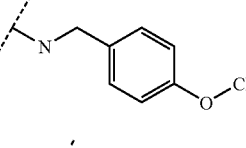 | 3' | 0.092 | | | | |
| 6 | 813522 | 8 |  | 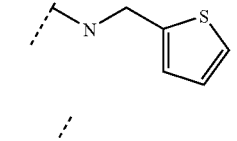 | 3' | 0.027 | | | | |
| 7 | 813523 | 9 |  | 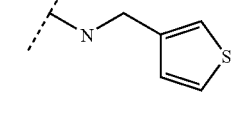 | 3' | 0.018 | | PO | 75 | |
| 8 | 813524 | 10 | 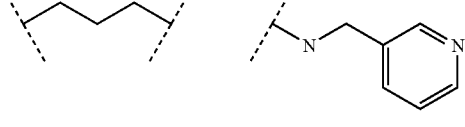 | 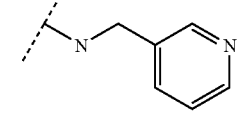 | 3' | 0.076 | | | | |
| 9 | 813525 | 11 | 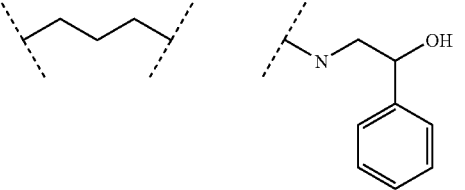 | 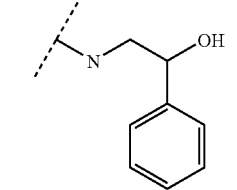 | 3' | | 73 | | | |
| 10 | 813526 | 12 | 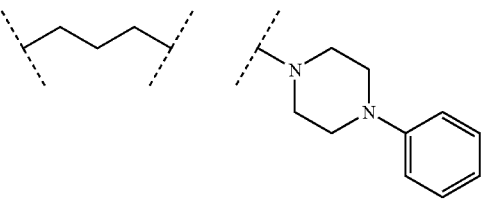 | 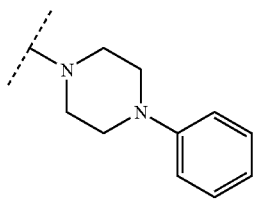 | 3' | | 95 | | | |

-continued

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 11 | 813527 | 13 | (pentyl linker) | piperazine-(4-fluorophenyl) | 3' | | 91 | | | |
| 12 | 813528 | 14 | (pentyl linker) | piperazine-(2-fluorophenyl) | 3' | | 94 | | | |
| 13 | 813529 | 15 | (pentyl linker) | piperazine-(2-pyrimidinyl) | 3' | 0.055 | | IP | 37.5 | |
| 14 | 813530 | 16 | (pentyl linker) | NH-CH₂-(4-sulfamoylphenyl) | 3' | | 60 | | | |
| 15 | 813531 | 17 | (pentyl linker) | NH-CH₂CH₂-(4-sulfamoylphenyl) | 3' | | 65 | | | |
| 16 | 813644 | 45 | (butyl linker) | NH-CH₂-phenyl | 3' | 0.0076 | | PO | | |

-continued

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 17 | 813728 | 19 | (butyl linker) | -NH-CH₂-C₆H₄-4-F | 3' | 0.012 | | PO | 62.5 | 14.14 |
| 18 | 813729 | 20 | (butyl linker) | -NH-CH₂-C₆H₄-4-Cl | 3' | 0.034 | | PO | 37.5 | |
| 19 | 813730 | 21 | (butyl linker) | -NH-CH₂-C₆H₄-3-F | 3' | 0.015 | | PO | 75 | |
| 20 | 813731 | 22 | (butyl linker) | -NH-CH₂-C₆H₄-4-CH₃ | 3' | 0.00527 | | PO | 37.5 | |
| 21 | 813732 | 18 | (butyl linker) | -NH-CH₂-C₆H₄-2-OCH₃ | 3' | 0.0142 | | | | |
| 22 | 813733 | 23 | (butyl linker) | -NH-CH₂-C₆H₃-3,4-Cl₂ | 3' | | 99 | | | |
| 23 | 813734 | 24 | (butyl linker) | -NH-CH₂-(3-thienyl) | 3' | 0.0082 | | | | |
| 24 | 813735 | 25 | (butyl linker) | -NH-CH₂-(2-thienyl) | 3' | | 95 | | | |
| 25 | 813736 | 26 | (butyl linker) | -NH-CH₂-(3-pyridyl) | 3' | | 93 | | | |

-continued

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 26 | 813808 | 3 | (N-benzyl pyrrolidin-3-yl) | — | 3' | | 92 | | | |
| 27 | 813809 | 3 | (N-benzyl pyrrolidin-3-yl) | — | 3' | | 89 | | | |
| 28 | 813840 | 46 | propylene | 4-phenylpiperazin-1-yl | 3' | | 78 | | | |
| 29 | 813841 | 27 | propylene | 1,2,3,4-tetrahydroisoquinolin-2-yl | 3' | | 60 | | | |
| 30 | 813930 | 28 | propylene | 4-phenylpiperidin-1-yl | 3' | | 68 | | | |
| 31 | 814008 | 47 | propylene | N-benzylamino | 3' | | 100* | PO | | 37.5 |

-continued

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 32 | 814009 | 1 | | N-CH₂-(3-fluorophenyl), NH | 3' | 0.0105* | | PO | 62.5 | |
| 33 | 814223 | 62 | | N-CH₂-(thiophen-3-yl), NH | 3' | 0.015* | | | | |
| 34 | 814224 | 35 | | N-CH₂-(2-fluorophenyl), NH | 3' | | 93 | | | |
| 35 | 814225 | 36 | | N-CH₂-(2-chlorophenyl), NH | 3' | | 88 | | | |
| 36 | 814226 | 37 | | N-CH₂-(3-methoxyphenyl), NH | 3' | 0.013 | | | | |
| 37 | 814227 | 38 | | N-CH₂-(3,4-difluorophenyl), NH | 3' | 0.032 | | | | |
| 38 | 814228 | 39 | | N-(indan-1-yl), NH | 3' | | 95 | | | |
| 39 | 814229 | 48 | | N-CH₂-(4-methylphenyl), NH | 3' | 0.020 | | | | |

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 40 | 814230 | 49 | | 2-chlorobenzyl-NH- | 3' | | 89 | | | |
| 41 | 814231 | 50 | | 3-methoxybenzyl-NH- | 3' | 0.044 | | | | |
| 42 | 814232 | 51 | | 3,4-difluorobenzyl-NH- | 3' | 0.047 | | | | |
| 43 | 814233 | 52 | | indan-1-yl-NH- | 3' | | 94 | | | |
| 44 | 814234 | 53 | | indan-2-yl-NH- | 3' | | 96 | | | |
| 45 | 814235 | 54 | | tetrahydroisoquinolin-2-yl | 3' | | 52 | | | |
| 46 | 814299 | 55 | | indan-2-yl-NH- | 3' | 0.0361 | | | | |
| 47 | 814355 | 33 | | adamantyl-NH- | 3' | 0.023 | | | | |
| 48 | 814356 | 30 | | piperidin-1-yl | 3' | | 83 | | | |

-continued

| Cmpd. No. | MDL No. | Example No. | A | N(R)₃(R)₄ | Number of position of oxygen substitution | $D_4$ RBA $K_i$ ($\mu M$) | $D_4$ RBA % Inhibition (@ 1 $\mu M$) | In Vivo Method | Antag. of MK 801 Stereotypy % Inhib. @ 20 mg/kg | In Vivo ED50 (mg/kg) |
|---|---|---|---|---|---|---|---|---|---|---|
| 49 | 814357 | 31 | (propyl linker) | 2,4-difluorobenzyl-NH- | 3' | | 95 | | | |
| 50 | 814358 | 32 | (propyl linker) | 2,6-difluorobenzyl-NH- | 3' | | 65 | | | |
| 51 | 814359 | 29 | (propyl linker) | 2-(trifluoromethyl)benzyl-NH- | 3' | | 58 | | | |
| 52 | 814360 | 34 | (propyl linker) | 4-(trifluoromethyl)benzyl-NH- | 3' | | 96 | | | |
| 53 | 814762 | 56 | (butyl linker) | 1-adamantyl-NH- | 3' | | 94 | | | |
| 54 | 814763 | 57 | (butyl linker) | piperidinyl | 3' | | 94 | | | |
| 55 | 814764 | 58 | (butyl linker) | 2,4-difluorobenzyl-NH- | 3' | | 92 | | | |

-continued

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 56 | 814765 | 59 | | 2,6-difluorobenzylamine | 3' | | 64 | | | |
| 57 | 814766 | 60 | | 2-(trifluoromethyl)benzylamine | 3' | | 46 | | | |
| 58 | 814767 | 61 | | 4-(trifluoromethyl)benzylamine | 3' | | 77 | | | |
| 59 | 814790 | 40 | | 4-methylpiperidine | 3' | | 90 | | | |
| 60 | 814791 | 41 | | 4-ethylpiperidine | 3' | | 82 | | | |
| 61 | 814793 | 42 | | pyrrolidine | 3' | | 41 | | | |
| 62 | 814794 | 43 | | azepane | 3' | | 90 | | | |
| 63 | 814795 | 44 | | azocane | 3' | | 54 | | | |

*indicates HCl salt.

The invention claimed is:

1. A compound of Formula I:

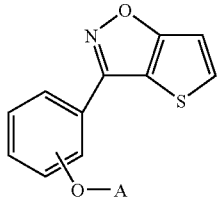

Formula I a pharmaceutically acceptable salt or stereoisomer thereof, wherein
A is $C_{2-3}$ alkylene-N($R_1$)($R_2$) or 1-(phenylmethyl)-pyrrolidin-3-yl;
$R_1$ is $(CH_2)_nQ$, $CH_2CH(OH)Q$, $CH(CH_3)Q$, 1,2,3,4-tetrahydronaphthyl, indanyl, or adamantyl, wherein
Q is thienyl, phenyl, furanyl, naphthyl, pyridyl, indolyl, indazolyl, cyclohexyl, 1,2-methylenedioxyphenyl, cyclohexenyl, 1H-pyrazolo[4,3-c]pyridyl; and
Q is optionally substituted with one or two moieties independently selected from halo, $C_{1-6}$alkyl, $C_{1-6}$ alkoxy, hydroxy, $S(O)_2NH_2$, trifluoromethyl, or cyano, and
n is 1 or 2;
$R_2$ is H or $C_{1-6}$ alkyl; or
$R_1$ and $R_2$, together with the nitrogen atom to which $R_1$ and $R_2$ are attached, form 4,5,6,7-tetrahydrothieno[3,2-c] pyridinyl, 1,4-dioxa-8-azo-spiro[4.5]decanyl, piperazinyl, morpholinyl, piperidinyl, pyrrolidinyl, azocanyl, azepanyl, 1,2,3,4-tetrahydroisoquinolinyl, 1,2,3,4-tetrahydro-1H-β-carbolinyl, or 8-aza-bicyclo[3.2.1]octanyl, each of which may be mono- or independently di-substituted with halo, $C_{1-6}$ alkyl, $C_{1-6}$ alkoxy, C(O)phenyl, OH, CN, O-phenyl or $(CH_2)_mZ$,
Z is benzisoxazolyl, indazolyl, benzisothiazolyl, benzthienyl, pyrimidinyl, pyridyl, 1,2-methylenedioxyphenyl, or phenyl, and
Z, CH(OH)phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$, or cyano, and
m is 0 or 1.

2. A compound according to claim 1 wherein $R_1$ and $R_2$, together with the nitrogen atom to which $R_1$ and $R_2$ are attached, form piperazinyl.

3. The compound according to claim 2 which is 3-{3-[3-(4-pyrimidin-2-yl-piperazin-1- yl)-propoxy]-phenyl}-thieno[2,3-d]isoxazole.

4. The compound according to claim 2 which is 3-{3-[3-(4-phenyl-piperazin-1-yl)-propoxy]-phenyl}-thieno[2,3-d]isoxazole.

5. The compound according to claim 2 which is 3-(3-{3-[4(4-fluoro-phenyl)-piperazin-1-yl]-propoxy}-phenyl)-thieno[2,3-d]isoxazole.

6. The compound according to claim 2 which is 3-(3-{3-[4-(2-fluoro-phenyl)-piperazin-1-yl]-propoxy}-phenyl)-thieno[2,3-d]isoxazole.

7. The compound according to claim 2 which is 3-{3-[2-(4-phenyl-piperazin-1-yl)-ethoxy]-phenyl}-thieno[2,3-d]isoxazole.

8. A compound according to claim 1 wherein $R_1$ is indanyl.

9. The compound according to claim 8 which is indan-2-yl-[2-(3-thieno[2,3-d]isoxazol-3-yl-phenoxy)-ethyl]-amine.

10. The compound according to claim 8 which is indan-1-yl-[2(3-thieno[2,3-d)isoxazol-3-yl-phenoxy)-ethyl]-amine.

11. The compound according to claim 8 which is indan-1-yl-[2-(3-thieno[2,3-d]isoxazol-3-yl-phenoxy)-propyl]-amine.

12. The compound according to claim 8 which is indan-2-yl-[3-(3-thieno[2,3-d]isoxazol-3-yl-phenoxy)-propyl]-amine.

13. A compound according to claim 1, wherein $R_1$ and $R_2$ together with the nitrogen atom to which $R_1$ and $R_2$ are attached, form 1,2,3,4-tetrahydroisoquinolinyl.

14. The compound according to claim 13 which is 2-[2-(3-thieno[2,3-d]isoxazol-3-yl-phenoxy)-ethyl]-1,2,3,4-tetrahydro-isoquinoline.

15. The compound according to claim 13 which is 2-[3-(3-thieno[2,3-d]isoxazol-3-yl-phenoxy)-propyl]-1,2,3,4-tetrahydro-isoquinoline.

16. A compound according to claim 1 wherein $R_1$ and $R_2$, together with the nitrogen atom to which $R_1$ and $R_2$ are attached, form azepanyl.

17. The compound according to claim 16 which is 3-[3-(2-azepan-1-yl-ethoxy)-phenyl]-thieno[2,3-d]isoxazole.

18. A compound according to claim 1 wherein $R_1$ is adamantyl.

19. The compound according to claim 18 which is adamantan-1-yl-[3-(3-thieno[2,3-d]isoxazol-3-yl-phenoxy)-propyl]-amine.

20. The compound according to claim 18 which is adamantan-1-yl-[2-(3-thieno[2,3-d]isoxazol-3-yl-phenoxy)-ethyl]-amine.

21. A compound according to claim 1 wherein
Q is thienyl, phenyl, or pyridyl, or
$R_1$ and $R_2$, together with the nitrogen atom to which $R_1$ and $R_2$ are attached, form morpholinyl, piperidinyl, pyrrolidinyl, or azocanyl.

22. The compound according to claim 21 which is 1-phenyl-2-[3-(3-thieno[2,3-d]isoxazol-3-yl-phenoxy)-propylamino]-ethanol.

23. The compound according to claim 21 which is 4-{2-[3-(3-thieno[2,3-d]isoxazol-3-yl-phenoxy)-propylamino]-ethyl}-benzenesulfonamide.

24. A compound according to claim 1 wherein A is
$C_{2-3}$alkylene-N($R_1$)($R_2$);
$R_1$ is $(CH_2)nQ$;
n is 1;
$R_2$ is H;
Q is thienyl, phenyl, or pyridyl; or
$R_1$ and $R_2$, together with the nitrogen atom to which $R_1$ and $R_2$ are attached, form morpholinyl, piperidinyl, pyrrolidinyl, or azocanyl.

25. The compound according to claim 24 wherein Q is thienyl.

26. The compound of claim 25 which is [3-(3-thieno[2,3-d]isoxazol-3-yl-phenoxy)-propyl]-thiophen-2-ylmethyl-amine.

27. The compound of claim 25 which is [2-(3-thieno[2,3-d]isoxazol-3-yl-phenoxy)-ethyl]-thiophen-2-ylmethyl-amine.

28. The compound of claim 25 which is [2-(3-thieno[2,3-d]isoxazol-3-yl-phenoxy)-ethyl]-thiophen-3-ylmethyl-amine.

29. The compound of claim 25 which is [3-(3-thieno[2,3-d]isoxazol-3-yl-phenoxy)-propyl]-thiophen-3-ylmethyl-amine.

30. A compound according to claim 24 wherein Q is phenyl.

31. The compound according to claim 30 which is benzyl-[3-(3-thieno[2,3-d]isoxazol-3-yl-phenoxy)-propyl]-amine.

32. The compound of claim 30 which is benzyl-[2-(3-thieno[2,3-d]isoxazol-3-yl-phenoxy)-ethyl]-amine.

33. The compound of claim 30 which is (2-methoxy-benzyl)-[2-(3-thieno[2,3-d]isoxazol-3-yl-phenoxy)-ethyl]-amine.

34. The compound of claim 30 which is (3-fluoro-benzyl)-[2-(3-thieno[2,3-d]isoxazol-3-yl-phenoxy)-ethyl]-amine.

35. The compound of claim 30 which is (2,&difluoro-benzyl)-[2-(3-thieno[2,3-d]isoxazol-3-yl-phenoxy)-ethyl]-amine.

36. The compound of claim 30 which is (2,6-difluoro-benzyl)-[3-(3-thieno[2,3-d]isoxazol-3-yl-phenoxy)-propyl]-amine.

37. The compound of claim 30 which is (2-fluoro-benzyl)-[3-(3-thieno[2,3-d]isoxazol-3-yl-phenoxy)-propyl]-amine.

38. The compound of claim 30 which is (4-fluoro-benzyl)-[3-(3-thieno[2,3-d]isoxazol-3-yl-phenoxy)-propyl)-amine.

39. The compound of claim 30 which is (4-chloro-benzyl)-[3-(3-thieno[2,3-d]isoxazol-3-yl-phenoxy)-propyl]-amine.

40. The compound of claim 30 which is (4-methoxy-benzyl)-[3-(3-thieno[2,3-d]isoxazol-3-yl-phenoxy)-propyl]-amine.

41. The compound of claim 30 which is 4-{[3-(3-thieno[2,3-d]isoxazol-3-yl-phenoxy)-propylamino]-methyl}-benzenesulfonamide.

42. The compound of claim 30 which is (4-chloro-benzyl)-[2-(3-thieno[2,3-d]isoxazol-3-yl-phenoxy)-ethyl]-amine.

43. The compound of claim 30 which is (4-methyl-benzyl)-[2-(3-thieno[2,3-d]isoxazol-3-yl-phenoxy)-ethyl]-amine.

44. The compound of claim 30 which is (3,4-dichloro-benzyl)-[2-(3-thieno[2,3-d]isoxazol-3-yl-phenoxy)-ethyl]-amine.

45. The compound of claim 30 which is (2,4-difluoro-benzyl)-[2-(3-thieno[2,3-d]isoxazol-3-yl-phenoxy)ethyl]-amine.

46. The compound of claim 30 which is [2-(3-thieno[2,3-d]isoxazol-3-yl-phenoxy)-ethyl]-(4-trifluoromethyl-benzyl)-amine.

47. The compound of claim 30 which is (2-fluoro-benzyl)[2-(3-thieno[2,3-d]isoxazol-3-yl-phenoxy)-ethyl]-amine.

48. The compound of claim 30 which is 2-chloro-benzyl)-[2-(3-thieno[2,3-d]isoxazol-3-yl-phenoxy)-ethyl]-amine.

49. The compound of claim 30 which is (3-methoxy-benzyl)-[2-(3-thieno[2,3-d]isoxazol-3-yl-phenoxy)-ethyl]-amine.

50. The compound of claim 30 which is (3,4-difluoro-benzyl)-[2-(3-thieno[2,3-d]isoxazol-3-yl-phenoxy)-ethyl]-amine.

51. The compound of claim 30 which is (4-methyl-benzyl)-[3-(3-thieno[2,3-d]isoxazol-3-yl-phenoxy)-propyl]-amine.

52. The compound of claim 30 which is (2-chloro-benzyl)-[3-(3-thieno[2,3-d]isoxazol-3-yl-phenoxy)-propyl]-amine.

53. The compound of claim 30 which is (3-methoxy-benzyl)-[3-(3-thieno[2,3-d]isoxazol-3-yl-phenoxy]propyl]-amine.

54. The compound of claim 30 which is (3,4-difluoro-benzyl)-[3-(3-thieno[2,3-d]isoxazol-3-yl-phenoxy)-propyl]-amine.

55. The compound of claim 30 which is (2,4-difluoro-benzyl)-3-(3-thieno[2,3-d]isoxazol-3-yl-phenoxy)-propyl]-amine.

56. The compound of claim 30 which is [3-(3-thieno[2,3-d]isoxazol-3-yl-phenoxy)-propyl]-(2-trifluoromethyl-benzyl)-amine.

57. The compound of claim 30 which is [3-(3-thieno[2,3-d]isoxazol-3-yl-phenoxy)-propyl]-(4-trifluoromethyl-benzyl)-amine.

58. The compound of claim 30 which is (4-fluoro-benzyl)-[2-(3-thieno[2,3-d]isoxazol-3-yl-phenoxy)-ethyl]-amine.

59. The compound of claim 30 which is [2-(3-thieno[2,3-d]isoxazol-3-yl-phenoxy)-ethyl]-(2-trifluoromethyl-benzyl)-amine.

60. The compound of claim 30 which is benzyl-[2-(3-thieno[2,3-d]isoxazol-3-yl-phenoxy)-ethyl]-amine.

61. A compound according to claim 24 wherein Q is pyridyl.

62. The compound of claim 61 which is pyridin-3-ylmethyl-[2-(3-thieno[2,3-d]isoxazol-3-yl-phenoxy)-ethyl]-amine.

63. The compound of claim 61 which is pyridin-3-ylmethyl-[3-(3-thieno[2,3-d]isoxazol-3-yl-phenoxy)-propyl]-amine.

64. A compound according to claim 24 wherein $R_1$ and $R_2$, together with the nitrogen atom to which $R_1$ and $R_2$ are attached, form piperidinyl.

65. The compound according to claim 64 which is 3-[3-(3-piperidin-1-yl-propoxy)-phenyl]-thieno[2,3-d]isoxazole.

66. The compound of claim 64 which is 3-{3-[2-(4-phenyl-piperidin-1-yl)-ethoxy]phenyl}-thieno[2,3-d]isoxazole.

67. The compound of claim 64 which is 3-[3-(2-piperidin-1-yl-ethoxy)-phenyl]-thieno[2,3-d]isoxazole.

68. The compound of claim 64 which is 3-{3-[2-(4-methyl-piperidin-1-yl)-ethoxy]-phenyl}-thieno[2,3-d]isoxazole.

69. The compound of claim 64 which is 3-{3-[2-(4-propyl-piperidin-1-yl)-ethoxy]phenyl}-thieno[2,3-d]isoxazole.

70. A compound according to claim 24 wherein $R_1$ and $R_2$, together with the nitrogen atom to which $R_1$ and $R_2$ are attached, form pyrrolidinyl.

71. The compound of claim 70 which is 3-[3-(2-pyrrolidin-1-yl-ethoxy)-phenyl]-thieno[2,3-d]isoxazole.

72. A compound according to claim 24 wherein $R_1$ and $R_2$, together with the nitrogen atom to which $R_1$ and $R_2$ are attached, form azocanyl.

73. The compound of claim 72 which is 3-[3-(2-azocan-1-yl-ethoxy)-phenyl]-thieno[2,3-d]isoxazole.

74. A compound according to claim 24 wherein $R_1$ and $R_2$, together with the nitrogen atom to which $R_1$ and $R_2$ are attached, form morpholinyl.

75. A compound according to claim 1 wherein A is 1-(phenylmethyl)-pyrrolidin-3-yl.

76. The compound of claim 75 which is (S)-(+)-3-[3-(1-benzyl-pyrrolidin-3-yloxy)-phenyl]-thieno[2,3-d]isoxazole.

77. The compound according to claim 75 which is (R)-(−)-3-[3-(1-benzyl-pyrrolidin-3-yloxy)-phenyl]-thieno[2,3-d]isoxazole.

78. A composition comprising a compound according to claim 1 in admixture with an inert carrier.

79. The composition according to claim 78 wherein said inert carrier is a pharmaceutical carrier.

80. A method of treating psychoses comprising administering to a patient in need thereof a therapeutically effective amount of a compound according to claim 1.

81. The method as defined in claim 80 wherein the compound is (3-fluoro-benzyl)-[2-(3-thieno[2,3-d]isoxazol-3-yl-phenoxy)-ethyl]-amine.

82. A method of treating Parkinson's Disease comprising administering to a patient in need thereof a therapeutically effective amount of a compound according to claim 1.

83. The method as defined in claim 82 wherein the compound is (3-fluoro-benzyl)-[2-(3-thieno[2,3-d]isoxazol-3-yl-phenoxy)-ethyl]-amine.

84. A method of treating Parkinsonism comprising administering to a patient in need thereof a therapeutically effective amount of a compound according to claim 1.

85. The method as defined in claim 84 wherein the compound is (3-fluoro-benzyl)-[2-(3-thieno[2,3-d]isoxazol-3-yl-phenoxy)-ethyl]-amine.

86. A method of treating Tardive Dyskinesia comprising administering to a patient in need thereof a therapeutically effective amount of a compound according to claim 1.

87. The method as defined in claim 86 wherein the compound is (3-fluoro-benzyl)-[2-(3-thieno[2,3-d]isoxazol-3-yl-phenoxy)-ethyl]-amine.

88. A method of making a compound of Formula I:

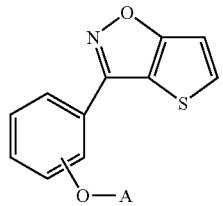

a pharmaceutically acceptable salt or stereoisomer thereof, wherein

A is $C_{2-3}$ alkylene-N($R_1$)($R_2$);
$R_1$ is $(CH_2)_nQ$, $CH_2CH(OH)Q$, $CH(CH_3)Q$, 1,2,3,4-tetrahydronaphthyl, indanyl, or adamantyl, wherein
Q is thienyl, phenyl, furanyl, naphthyl, pyridyl, indolyl, indazolyl, cyclohexyl, 1,2-methylenedioxyphenyl, cyclohexenyl, 1H-pyrazolo[4,3-c]pyridyl; and
Q is optionally substituted with one or two moieties independently selected from halo, $C_{1-6}$ alkyl, $C_{1-6}$ alkoxy, hydroxy, $S(O)_2NH_2$, trifluoromethyl, or cyano, and
n is 1 or 2;
$R_2$ is H or $C_{1-6}$ alkyl; or
$R_1$ and $R_2$, together with the nitrogen atom to which $R_1$ and $R_2$ are attached, form 4,5,6,7-tetrahydrothieno[3,2-c] pyridinyl, 1,4-dioxa-8-azo-spiro[4.5]decanyl, piperazinyl, morpholinyl, piperidinyl, pyrrolidinyl, azocanyl, azepanyl, 1,2,3,4-tetrahydroisoquinolinyl, 1,2,3,4-tetrahydro-1H-β-carbolinyl, or 8-aza-bicyclo[3.2.1]octanyl, each of which may be mono- or independently di-substituted with halo, $C_{1-6}$ alkyl, $C_{1-6}$ alkoxy, C(O)phenyl, OH, CN, O-phenyl or $(CH_2)_mZ$, Z is benzisoxazolyl, indazolyl, benzisothiazolyl, benzthienyl, pyrimidinyl; pyridyl, 1,2-methylenedioxyphenyl, or phenyl, and
Z, CH(OH)phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$, or cyano, and
m is 0 or 1;

comprising the step coupling a reagent of formula II

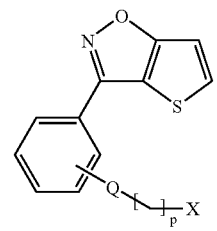

wherein
X is Br, Cl or I; and
p is 2 or 3;
with a reagent of formula III

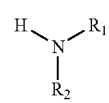

wherein $R_1$ and $R_2$ are defined as in formula I;
to provide a compound of formula I.

89. A method of making a compound of Formula I:

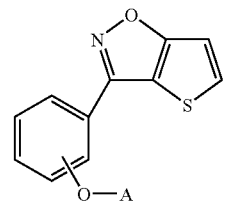

a pharmaceutically acceptable salt or stereoisomer thereof, wherein
A is 1-(phenylmethyl)-pyrrolidin-3-yl;
comprising the step of coupling a reagent of formula II

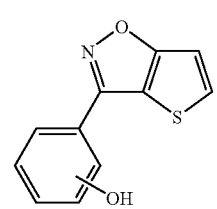

-continued

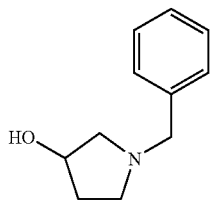

III with a reagent of formula III
to provide the compound of formula I.

90. A method of making a compound of Formula I:

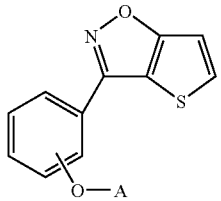

I a pharmaceutically acceptable salt or stereoisomer thereof, wherein

A is $C_{2-3}$ alkylene-N($R_1$)($R_2$);

$R_1$ is $(CH_2)_nQ$, $CH_2CH(OH)Q$, $CH(CH_3)Q$, 1,2,3,4-tetrahydronaphthyl, indanyl, or adamantyl, wherein Q is thienyl, phenyl, furanyl, naphthyl, pyridyl, indolyl, indazolyl, cyclohexyl, 1,2-methylenedioxyphenyl, cyclohexenyl, 1H-pyrazolo[4,3-c]pyridyl; and Q is optionally substituted with one or two moieties independently selected from halo, $C_{1-6}$ alkyl, $C_{1-6}$ alkoxy, hydroxy, $S(O)_2NH_2$, trifluoromethyl, or cyano, and n is 1 or 2;

$R_2$ is H or $C_{1-6}$ alkyl; or $R_1$ and $R_2$, together with the nitrogen atom to which $R_1$ and $R_2$ are attached, form 4,5,6,7-tetrahydrothieno[3,2-c]pyridinyl, 1,4-dioxa-8-azo-spiro[4.5]decanyl, piperazinyl, morpholinyl, piperidinyl, pyrrolidinyl, azocanyl, azepanyl, 1,2,3,4-tetrahydroisoquinolinyl, 1,2,3,4-tetrahydro-1H-β-carbolinyl, or 8-aza-bicyclo[3.2.1.]octanyl, each of which may be mono- or independently di-substituted with halo, $C_{1-6}$ alkyl, $C_{1-6}$ alkoxy, C(O)phenyl, OH, CN, O-phenyl or $(CH_2)_mZ$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl or O-phenyl are optionally substituted with one or two moieties, independently selected from halo, $C_{1-6}$ alkyl, $C_{1-6}$ alkoxy, hydroxy, trifluoromethyl, $S(O)_2NH_2$, or cyano, and m is 0 or 1;

comprising the step of coupling a reagent of formula II

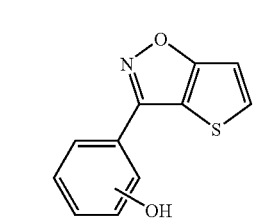

II with a reagent of formula m

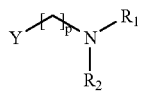

III wherein $R_1$, and $R_2$ are defined as in formula I;
p is 2 or 3; and
Y is Br, Cl, I, aryl sulfonate or alkyl sulfonate;
to provide the compound of formula I.

91. A method of making a compound of Formula I:

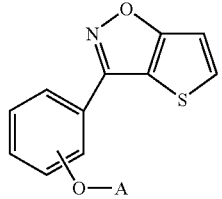

I a pharmaceutically acceptable salt or stereoisomer thereof, wherein

A is $C_{2-3}$alkylene-N($R_1$)($R_2$);

$R_1$ is $(CH_2)_nQ$, $CH_2CH(OH)Q$, $CH(CH_3)Q$, 1,2,3,4-tetrahydronaphthyl, indanyl, or adamantyl, wherein Q is thienyl, phenyl, furanyl, naphthyl, pyridyl, indolyl, indazolyl, cyclohexyl, 1,2-methylenedioxyphenyl, cyclohexenyl, 1H-pyrazolo[4,3-c]pyridyl; and Q is optionally substituted with one or two moieties independently selected from halo, $C_{1-6}$alkyl, $C_{1-6}$ alkoxy, hydroxy, $S(O)_2NH_2$, trifluoromethyl, or cyano, and n is 1 or 2;

$R_2$ is H or $C_{1-6}$ alkyl; or $R_1$ and $R_2$, together with the nitrogen atom to which $R_1$ and $R_2$ are attached, form 4,5,6,7-tetrahydrothieno[3,2-c]pyridinyl, 1,4-dioxa-8-azo-spiro[4.5]decanyl, piperazinyl, morpholinyl, piperidinyl, pyrrolidinyl, azocanyl, azepanyl, 1,2,3,4-tetrahydroisoquinolinyl, 1,2,3,4-tetrahydro-1H-β-carbolinyl, or 8-aza-bicyclo[3.2.1.]octanyl, each of which nay be mono- or independently di-substituted with halo, $C_{1-6}$ alkyl, $C_{1-6}$ alkoxy, C(O)phenyl, OH, CN, O-phenyl or $(CH_2)_mZ$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$, or cyano, and m is 0 or 1;

comprising the step of reducing a compound of the formula

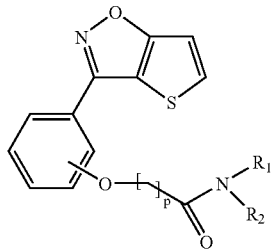

II wherein p is 1 or 2; and $R_1$ and $R_2$ are as defined in formula I;

to provide a compound of formula I.

92. A compound of formula

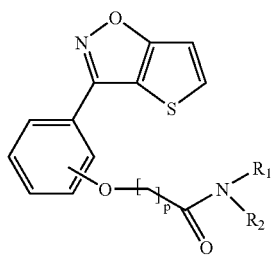

wherein p is 1 or 2; and $R_1$ is $(CH_2)_nQ$, $CH_2CH(OH)Q$, $CH(CH_3)Q$, 1,2,3,4-tetrahydronaphthyl, indanyl, or adamantyl, wherein Q is thienyl, phenyl, furanyl, naphthyl, pyridyl, indolyl, indazolyl, cyclohexyl, 1,2-methylenedioxyphenyl, cyclohexenyl, 1H-pyrazolo[4,3-c]pyridyl; and Q is optionally substituted with one or two moieties independently selected from halo, $C_{1-6}$ alkyl, $C_{1-6}$ alkoxy, hydroxy, $S(O)_2NH_2$, trifluoromethyl, or cyano, and n is 1 or 2;

$R_2$ is H or $C_{1-6}$ alkyl; or $R_1$ and $R_2$, together with the nitrogen atom to which $R_1$ and $R_2$ are attached, form 4,5,6,7-tetrahydrothieno[3-c] pyridinyl, 1,4-dioxa-8-azo-spiro[4.5]decanyl, piperazinyl, morpholinyl, piperidinyl, pyrrolidinyl, azocanyl, azepanyl, 1,2,3,4-tetrahydroisoquinolinyl, 1,2,3,4-tetrahydro-1H-β-carbolinyl, or 8-aza-bicyclo[3.2.1.]octanyl, each of which may be mono- or independently di-substituted with halo, $C_{1-6}$ alkyl, $C_{1-6}$ alkoxy, C(O)phenyl, OH, CN, O-phenyl or $(CH_2)_mZ$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$, or cyano, and m is 0 or 1.

93. A compound of formula

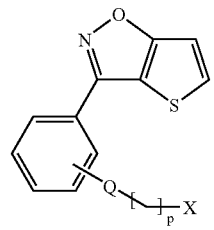

wherein

X is Br, Cl or I; and p is 2 or 3.

* * * * *